(12) United States Patent
Lee et al.

(10) Patent No.: US 11,891,632 B2
(45) Date of Patent: Feb. 6, 2024

(54) DNA POLYMERASE WITH INCREASED GENE MUTATION SPECIFICITY

(71) Applicant: GENECAST CO., LTD., Seongnam-si (KR)

(72) Inventors: Byung Chul Lee, Hanam-si (KR); Il Hyun Park, Hanam-si (KR); Huy Ho Lee, Seongnam-si (KR)

(73) Assignee: GENECAST CO., LTD, Seongnam-si (KR)

( * ) Notice: Subject to any disclaimer, the term of this patent is extended or adjusted under 35 U.S.C. 154(b) by 316 days.

(21) Appl. No.: 16/630,229

(22) PCT Filed: May 31, 2018

(86) PCT No.: PCT/KR2018/006246
§ 371 (c)(1),
(2) Date: Jan. 10, 2020

(87) PCT Pub. No.: WO2019/013451
PCT Pub. Date: Jan. 17, 2019

(65) Prior Publication Data
US 2020/0149018 A1    May 14, 2020

(30) Foreign Application Priority Data

Jul. 12, 2017 (KR) .................. 10-2017-0088373
Jul. 12, 2017 (KR) .................. 10-2017-0088376

(51) Int. Cl.
| | |
|---|---|
| C07K 1/00 | (2006.01) |
| C12Q 1/68 | (2018.01) |
| C12N 9/12 | (2006.01) |
| C12N 15/70 | (2006.01) |
| C12Q 1/6827 | (2018.01) |
| C12Q 1/686 | (2018.01) |
| C12Q 1/6883 | (2018.01) |

(52) U.S. Cl.
CPC ........... *C12N 9/1252* (2013.01); *C12N 15/70* (2013.01); *C12Q 1/686* (2013.01); *C12Q 1/6827* (2013.01); *C12Q 1/6883* (2013.01); *C12Y 207/07007* (2013.01); *C12Q 2600/156* (2013.01)

(58) Field of Classification Search
USPC ........... 435/6.1, 6.11, 7.1, 91.1, 91.2, 91.51; 436/94, 501; 536/23.1, 24.3, 24.33, 25.3; 530/300, 350
See application file for complete search history.

(56) References Cited

U.S. PATENT DOCUMENTS

| | | |
|---|---|---|
| 5,496,699 A | 3/1996 | Sorenson |
| 5,521,301 A | 5/1996 | Wallace et al. |
| 5,595,890 A | 1/1997 | Wallace et al. |
| 5,639,611 A | 6/1997 | Wallace et al. |
| 2009/0191560 A1 | 7/2009 | Chatterjee |
| 2011/0027833 A1 | 2/2011 | Holly et al. |
| 2016/0298174 A1 | 10/2016 | Marx et al. |

FOREIGN PATENT DOCUMENTS

| | | |
|---|---|---|
| EP | 2554665 A2 | 2/2013 |
| EP | 2907871 A1 | 8/2015 |
| EP | 3077532 B1 | 6/2019 |
| WO | 2015/082449 A2 | 6/2015 |

OTHER PUBLICATIONS

Raghunathan et al., Identification of Thermus aquaticus DNA polymerase variants with increased mismatch discrimination and reverse transcriptase activity from a smart enzyme mutant library. Scientific Reports, 9, 590, 2019.*
Medrano et al., Guidelines for the Tetra-Primer ARMS—PCR Technique Development. Mol. Biotechnol., 56, 599-608, 2014.*
Barbano et al., Competitive allele-specific TaqMan PCR (Cast-PCR) is a sensitive, specific and fast method for BRAF V600 mutation detection in Melanoma patients. Nature Scientific Reports, 5, 18592, 2015.*
Alliancebio, Buffer Optimization Kit, Cat. No.: M061RB33—3 pages ( Jul. 2007).
Ugozzoli et al., "Application of an Allele-specific Polymerase Chain Reaction to the Direct Determination of ABO Blood Group Genotypes", Genomics, vol. 12, No. 4—5 pages (1992).
International Search Report of corresponding PCT Application No. PCT/KR2018/006246—4 pages (Sep. 7, 2018).
"RecName: Full=DNA polymerase I, thermostable; AltName: Full= Taq polymerase 1" downloaded from https://www.ncbi.nlm.nih.gov/protein/P19821—11 pages. (Downloaded Jan. 9, 2020).
Barnes, "The fidelity of Taq polymerase catalyzing PCR is improved by an N-terminal deletion", Gene, vol. 112, Issue 1, Mar. 1, 1992, pp. 29-35 (Mar. 1, 1992).
Arezi et al., "Compartmentalized self-replication under fast PCR cycling conditions yields Taq DNA polymerase mutants with increased DNA-binding affinity and blood resistance" Frontiers in Microbiology, Aug. 2014, vol. 5 Article 408—11 pages (Aug. 2014).

(Continued)

*Primary Examiner* — Frank W Lu
(74) *Attorney, Agent, or Firm* — Knobbe Martens Olson & Bear LLP

(57) ABSTRACT

A DNA polymerase in which a mutation is induced at a specific amino acid position to increase gene mutation specificity, a nucleic acid sequence encoding the polymerase, a vector comprising the nucleic acid sequence, and a host cell transformed with the vector are disclosed. Provided are a method for in vitro detecting one or more gene mutations or SNPs in one or more templates by using a DNA polymerase having increased gene mutation specificity, a composition for detecting a gene mutation or SNP comprising the DNA polymerase, and a PCR kit comprising said composition. Furthermore, provided are a PCR buffer composition for increasing the activity of a DNA polymerase having increased gene mutation specificity and a PCR kit for detecting a gene mutation or SNP comprising the PCR buffer composition and/or the DNA polymerase having increased gene mutation specificity.

14 Claims, 34 Drawing Sheets
Specification includes a Sequence Listing.

(56) References Cited

OTHER PUBLICATIONS

Drum et al., "Variants of a Thermus aquaticus DNA Polymerase with Increased Selectivity for Applications in Allele- and Methylation-Specific Amplification" PLOS ONE, May 2014, vol. 9, Issue 5 e96640—11 pages (May 2014).

Ivo G. Gut, " Automation in Genotyping of Single Nucleotide Polymorphisms", Human Mutation 17:475-492—18 pages (2001).

* cited by examiner

GEL EXTRACTION (1 UL LOADING)

(a)

(b)

PURIFICATION (ELUTION : 25 UL)

KRAS G13D

(a) E507K/R536K/R660V

(b) E507K/R536K/R587I/R660V

KRAS G12S

EGFR L858R (a) E507K/R536K/R660V (b) E507K/R536K/R587I/R660V

SEQUENCE LISTING

<160> NUMBER OF SEQ ID NOS: 61

<210> SEQ ID NO 1
<211> LENGTH: 832
<212> TYPE: PRT
<213> ORGANISM: Artificial
<220> FEATURE:
<223> OTHER INFORMATION: Thermus aquaticus DNA polymerase (Taq)

<400> SEQUENCE: 1

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205
```

-continued

```
Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
```

-continued

```
            625                 630                 635                 640
Glu Thr Ala Ser Trp Met Phe Gly Val Pro Arg Glu Ala Val Asp Pro
                    645                 650                 655
Leu Met Arg Arg Ala Ala Lys Thr Ile Asn Phe Gly Val Leu Tyr Gly
                    660                 665                 670
Met Ser Ala His Arg Leu Ser Gln Glu Leu Ala Ile Pro Tyr Glu Glu
                    675                 680                 685
Ala Gln Ala Phe Ile Glu Arg Tyr Phe Gln Ser Phe Pro Lys Val Arg
                    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                    725                 730                 735
Val Lys Ser Val Arg Glu Ala Ala Glu Arg Met Ala Phe Asn Met Pro
                    740                 745                 750
Val Gln Gly Thr Ala Ala Asp Leu Met Lys Leu Ala Met Val Lys Leu
                    755                 760                 765
Phe Pro Arg Leu Glu Glu Met Gly Ala Arg Met Leu Leu Gln Val His
                    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                    805                 810                 815
Leu Glu Val Glu Val Gly Ile Gly Glu Asp Trp Leu Ser Ala Lys Glu
                    820                 825                 830
```

<210> SEQ ID NO 2
<211> LENGTH: 832
<212> TYPE: PRT
<213> ORGANISM: Artificial
<220> FEATURE:
<223> OTHER INFORMATION: Taq E507K

<400> SEQUENCE: 2

```
Met Arg Gly Met Leu Pro Leu Phe Glu Pro Lys Gly Arg Val Leu Leu
1                   5                   10                  15
Val Asp Gly His His Leu Ala Tyr Arg Thr Phe His Ala Leu Lys Gly
                    20                  25                  30
Leu Thr Thr Ser Arg Gly Glu Pro Val Gln Ala Val Tyr Gly Phe Ala
                    35                  40                  45
Lys Ser Leu Leu Lys Ala Leu Lys Glu Asp Gly Asp Ala Val Ile Val
                    50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                    85                  90                  95
Ala Leu Ile Lys Glu Leu Val Asp Leu Leu Gly Leu Ala Arg Leu Glu
                    100                 105                 110
Val Pro Gly Tyr Glu Ala Asp Asp Val Leu Ala Ser Leu Ala Lys Lys
                    115                 120                 125
Ala Glu Lys Glu Gly Tyr Glu Val Arg Ile Leu Thr Ala Asp Lys Asp
                    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
```

```
                165                 170                 175
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590
```

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 3
<211> LENGTH: 832
<212> TYPE: PRT
<213> ORGANISM: Artificial
<220> FEATURE:
<223> OTHER INFORMATION: Taq R536K

<400> SEQUENCE: 3

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
            50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

```
Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Lys Glu Leu Thr Lys Leu Lys Ser Thr
530                 535                 540
```

```
Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 4
<211> LENGTH: 832
<212> TYPE: PRT
<213> ORGANISM: Artificial
<220> FEATURE:
<223> OTHER INFORMATION: Taq R660V

<400> SEQUENCE: 4

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80
```

```
Tyr Lys Ala Gly Arg Ala Pro Thr Pro Glu Asp Phe Pro Arg Gln Leu
             85                  90                  95

Ala Leu Ile Lys Glu Leu Val Asp Leu Gly Leu Ala Arg Leu Glu
        100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
```

```
                500             505             510
Ser Thr Ser Ala Ala Val Leu Glu Ala Leu Arg Glu Ala His Pro Ile
        515             520             525

Val Glu Lys Ile Leu Gln Tyr Arg Glu Leu Thr Lys Leu Lys Ser Thr
        530             535             540

Tyr Ile Asp Pro Leu Pro Asp Leu Ile His Pro Arg Thr Gly Arg Leu
545             550             555             560

His Thr Arg Phe Asn Gln Thr Ala Thr Ala Thr Gly Arg Leu Ser Ser
                565             570             575

Ser Asp Pro Asn Leu Gln Asn Ile Pro Val Arg Thr Pro Leu Gly Gln
        580             585             590

Arg Ile Arg Arg Ala Phe Ile Ala Glu Gly Trp Leu Leu Val Ala
        595             600             605

Leu Asp Tyr Ser Gln Ile Glu Leu Arg Val Leu Ala His Leu Ser Gly
        610             615             620

Asp Glu Asn Leu Ile Arg Val Phe Gln Glu Gly Arg Asp Ile His Thr
625             630             635             640

Glu Thr Ala Ser Trp Met Phe Gly Val Pro Arg Glu Ala Val Asp Pro
                645             650             655

Leu Met Arg Val Ala Ala Lys Thr Ile Asn Phe Gly Val Leu Tyr Gly
        660             665             670

Met Ser Ala His Arg Leu Ser Gln Glu Leu Ala Ile Pro Tyr Glu Glu
        675             680             685

Ala Gln Ala Phe Ile Glu Arg Tyr Phe Gln Ser Phe Pro Lys Val Arg
        690             695             700

Ala Trp Ile Glu Lys Thr Leu Glu Glu Gly Arg Arg Arg Gly Tyr Val
705             710             715             720

Glu Thr Leu Phe Gly Arg Arg Arg Tyr Val Pro Asp Leu Glu Ala Arg
                725             730             735

Val Lys Ser Val Arg Glu Ala Ala Glu Arg Met Ala Phe Asn Met Pro
        740             745             750

Val Gln Gly Thr Ala Ala Asp Leu Met Lys Leu Ala Met Val Lys Leu
        755             760             765

Phe Pro Arg Leu Glu Glu Met Gly Ala Arg Met Leu Leu Gln Val His
        770             775             780

Asp Glu Leu Val Leu Glu Ala Pro Lys Glu Arg Ala Glu Ala Val Ala
785             790             795             800

Arg Leu Ala Lys Glu Val Met Glu Gly Val Tyr Pro Leu Ala Val Pro
                805             810             815

Leu Glu Val Glu Val Gly Ile Gly Glu Asp Trp Leu Ser Ala Lys Glu
        820             825             830

<210> SEQ ID NO 5
<211> LENGTH: 832
<212> TYPE: PRT
<213> ORGANISM: Artificial
<220> FEATURE:
<223> OTHER INFORMATION: Taq R536K/R660V

<400> SEQUENCE: 5

Met Arg Gly Met Leu Pro Leu Phe Glu Pro Lys Gly Arg Val Leu Leu
1               5               10              15

Val Asp Gly His His Leu Ala Tyr Arg Thr Phe His Ala Leu Lys Gly
            20              25              30

Leu Thr Thr Ser Arg Gly Glu Pro Val Gln Ala Val Tyr Gly Phe Ala
```

```
            35                  40                  45
Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460
```

Glu Ile Ala Arg Leu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Lys Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Val Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 6
<211> LENGTH: 832
<212> TYPE: PRT
<213> ORGANISM: Artificial
<220> FEATURE:
<223> OTHER INFORMATION: Taq E507K/R536K

<400> SEQUENCE: 6

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

```
Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Lys Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830
```

<210> SEQ ID NO 7
<211> LENGTH: 832
<212> TYPE: PRT
<213> ORGANISM: Artificial
<220> FEATURE:
<223> OTHER INFORMATION: Taq E507K/R660V

<400> SEQUENCE: 7

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
```

-continued

```
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                    405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                    485                 490                 495
Glu Leu Gly Leu Pro Ala Ile Gly Lys Thr Lys Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
        530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                    565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
        610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                    645                 650                 655
Leu Met Arg Val Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                    725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
        770                 775                 780
Asp Glu Leu Val Leu Glu Ala Pro Lys Glu Arg Ala Glu Ala Val Ala
785                 790                 795                 800
```

```
Arg Leu Ala Lys Glu Val Met Glu Gly Val Tyr Pro Leu Ala Val Pro
            805                 810                 815
Leu Glu Val Glu Val Gly Ile Gly Glu Asp Trp Leu Ser Ala Lys Glu
        820                 825                 830

<210> SEQ ID NO 8
<211> LENGTH: 832
<212> TYPE: PRT
<213> ORGANISM: Artificial
<220> FEATURE:
<223> OTHER INFORMATION: Taq E507K/R536K/R660V

<400> SEQUENCE: 8

Met Arg Gly Met Leu Pro Leu Phe Glu Pro Lys Gly Arg Val Leu Leu
1               5                   10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Asp Ala Val Ile Val
    50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
```

```
Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Lys Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Val Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750
```

```
Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 9
<211> LENGTH: 2499
<212> TYPE: DNA
<213> ORGANISM: Artificial
<220> FEATURE:
<223> OTHER INFORMATION: Thermus aquaticus DNA polymerase (Taq)

<400> SEQUENCE: 9
atgaggggga tgctgcccct ctttgagccc aagggccggg tcctcctggt ggacggccac      60
cacctggcct accgcacctt ccacgccctg aagggcctca ccaccagccg gggggagccg     120
gtgcaggcgg tctacggctt cgccaagagc ctcctcaagg ccctcaagga ggacggggac     180
gcggtgatcg tggtctttga cgccaaggcc cctccttcc gccacgaggc ctacggggg      240 tacaaggcgg ccgggccc cacgccggag actttcccc ggcaactcgc cctcatcaag       300
gagctggtgg acctcctggg ctggcgcgc ctcgaggtcc cgggctacga ggcggacgac     360
gtcctggcca gcctggccaa gaaggcggaa aaggagggct acgaggtccg catcctcacc     420
gccgacaaag acctttacca gctcctttcc gaccgcatcc acgtcctcca ccccgagggg     480
tacctcatca cccccggcctg gctttgggaa agtacggcc tgaggcccga ccagtgggcc     540
gactaccggg ccctgaccgg ggacgagtcc gacaaccttc cgggggtcaa gggcatcggg     600
gagaagacgg cgaggaagct tctggaggag tgggggagcc tggaagccct cctcaagaac     660
ctggaccggc tgaagcccgc catccggag aagatcctgg cccacatgga cgatctgaag     720
ctctcctggg acctggccaa ggtgcgcacc gacctgcccc tggaggtgga cttcgccaaa     780
aggcgggagc ccgaccggga gaggcttagg gcctttctgg agaggcttga gtttggcagc     840
ctcctccacg agttcggcct tctggaaagc cccaaggccc tggaggaggc ccctggcccc     900
ccgccggaag ggccttcgt gggctttgtg cttcccgca aggagcccat gtgggccgat     960
cttctggccc tggccgccgc caggggggc cgggtccacc gggcccccga gccttataaa    1020
gccctcaggg acctgaagga ggcgcgggg cttctcgcca aagacctgag cgttctggcc    1080
ctgagggaag gccttggcct cccgcccggc gacgacccca tgctcctcgc ctacctcctg    1140
gacccttcca acaccacccc cgaggggtg gccggcgct acggcgggga gtggacggag    1200 gaggcgggg agcgggccgc cctttccgag aggctcttcg ccaacctgtg ggggaggctt    1260 gaggggagg agaggctcct ttggctttac cgggaggtgg agaggcccct ttccgctgtc    1320
ctggcccaca tggaggccac ggggggtgcgc ctggacgtgg cctatctcag ggccttgtcc    1380
ctggaggtgg ccgaggagat cgcccgcctc gaggccgagt cttccgcct ggccggccac    1440 cccttcaacc tcaactcccg ggaccagctg gaaagggtcc tctttgacga gctagggctt    1500
cccgccatcg gcaagacgga aaagaccggc aagcgctcca ccagcgccgc cgtcctggag    1560
gccctccgcg aggcccaccc catcgtggag aagatcctgc agtaccggga gctcaccaag    1620
```

```
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggg ggctattggt ggccctggac tatagccaga tagagctcag ggtgctggcc    1860
cacctctccg gcgacgagaa cctgatccgg gtcttccagg agggcggga catccacacg    1920
gagaccgcca gctggatgtt cggcgtcccc cgggaggccg tggacccct gatgcgccgg     1980
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg     2160
gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatggggc caggatgctc     2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtga                            2499

<210> SEQ ID NO 10
<211> LENGTH: 2499
<212> TYPE: DNA
<213> ORGANISM: Artificial
<220> FEATURE:
<223> OTHER INFORMATION: Taq E507K

<400> SEQUENCE: 10 atgagggga tgctgcccct ctttgagccc aagggccggg tcctcctggt ggacggccac     60
cacctggcct accgcacctt ccacgccctg aagggcctca ccaccagccg gggggagccg    120
gtgcaggcgg tctacggctt cgccaagagc ctcctcaagg ccctcaagga ggacggggac    180
gcggtgatcg tggtctttga cgccaaggcc ccctccttcc gccacgaggc ctacgggggg    240
tacaaggcgg gccgggcccc cacgccggag gactttcccc ggcaactcgc cctcatcaag    300
gagctggtgg acctcctggg gctggcgcgc ctcgaggtcc cgggctacga ggcggacgac    360
gtcctggcca gcctggccaa gaaggcggaa aaggagggct acgaggtccg catcctcacc    420
gccgacaaag acctttacca gctcctttcc gaccgcatcc acgtcctcca ccccgagggg    480
tacctcatca cccccggcctg gctttgggaa aagtacggcc tgaggcccga ccagtgggcc    540
gactaccggg ccctgaccgg ggacgagtcc gacaaccttc cgggggtcaa gggcatcggg    600
gagaagacgc gaggaagct tctggaggag tgggggagcc tggaagccct cctcaagaac    660
ctggaccggc tgaagcccgc catccgggag aagatcctgg cccacatgga cgatctgaag    720
ctctcctggg acctgccaa ggtgcgcacc gacctgcccc tggaggtgga cttcgccaaa    780
aggcgggagc ccgaccggga ggcttaggg gcctttctgg agaggcttga gtttggcagc    840
ctcctccacg agttcggcct tctggaaagc cccaaggccc tggaggaggc ccctggccc    900
ccgccggaag gggccttcgt gggctttgtg ctttcccgca aggagcccat gtgggccgat    960
cttctggccc tggccgccgc caggggggc cgggtccacc gggccccga gccttataaa    1020
gccctcaggg acctgaagga ggcgggggg cttctcgcca aagacctgag cgttctggcc    1080
ctgagggaag gccttggcct cccgcccggc gacgacccca tgctcctcgc ctacctcctg    1140
gacccttcca acaccacccc cgagggggtg gcccggcgct acgcgggga gtggacggag    1200
```

```
gaggcggggg agcgggccgc cctttccgag aggctcttcg ccaacctgtg ggggaggctt   1260 gaggggggagg agaggctcct ttggctttac cgggaggtgg agaggcccct ttccgctgtc   1320
ctggcccaca tggaggccac gggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgaa aaagaccggc aagcgctcca ccagcgccgc cgtcctggag   1560
gccctccgcg aggcccaccc catcgtggag aagatcctgc agtaccggga gctcaccaag   1620
ctgaagagca cctacattga ccccttgccg gacctcatcc accccaggac gggccgcctc   1680
cacacccgct caaccagac ggccacggcc acgggcaggc taagtagctc cgatcccaac   1740
ctccagaaca tccccgtccg caccccgctt gggcagagga tccgccgggc cttcatcgcc   1800 gaggagggt ggctattggt ggccctggac tatagccaga tagagctcag ggtgctggcc   1860
cacctctccg cgacgagaa cctgatccgg gtcttccagg aggggcggga catccacacg   1920
gagaccgcca gctggatgtt cggcgtcccc cgggaggccg tggaccccct gatgcgccgg   1980
gcggccaaga ccatcaactt cggggtcctc tacggcatgt cggcccaccg cctctcccag   2040
gagctagcca tcccttacga ggaggcccag gccttcattg agcgctactt tcagagcttc   2100
cccaaggtgc gggcctggat tgagaagacc ctggaggagg caggaggcg ggggtacgtg   2160 gagaccctct tcggccgccg ccgctacgtg ccagacctag aggcccgggt gaagagcgtg   2220
cgggaggcgg ccgagcgcat ggccttcaac atgcccgtcc agggcaccgc cgccgacctc   2280
atgaagctgg ctatggtgaa gctcttcccc aggctggagg aaatgggggc caggatgctc   2340
cttcaggtcc acgacgagct ggtcctcgag gccccaaaag agagggcgga ggccgtggcc   2400
cggctggcca aggaggtcat ggaggggtg tatcccctgg ccgtgcccct ggaggtggag   2460
gtggggatag ggaggactg gctctccgcc aaggagtga                          2499
```

<210> SEQ ID NO 11
<211> LENGTH: 2499
<212> TYPE: DNA
<213> ORGANISM: Artificial
<220> FEATURE:
<223> OTHER INFORMATION: Taq R536K

<400> SEQUENCE: 11

```
atgagggga tgctgcccct ctttgagccc aagggccggg tcctcctggt ggacggccac     60
cacctggcct accgcacctt ccacgccctg aaggcctca ccaccagccg ggggagccg    120 gtgcaggcgg tctacggctt cgccaagagc ctcctcaagg ccctcaagga ggacggggac   180
gcggtgatcg tggtctttga cgccaaggcc ccctccttcc gccacgaggc ctacggggg   240 tacaaggcgg gccggccc cacgccggag gactttcccc ggcaactcgc cctcatcaag   300
gagctggtgg acctcctggg gctggcgcgc tcgaggtcc cgggctacga ggcggacgac   360
gtcctggcca gcctggccaa gaaggcggaa aaggagggct acgaggtccg catcctcacc   420
gccgacaaag accttaccca gctcctttc gaccgcatcc acgtcctcca ccccgagggg   480 taccctcatca ccccggcctg gctttgggaa agtacggcc tgaggcccga ccagtgggcc   540
gactaccggg ccctgaccgg ggacgagtcc gacaaccttc cggggtcaa gggcatcggg   600 gagaagacgc gaggaagct tctggaggag tgggggagcc tggaagccct cctcaagaac   660
ctggaccggc tgaagcccgc catccgggag aagatcctgg cccacatgga cgatctgaag   720
```

| | |
|---|---:|
| ctctcctggg acctggccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc ccctggccc | 900 |
| ccgccggaag gggccttcgt gggctttgtg cttccccgca aggagcccat gtgggccgat | 960 |
| cttctggccc tggccgccgc caggggggc cgggtccacc gggcccccga gccttataaa | 1020 |
| gccctcaggg acctgaagga ggcgcggggg cttctcgcca aagacctgag cgttctggcc | 1080 |
| ctgagggaag gccttggcct cccgcccggc gacgacccca tgctcctcgc ctacctcctg | 1140 |
| gaccctccca acaccacccc cgaggggggtg gccggcgct acggcgggga gtggacggag | 1200 |
| gaggcggggg agcgggccgc cctttccgag aggctcttcg ccaacctgtg ggggaggctt | 1260 |
| gagggggagg agaggctcct ttggctttac cgggaggtgg agaggcccct ttccgctgtc | 1320 |
| ctggcccaca tggaggccac gggggtgcgc ctggacgtgg cctatctcag ggccttgtcc | 1380 |
| ctggaggtgg ccgaggagat cgcccgcctc gaggccgagg tcttccgcct ggccggccac | 1440 |
| cccttcaacc tcaactcccg ggaccagctg gaaagggtcc tctttgacga gctagggctt | 1500 |
| cccgccatcg gcaagacgga gaagaccggc aagcgctcca ccagcgccgc cgtcctggag | 1560 |
| gccctccgcg aggcccaccc catcgtggag aagatcctgc agtacaagga gctcaccaag | 1620 |
| ctgaagagca cctacattga ccccttgccg gacctcatcc accccaggac gggccgcctc | 1680 |
| cacacccgct caaccagac ggccacggcc acgggcaggc taagtagctc cgatcccaac | 1740 |
| ctccagaaca tccccgtccg caccccgctt gggcagagga tccgccgggc cttcatcgcc | 1800 |
| gaggaggggt ggctattggt ggccctggac tatagccaga tagagctcag ggtgctggcc | 1860 |
| cacctctccg cgacgagaa cctgatccgg gtcttccagg aggggcggga catccacacg | 1920 |
| gagaccgcca gctggatgtt cggcgtcccc cgggaggccg tggaccccct gatgcgccgg | 1980 |
| gcggccaaga ccatcaactt cggggtcctc tacggcatgt cggcccaccg cctctcccag | 2040 |
| gagctagcca tcccttacga ggaggccag gccttcattg agcgctactt tcagagcttc | 2100 |
| cccaaggtgc gggcctggat tgagaagacc ctggaggagg gcaggaggcg ggggtacgtg | 2160 |
| gagaccctct tcggccgccg ccgctacgtg ccagacctag aggcccgggt gaagagcgtg | 2220 |
| cgggaggcgg ccgagcgcat ggccttcaac atgcccgtcc agggcaccgc cgccgacctc | 2280 |
| atgaagctgg ctatggtgaa gctcttcccc aggctggagg aaatgggggc caggatgctc | 2340 |
| cttcaggtcc acgacgagct ggtcctcgag gccccaaaag agagggcgga ggccgtggcc | 2400 |
| cggctggcca aggaggtcat ggaggggggtg tatcccctgg ccgtgcccct ggaggtggag | 2460 |
| gtggggatag gggaggactg gctctccgcc aaggagtga | 2499 |

<210> SEQ ID NO 12
<211> LENGTH: 2499
<212> TYPE: DNA
<213> ORGANISM: Artificial
<220> FEATURE:
<223> OTHER INFORMATION: Taq R660V

<400> SEQUENCE: 12

| | |
|---|---:|
| atgagggga tgctgcccct cttgagccc aagggccggg tcctcctggt ggacggccac | 60 |
| cacctggcct accgcacctt ccacgccctg aagggcctca ccaccagccg gggggagccg | 120 |
| gtgcaggcgg tctacggctt cgccaagagc ctcctcaagg ccctcaagga ggacgggggac | 180 |
| gcggtgatcg tggtctttga cgccaaggcc ccctccttcc gccacgaggc ctacgggggg | 240 |
| tacaaggcgg gccgggcccc cacgccggag gactttcccc ggcaactcgc cctcatcaag | 300 |

```
gagctggtgg acctcctggg gctggcgcgc ctcgaggtcc cgggctacga ggcggacgac      360
gtcctggcca gcctggccaa gaaggcggaa aaggagggct acgaggtccg catcctcacc      420
gccgacaaag acctttacca gctcctttcc gaccgcatcc acgtcctcca ccccgagggg      480
tacctcatca ccccggcctg gctttgggaa aagtacggcc tgaggcccga ccagtgggcc      540
gactaccggg ccctgaccgg ggacgagtcc gacaaccttc cggggtcaa gggcatcggg       600 gagaagacgg cgaggaagct tctggaggag tgggggagcc tggaagccct cctcaagaac      660
ctggaccggc tgaagcccgc catccgggag aagatcctgg cccacatgga cgatctgaag      720
ctctcctggg acctggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc ccctggccc      900 ccgccggaag gggccttcgt gggctttgtg ctttcccgca aggagcccat gtgggccgat      960
cttctggccc tggccgccgc caggggggc cgggtccacc gggcccccga gccttataaa      1020
gccctcaggg acctgaagga ggcgcggggg cttctcgcca aagacctgag cgttctggcc      1080
ctgagggaag gccttggcct cccgccggc gacgacccca tgctcctcgc ctacctcctg       1140 gaccettcca acaccacccc cgaggggtg gcccggcgct acggcgggga gtggacggag      1200
gaggcgggga gcgggccgc cctttccgag aggctcttcg ccaacctgtg ggggaggctt      1260 gaggggagg agaggctcct ttggctttac cgggaggtgg agaggcccct ttccgctgtc      1320
ctggcccaca tggaggccac gggggtgcgc ctggacgtgg cctatctcag ggccttgtcc      1380
ctggaggtgg ccgaggagat cgcccgcctc gaggccgagg tcttccgcct ggccggccac      1440
cccttcaacc tcaactcccg ggaccagctg gaaagggtcc tctttgacga gctagggctt      1500
cccgccatcg gcaagacgga aagaccggc aagcgctcca ccagcgccgc cgtcctggag      1560
gccctccgcg aggcccaccc catcgtggag aagatcctgc agtaccggga gctcaccaag      1620
ctgaagagca cctacattga ccccttgccg gacctcatcc accccaggac gggccgcctc      1680
cacacccgct tcaaccagac ggccacggcc acgggcaggc taagtagctc cgatcccaac      1740
ctccagaaca tccccgtccg caccccgctt gggcagagga tccgccgggc cttcatcgcc      1800
gaggaggggt ggctattggt ggccctggac tatagccaga tagagctcag ggtgctggcc      1860
cacctctccg gcgacgagaa cctgatccgg gtcttccagg aggggcggga catccacacg      1920
gagaccgcca gctggatgtt cggcgtcccc cgggaggccg tggacccct gatgcgcgtg      1980 gcggccaaga ccatcaactt cggggtcctc tacggcatgt cggcccaccg cctctcccag      2040
gagctagcca tcccttacga ggaggccag gccttcattg agcgctactt tcagagcttc      2100
cccaaggtgc gggcctggat tgagaagacc ctggaggagg caggaggcg ggggtacgtg      2160 gagaccctct tcggccgccg ccgctacgtg ccagacctag aggcccgggt gaagagcgtg      2220 cgggaggcg ccgagcgcat ggccttcaac atgcccgtcc agggcaccgc cgccgacctc      2280
atgaagctgg ctatggtgaa gctcttcccc aggctggagg aaatgggggc aggatgctc       2340 cttcaggtcc acgacgagct ggtcctcgag gccccaaaag agagggcgga ggccgtggcc      2400
cggctggcca aggaggtcat ggaggggtg tatccctgg ccgtgccct ggaggtggag       2460 gtggggatag ggaggactg gctctccgcc aaggagtga                              2499

<210> SEQ ID NO 13
<211> LENGTH: 2499
<212> TYPE: DNA
```

<213> ORGANISM: Artificial
<220> FEATURE:
<223> OTHER INFORMATION: Taq R536K/R660V

<400> SEQUENCE: 13

```
atgagggggc tgctgccccc ctttgagccc aagggccggg tcctcctggt ggacggccac      60
cacctggcct accgcacctt ccacgccctg aagggcctca ccaccagccg gggggagccg     120
gtgcaggcgg tctacggctt cgccaagagc ctcctcaagg ccctcaagga ggacgggggac    180
gcggtgatcg tggtctttga cgccaaggcc ccctccttcc gccacgaggc ctacgggggg     240
tacaaggcgg ccgggcccc cacgccgag gactttcccc ggcaactcgc cctcatcaag       300
gagctggtgg acctcctggg gctggcgcgc ctcgaggtcc cgggctacga ggcggacgac     360
gtcctggcca gctggccaa gaaggcgaa aaggagggct acgaggtccg catcctcacc       420
gccgacaaag accttacca gctccttttcc gaccgcatcc acgtcctcca ccccgagggg    480
tacctcatca ccccggcctg gctttgggaa agtacggcc tgaggcccga ccagtgggcc      540
gactaccggg ccctgaccgg ggacgagtcc gacaacttc ccggggtcaa gggcatcggg      600
gagaagacgg cgaggaagct tctggaggag tgggggagcc tggaagccct cctcaagaac    660
ctggaccggc tgaagcccgc catccgggag aagatcctgg cccacatgga cgatctgaag     720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc ccctggcccc    900
ccgccgaag gggccttcgt gggctttgtg ctttcccgca aggagcccat gtgggccgat     960
cttctggccc tggccgccgc cagggggggc cgggtccacc gggcccccga gccttataaa   1020
gcctcaggg acctgaagga ggcgcgggg cttctcgcca agacctgag cgttctggcc       1080
ctgagggaag gccttggcct cccgcccggc gacgacccca tgctcctcgc ctacctcctg    1140
gacccttcca acaccacccc cgagggggtg cccggcgct acggcgggga gtggacggag    1200
gaggcggggg agcgggccgc cctttccgag aggctcttcg ccaacctgtg ggggaggctt    1260
gaggggggag agaggctcct ttggctttac cgggaggtgg agaggcccct ttccgctgtc    1320
ctggcccaca tggaggccac ggggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtacaagga gctcaccaag    1620
ctgaagagca cctacattga cccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc   1800
gaggaggggt ggctattggt ggccctggac tatagccaga tagagctcag ggtgctggcc   1860
cacctctccg gcgacgagaa cctgatccgg gtcttccagg aggggcggga catccacacg   1920
gagaccgcca gctggatgtt cggcgtcccc cggaggccg tggaccccct gatgcgcgtg    1980
gcggccaaga ccatcaactt cggggtcctc tacggcatgt cggcccaccg cctctcccag    2040
gagctagcca tcccttacga ggaggccag gccttcattg agcgctactt tcagagcttc    2100
cccaaggtgc gggcctggat tgagaagacc ctggaggagg caggaggcg ggggtacgtg    2160
gagacccctc tcggccgccg ccgctacgtg ccagacctag aggcccgggt gaagagcgtg    2220
```

```
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgccct ggaggtggag      2460 gtggggatag ggaggactg gctctccgcc aaggagtga                            2499
```

<210> SEQ ID NO 14
<211> LENGTH: 2499
<212> TYPE: DNA
<213> ORGANISM: Artificial
<220> FEATURE:
<223> OTHER INFORMATION: Taq E507K/R536

<400> SEQUENCE: 14

```
atgagggga tgctgcccct ctttgagccc aagggccggg tcctcctggt ggacggccac      60
cacctggcct accgcacctt ccacgccctg aagggcctca ccaccagccg gggggagccg    120
gtgcaggcgg tctacggctt cgccaagagc ctcctcaagg ccctcaagga ggacggggac    180
gcggtgatcg tggtctttga cgccaaggcc ccctccttcc gccacgaggc ctacggggg     240 tacaaggcgg gccgggcccc cacgccggag gactttcccc ggcaactcgc cctcatcaag    300
gagctggtgg acctcctggg gctggcgcgc tcgaggtcc cgggctacga ggcggacgac    360
gtcctggcca gcctggccaa gaaggcggaa aaggagggct acgaggtccg catcctcacc    420
gccgacaaag acctttacca gctcctttcc gaccgcatcc acgtcctcca ccccgagggg    480
tacctcatca ccccggcctg gctttgggaa agtacggcc tgaggcccga ccagtgggcc     540
gactaccggg ccctgaccgg ggacgagtcc gacaacctt ccggggtcaa gggcatcggg    600
gagaagacgg cgaggaagct tctggaggag tgggggagcc tggaagccct cctcaagaac    660
ctggaccggc tgaagcccgc catccggag aagatcctgg cccacatgga cgatctgaag     720
ctctcctggg acctggccaa ggtgcgcacc gacctgcccc tggaggtgga cttcgccaaa    780 aggcggagc ccgaccggga gaggcttagg gcctttctgg agaggcttga gtttggcagc    840
ctcctccacg agttcggcct tctggaaagc cccaaggcc tggaggaggc ccctggccc     900 ccgccggaag ggccttcgt gggctttgtg ctttcccgca aggagcccat gtgggccgat    960 cttctgccc tggccgccgc cagggggggc cgggtccacc gggcccccga gccttataaa    1020
gccctcaggg acctgaagga ggcgggggg cttctcgcca agacctgag cgttctggcc     1080 ctgagggaag gccttggcct cccgcccggc gacgaccca tgctcctcgc ctacctcctg    1140
gacccttcca acaccaccc cgaggggtg gcccggcgct acggcgggga gtggacggag     1200 gaggcgggg agcgggccgc ccttcccgag aggctcttcg ccaacctgtg ggggaggctt    1260
gagggggagg agaggctcct ttggctttac cgggaggtgg agaggcccct ttccgctgtc    1320
ctggcccaca tggaggccac ggggtgcgc ctggacgtgg cctatctcag ggccttgtcc     1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgaa aaagaccggc aagcgctcca ccagcgccgc cgtcctggag    1560 gcctccgcg aggcccaccc catcgtggag aagatcctgc agtacaagga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
```

```
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggaccccct gatgcgccgg    1980
gcggccaaga ccatcaactt cggggtcctc tacggcatgt cggcccaccg cctctcccag    2040
gagctagcca tcccttacga ggaggccag  gccttcattg agcgctactt tcagagcttc    2100
cccaaggtgc gggcctggat tgagaagacc ctggaggagg caggaggcg  ggggtacgtg    2160 gagaccctct tcggccgccg ccgctacgtg ccagacctag aggcccgggt gaagagcgtg    2220 cggggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg  tatcccctgg ccgtgccct  ggaggtggag    2460 gtggggatag ggaggactg  gctctccgcc aaggagtga                           2499

<210> SEQ ID NO 15
<211> LENGTH: 2499
<212> TYPE: DNA
<213> ORGANISM: Artificial
<220> FEATURE:
<223> OTHER INFORMATION: Taq E507K/R660V

<400> SEQUENCE: 15
atgaggggga tgctgcccct ctttgagccc aagggccggg tcctcctggt ggacggccac     60
cacctggcct accgcacctt ccacgccctg aagggcctca ccaccagccg gggggagccg    120
gtgcaggcgg tctacggctt cgccaagagc ctcctcaagg ccctcaagga ggacggggac    180
gcggtgatcg tggtctttga cgccaaggcc ccctccttcc gccacgaggc ctacggggg    240 tacaaggcgg gccggccc  cacgccggag gactttcccc ggcaactcgc cctcatcaag    300
gagctggtgg acctcctggg gctggcgcgc ctcgaggtcc cgggctacga ggcggacgac    360
gtcctggcca gcctggccaa gaaggcggaa aaggagggct acgaggtccg catcctcacc    420
gccgacaaag acctttacca gctcctttcc gaccgcatcc acgtcctcca ccccgagggg    480
tacctcatca cccccggcctg gctttgggaa aagtacggcc tgaggcccga ccagtgggcc    540
gactaccggg ccctgaccgg ggacgagtcc gacaaccttc ccgggtcaa  gggcatcggg    600 gagaagacgc gcaggaagct tctggaggag tggggcagcc tggaagccct cctcaagaac    660
ctggaccggc tgaagccgc  catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc ccctggccc     900 ccgccggaag gggccttcgt gggctttgtg ctttcccgca aggagcccat gtgggccgat    960
cttctggccc tggccgccgc caggggggc  cggtccacc  gggcccccga gccttataaa   1020
gccctcaggg acctgaagga ggcgggggg  cttctcgcca agaccctgag cgttctggcc   1080
ctgagggaag gccttggcct cccgcccggc gacgacccca tgctcctcgc ctacctcctg   1140 gaccctttcca acaccacccc cgagggggtg gccggcgct  acgggggga  gtggacggag   1200 gaggcgggg  agcgggccgc cctttccgag aggctcttcg ccaacctgtg ggggaggctt   1260 gaggggagg  agaggctcct ttggcttta  cgggaggtgg agaggcccct ttccgctgtc   1320
```

-continued

```
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg aaagggtcc tctttgacga gctagggctt     1500
cccgccatcg gcaagacgaa aaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct caaccagac ggccacggcc acgggcaggc taagtagctc cgatcccaac     1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccct gatgcgcgtg     1980 gcggccaaga ccatcaactt cggggtcctc tacggcatgt cggcccaccg cctctcccag    2040
gagctagcca tcccttacga ggaggccag gccttcattg agcgctactt tcagagcttc     2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agaggggcgga ggccgtggcc    2400 cggctggcca aggaggtcat ggagggggtg tatcccctgg ccgtgcccct ggaggtggag    2460
gtggggatag ggaggactg gctctccgcc aaggagtga                            2499
```

<210> SEQ ID NO 16
<211> LENGTH: 2499
<212> TYPE: DNA
<213> ORGANISM: Artificial
<220> FEATURE:
<223> OTHER INFORMATION: Taq E507K/R536K/R660V

<400> SEQUENCE: 16

```
atgagggga tgctgcccct cttttgagccc aagggccggg tcctcctggt ggacggccac     60
cacctggcct accgcacctt ccacgccctg aagggcctca ccaccagccg gggggagccg    120
gtgcaggcgg tctacggctt cgccaagagc ctcctcaagg ccctcaagga ggacggggac    180
gcggtgatcg tggtctttga cgccaaggcc ccctccttcc gccacgaggc ctacgggggg    240
tacaaggcgg gccggccccc cacgccggag gactttcccc ggcaactcgc cctcatcaag    300 gagctggtg acctcctggg gctggcgcgc tcgaggtccc cggctacga gcggacgac      360 gtcctggcca gctggccaa gaaggcgaaa aaggagggct acgaggtccg catcctcacc    420
gccgacaaag acctttacca gctcctttcc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaaccttc cggggtcaa gggcatcggg    600 gagaagacgg cgaggaagct tctggagag tgggggagcc tggaagccct cctcaagaac     660
ctggaccggc tgaagcccgc catccggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
```

```
ctcctccacg agttcggcct tctggaaagc cccaaggccc tggaggaggc ccctggccc    900
ccgccggaag gggccttcgt gggctttgtg ctttcccgca aggagcccat gtgggccgat    960
cttctggccc tggccgccgc cagggggggc cgggtccacc gggcccccga gccttataaa   1020
gccctcaggg acctgaagga ggcgcggggg cttctcgcca aagacctgag cgttctggcc   1080
ctgagggaag gccttggcct cccgcccggc gacgacccca tgctcctcgc ctacctcctg   1140
gaccctccca acaccacccc cgaggggtg gccggcgct acggcgggga gtggacggag    1200
gaggcggggg agcgggccgc cctttccgag aggctcttcg ccaacctgtg ggggaggctt   1260
gaggggggagg agaggctcct ttggctttac cgggaggtgg agaggcccct ttccgctgtc   1320
ctggcccaca tggaggccac ggggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgaa aaagaccggc aagcgctcca ccagcgccgc cgtcctggag   1560
gccctccgcg aggcccaccc catcgtggag aagatcctgc agtacaagga gctcaccaag   1620
ctgaagagca cctacattga ccccttgccg gacctcatcc accccaggac gggccgcctc   1680
cacacccgct tcaaccagac ggccacggcc acgggcaggc taagtagctc cgatcccaac   1740
ctccagaaca tccccgtccg caccccgctt gggcagagga tccgccgggc cttcatcgcc   1800
gaggaggggt ggctattggt ggccctggac tatagccaga tagagctcag ggtgctggcc   1860
cacctctccg gcgacgagaa cctgatccgg gtcttccagg aggggcggga catccacacg   1920
gagaccgcca gctggatgtt cggcgtcccc cgggaggccg tggacccct gatgcgcgtg   1980
gcggccaaga ccatcaactt cggggtcctc tacggcatgt cggcccaccg cctctcccag   2040
gagctagcca tcccttacga ggaggcccag gccttcattg agcgctactt tcagagcttc   2100
cccaaggtgc gggcctggat tgagaagacc ctggaggagg gcaggaggcg ggggtacgtg   2160
gagaccctct tcggccgccg ccgctacgtg ccagacctag aggcccgggt gaagagcgtg   2220
cgggaggcgg ccgagcgcat ggccttcaac atgcccgtcc agggcaccgc cgccgacctc   2280
atgaagctgg ctatggtgaa gctcttcccc aggctggagg aaatggggc caggatgctc   2340
cttcaggtcc acgacgagct ggtcctcgag gccccaaaag agagggcgga ggccgtggcc   2400
cggctggcca aggaggtcat ggagggggtg tatcccctgg ccgtgcccct ggaggtggag   2460
gtggggatag gggaggactg gctctccgcc aaggagtga                           2499

<210> SEQ ID NO 17
<211> LENGTH: 20
<212> TYPE: DNA
<213> ORGANISM: Artificial
<220> FEATURE:
<223> OTHER INFORMATION: Eco-forward primer

<400> SEQUENCE: 17
ggggtacctc atcaccccgg                                                 20

<210> SEQ ID NO 18
<211> LENGTH: 27
<212> TYPE: DNA
<213> ORGANISM: Artificial
<220> FEATURE:
<223> OTHER INFORMATION: R536K-reverse primer

<400> SEQUENCE: 18
cttggtgagc tccttgtact gcaggat                                         27
```

<210> SEQ ID NO 19
<211> LENGTH: 27
<212> TYPE: DNA
<213> ORGANISM: Artificial
<220> FEATURE:
<223> OTHER INFORMATION: R536K-forward primer

<400> SEQUENCE: 19
atcctgcagt acaaggagct caccaag                                       27

<210> SEQ ID NO 20
<211> LENGTH: 30
<212> TYPE: DNA
<213> ORGANISM: Artificial
<220> FEATURE:
<223> OTHER INFORMATION: R660V-reverse primer

<400> SEQUENCE: 20
gatggtcttg ccgccacgc gcatcagggg                                     30

<210> SEQ ID NO 21
<211> LENGTH: 30
<212> TYPE: DNA
<213> ORGANISM: Artificial
<220> FEATURE:
<223> OTHER INFORMATION: R660V-forward primer

<400> SEQUENCE: 21
cccctgatgc gcgtggcggc caagaccatc                                    30

<210> SEQ ID NO 22
<211> LENGTH: 32
<212> TYPE: DNA
<213> ORGANISM: Artificial
<220> FEATURE:
<223> OTHER INFORMATION: Xba-reverse primer

<400> SEQUENCE: 22
gctctagact atcactcctt ggcggagagc ca                                 32

<210> SEQ ID NO 23
<211> LENGTH: 27
<212> TYPE: DNA
<213> ORGANISM: Artificial
<220> FEATURE:
<223> OTHER INFORMATION: E507K-reverse primer

<400> SEQUENCE: 23
cttgccggtc tttttcgtct tgccgat                                       27

<210> SEQ ID NO 24
<211> LENGTH: 27
<212> TYPE: DNA
<213> ORGANISM: Artificial
<220> FEATURE:
<223> OTHER INFORMATION: E507K-forward primer

<400> SEQUENCE: 24
atcggcaaga cgaaaaagac cggcaag                                       27

<210> SEQ ID NO 25
<211> LENGTH: 25
<212> TYPE: DNA
<213> ORGANISM: Artificial
<220> FEATURE:

<223> OTHER INFORMATION: rs1408799 forward primer

<400> SEQUENCE: 25
ccagtgttag gttatttcta acttg 25

<210> SEQ ID NO 26
<211> LENGTH: 19
<212> TYPE: DNA
<213> ORGANISM: Artificial
<220> FEATURE:
<223> OTHER INFORMATION: rs1408799 reverse_T primer

<400> SEQUENCE: 26
gctcggagca catggtcaa 19

<210> SEQ ID NO 27
<211> LENGTH: 19
<212> TYPE: DNA
<213> ORGANISM: Artificial
<220> FEATURE:
<223> OTHER INFORMATION: rs1408799 reverse_C primer

<400> SEQUENCE: 27
gctcggagca catggtcag 19

<210> SEQ ID NO 28
<211> LENGTH: 22
<212> TYPE: DNA
<213> ORGANISM: Artificial
<220> FEATURE:
<223> OTHER INFORMATION: rs1015362 forward primer

<400> SEQUENCE: 28
tgaagagcag gaaagttctt ca 22

<210> SEQ ID NO 29
<211> LENGTH: 20
<212> TYPE: DNA
<213> ORGANISM: Artificial
<220> FEATURE:
<223> OTHER INFORMATION: rs1015362 reverse_C primer

<400> SEQUENCE: 29
actgtgtgtc tgaaacagtg 20

<210> SEQ ID NO 30
<211> LENGTH: 20
<212> TYPE: DNA
<213> ORGANISM: Artificial
<220> FEATURE:
<223> OTHER INFORMATION: rs1015362 reverse_T primer

<400> SEQUENCE: 30
actgtgtgtc tgaaacagta 20

<210> SEQ ID NO 31
<211> LENGTH: 26
<212> TYPE: DNA
<213> ORGANISM: Artificial
<220> FEATURE:
<223> OTHER INFORMATION: rs4911414 forward_G primer

<400> SEQUENCE: 31
gtaagtcttt gctgagaaat tcattg 26

```
<210> SEQ ID NO 32
<211> LENGTH: 26
<212> TYPE: DNA
<213> ORGANISM: Artificial
<220> FEATURE:
<223> OTHER INFORMATION: rs4911414 forward_T primer

<400> SEQUENCE: 32
gtaagtcttt gctgagaaat tcattt                                        26

<210> SEQ ID NO 33
<211> LENGTH: 23
<212> TYPE: DNA
<213> ORGANISM: Artificial
<220> FEATURE:
<223> OTHER INFORMATION: rs4911414 reverse primer

<400> SEQUENCE: 33
agtatccagg gttaatgtga aag                                           23

<210> SEQ ID NO 34
<211> LENGTH: 25
<212> TYPE: DNA
<213> ORGANISM: Artificial
<220> FEATURE:
<223> OTHER INFORMATION: 1408799-FAM probe

<400> SEQUENCE: 34
agatatttgt aaggtattct ggcct                                         25

<210> SEQ ID NO 35
<211> LENGTH: 24
<212> TYPE: DNA
<213> ORGANISM: Artificial
<220> FEATURE:
<223> OTHER INFORMATION: 1015362-HEX probe

<400> SEQUENCE: 35
tgctgaacaa atagtcccga ccag                                          24

<210> SEQ ID NO 36
<211> LENGTH: 24
<212> TYPE: DNA
<213> ORGANISM: Artificial
<220> FEATURE:
<223> OTHER INFORMATION: 4911414-Texas Red probe

<400> SEQUENCE: 36
tttctctagt tgcctttaag attt                                          24

<210> SEQ ID NO 37
<211> LENGTH: 832
<212> TYPE: PRT
<213> ORGANISM: Artificial
<220> FEATURE:
<223> OTHER INFORMATION: Taq E507K/R536K/R587I/R660V

<400> SEQUENCE: 37

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
```

```
            50                  55                  60
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
                275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
                450                 455                 460

Glu Glu Ile Ala Arg Leu Glu Ala Glu Val Phe Arg Leu Ala Gly His
465                 470                 475                 480
```

```
Pro Phe Asn Leu Asn Ser Arg Asp Gln Leu Glu Arg Val Leu Phe Asp
            485                 490                 495
Glu Leu Gly Leu Pro Ala Ile Gly Lys Glu Lys Thr Gly Lys Arg
        500                 505                 510
Ser Thr Ser Ala Ala Val Leu Glu Ala Leu Arg Glu Ala His Pro Ile
        515                 520                 525
Val Glu Lys Ile Leu Gln Tyr Lys Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Ile Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Val Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830

<210> SEQ ID NO 38
<211> LENGTH: 2499
<212> TYPE: DNA
<213> ORGANISM: Artificial
<220> FEATURE:
<223> OTHER INFORMATION: Taq E507K/R536K/R587I/R660V

<400> SEQUENCE: 38 atgagggga tgctgcccct ctttgagccc aagggccggg tcctcctggt ggacggccac    60
```

```
cacctggcct accgcaccttt ccacgccctg aagggcctca ccaccagccg gggggagccg    120
gtgcaggcgg tctacggctt cgccaagagc ctcctcaagg ccctcaagga ggacggggac    180
gcggtgatcg tggtctttga cgccaaggcc ccctccttcc gccacgaggc ctacgggggg    240
tacaaggcgg gccgggcccc cacgccggag gactttcccc ggcaactcgc cctcatcaag    300
gagctggtgg acctcctggg gctggcgcgc ctcgaggtcc cgggctacga ggcggacgac    360
gtcctggcca gctggccaa gaaggcggaa aaggagggct acgaggtccg catcctcacc    420
gccgacaaag acctttacca gctcctttcc gaccgcatcc acgtcctcca ccccgagggg    480
tacctcatca ccccgcctg gctttgggaa aagtacggcc tgaggcccga ccagtgggcc    540
gactaccggg ccctgaccgg ggacgagtcc gacaaccttc ccggggtcaa gggcatcggg    600
gagaagacgg cgaggaagct tctggaggag tgggggagcc tggaagccct cctcaagaac    660
ctggaccggc tgaagcccgc catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc cccctggccc    900
ccgccggaag gggccttcgt gggctttgtg ctttcccgca aggagcccat gtgggccgat    960
cttctggccc tggccgccgc caggggggggc cgggtccacc gggcccccga gccttataaa   1020
gccctcaggg acctgaagga ggcgcggggg cttctcgcca aagacctgag cgttctggcc   1080
ctgagggaag gccttggcct cccgccggc gacgaccca tgctcctcgc ctacctcctg   1140
gacccttcca acaccacccc cgaggggtg cccggcgct acggcgggga gtggacggag   1200
gaggcggggg agcgggccgc cctttccgag aggctcttcg ccaacctgtg ggggaggctt   1260 gaggggagg agaggctcct ttggctttac cggaggtgg agaggcccct ttccgctgtc   1320
ctggcccaca tggaggccac ggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgaa aaagaccggc aagcgctcca ccagcgccgc cgtcctggag   1560
gccctccgcg aggcccaccc catcgtggag aagatcctgc agtacaagga gctcaccaag   1620
ctgaagagca cctacattga ccccttgccg gacctcatcc accccaggac gggccgcctc   1680
cacacccgct tcaaccagac ggccacggcc acgggcaggc taagtagctc cgatcccaac   1740
ctccagaaca tccccgtcat caccccgctt gggcagagga tccgccgggc cttcatcgcc   1800
gaggaggggt ggctattggt ggccctggac tatagccaga tagagctcag ggtgctggcc   1860
cacctctccg gcgacgagaa cctgatccgg gtcttcagg aggggcggga catccacacg   1920
gagaccgcca gctggatgtt cggcgtcccc cgggaggccg tggaccccct gatgcgcgtg   1980
gcggccaaga ccatcaactt cggggtcctc tacggcatgt cggcccaccg cctctcccag   2040
gagctagcca tcccttacga ggaggcccag gccttcattg agcgctactt tcagagcttc   2100
cccaaggtgc gggcctggat tgagaagacc ctggaggagg caggaggcg ggggtacgtg   2160 gagaccctct tcgccgccg ccgctacgtg ccagacctag aggcccgggt gaagagcgtg   2220
cgggaggcgg ccgagcgcat ggccttcaac atgcccgtcc agggcaccgc cgccgacctc   2280
atgaagctgg ctatggtgaa gctcttcccc aggctggagg aaatgggggc caggatgctc   2340
cttcaggtcc acgacgagct ggtcctcgag gccccaaaag agagggcgga ggccgtggcc   2400
cggctggcca aggaggtcat ggagggggtg tatccctgg ccgtgccct ggaggtggag   2460
```

```
gtggggatag gggaggactg gctctccgcc aaggagtga                              2499
```

<210> SEQ ID NO 39
<211> LENGTH: 36
<212> TYPE: DNA
<213> ORGANISM: Artificial
<220> FEATURE:
<223> OTHER INFORMATION: Kpn-forward primer

<400> SEQUENCE: 39

```
tccaccccga ggggtacctc atcaccccgg cctggc                                36
```

<210> SEQ ID NO 40
<211> LENGTH: 27
<212> TYPE: DNA
<213> ORGANISM: Artificial
<220> FEATURE:
<223> OTHER INFORMATION: R587I-reverse primer

<400> SEQUENCE: 40

```
cccaagcggg gtgatgacgg ggatgtt                                          27
```

<210> SEQ ID NO 41
<211> LENGTH: 27
<212> TYPE: DNA
<213> ORGANISM: Artificial
<220> FEATURE:
<223> OTHER INFORMATION: R587I-forward primer

<400> SEQUENCE: 41

```
aacatccccg tcatcacccc gcttggg                                          27
```

<210> SEQ ID NO 42
<211> LENGTH: 37
<212> TYPE: DNA
<213> ORGANISM: Artificial
<220> FEATURE:
<223> OTHER INFORMATION: Xba-reverse primer

<400> SEQUENCE: 42

```
ctgcaggtcg actctagact atcactcctt ggcggag                               37
```

<210> SEQ ID NO 43
<211> LENGTH: 24
<212> TYPE: DNA
<213> ORGANISM: Artificial
<220> FEATURE:
<223> OTHER INFORMATION: KRAS Q61H forward_Q primer(24mer)

<400> SEQUENCE: 43

```
gatattctcg acacagcagg tcaa                                             24
```

<210> SEQ ID NO 44
<211> LENGTH: 24
<212> TYPE: DNA
<213> ORGANISM: Artificial
<220> FEATURE:
<223> OTHER INFORMATION: KRAS Q61H forward_H primer(24mer)

<400> SEQUENCE: 44

```
gatattctcg acacagcagg tcac                                             24
```

<210> SEQ ID NO 45
<211> LENGTH: 20
<212> TYPE: DNA

```
<213> ORGANISM: Artificial
<220> FEATURE:
<223> OTHER INFORMATION: KRAS Q61H reverse primer

<400> SEQUENCE: 45
acaaagaaag ccctccccag                                               20

<210> SEQ ID NO 46
<211> LENGTH: 25
<212> TYPE: DNA
<213> ORGANISM: Artificial
<220> FEATURE:
<223> OTHER INFORMATION: KRAS Q61H FAM probe

<400> SEQUENCE: 46
tgcaatgagg gaccagtaca tgagg                                         25

<210> SEQ ID NO 47
<211> LENGTH: 18
<212> TYPE: DNA
<213> ORGANISM: Artificial
<220> FEATURE:
<223> OTHER INFORMATION: KRAS Q61H forward_Q primer(18mer)

<400> SEQUENCE: 47
ctcgacacag caggtcaa                                                 18

<210> SEQ ID NO 48
<211> LENGTH: 18
<212> TYPE: DNA
<213> ORGANISM: Artificial
<220> FEATURE:
<223> OTHER INFORMATION: KRAS Q61H forward_H primer(18mer)

<400> SEQUENCE: 48
ctcgacacag caggtcac                                                 18

<210> SEQ ID NO 49
<211> LENGTH: 20
<212> TYPE: DNA
<213> ORGANISM: Artificial
<220> FEATURE:
<223> OTHER INFORMATION: KRAS Q61H reverse primer

<400> SEQUENCE: 49
acaaagaaag ccctccccag                                               20

<210> SEQ ID NO 50
<211> LENGTH: 21
<212> TYPE: DNA
<213> ORGANISM: Artificial
<220> FEATURE:
<223> OTHER INFORMATION: KRAS G13D forward primer

<400> SEQUENCE: 50
ataaggcctg ctgaaaatga c                                             21

<210> SEQ ID NO 51
<211> LENGTH: 17
<212> TYPE: DNA
<213> ORGANISM: Artificial
<220> FEATURE:
<223> OTHER INFORMATION: KRAS G13D reverse_G primer(17mer)

<400> SEQUENCE: 51
ggcactcttg cctacgc                                                  17
```

```
<210> SEQ ID NO 52
<211> LENGTH: 17
<212> TYPE: DNA
<213> ORGANISM: Artificial
<220> FEATURE:
<223> OTHER INFORMATION: KRAS G13D reverse_D primer(17mer)

<400> SEQUENCE: 52
ggcactcttg cctacgt                                                    17

<210> SEQ ID NO 53
<211> LENGTH: 30
<212> TYPE: DNA
<213> ORGANISM: Artificial
<220> FEATURE:
<223> OTHER INFORMATION: G1213_R FAM

<400> SEQUENCE: 53
agctccaact accacaagtt tatattcagt                                      30

<210> SEQ ID NO 54
<211> LENGTH: 23
<212> TYPE: DNA
<213> ORGANISM: Artificial
<220> FEATURE:
<223> OTHER INFORMATION: KRAS G12S forward_G primer(23mer)

<400> SEQUENCE: 54
taaacttgtg gtagttggag ctg                                             23

<210> SEQ ID NO 55
<211> LENGTH: 23
<212> TYPE: DNA
<213> ORGANISM: Artificial
<220> FEATURE:
<223> OTHER INFORMATION: KRAS G12S forward_S primer(23mer)

<400> SEQUENCE: 55
taaacttgtg gtagttggag cta                                             23

<210> SEQ ID NO 56
<211> LENGTH: 28
<212> TYPE: DNA
<213> ORGANISM: Artificial
<220> FEATURE:
<223> OTHER INFORMATION: KRAS G12S reverse primer

<400> SEQUENCE: 56
catattcgtc cacaaaatga ttctgaat                                        28

<210> SEQ ID NO 57
<211> LENGTH: 25
<212> TYPE: DNA
<213> ORGANISM: Artificial
<220> FEATURE:
<223> OTHER INFORMATION: G1213_F FAM probe

<400> SEQUENCE: 57
agctgtatcg tcaaggcact cttgc                                           25

<210> SEQ ID NO 58
<211> LENGTH: 20
<212> TYPE: DNA
<213> ORGANISM: Artificial
<220> FEATURE:
```

```
<223> OTHER INFORMATION: EGFR L858R forward primer

<400> SEQUENCE: 58
acctggcagc caggaacgta                                              20

<210> SEQ ID NO 59
<211> LENGTH: 19
<212> TYPE: DNA
<213> ORGANISM: Artificial
<220> FEATURE:
<223> OTHER INFORMATION: EGFR L858R reverse_L primer

<400> SEQUENCE: 59
gcacccagca gtttggcca                                               19

<210> SEQ ID NO 60
<211> LENGTH: 19
<212> TYPE: DNA
<213> ORGANISM: Artificial
<220> FEATURE:
<223> OTHER INFORMATION: EGFR L858R reverse_R primer

<400> SEQUENCE: 60
gcacccagca gtttggccc                                               19

<210> SEQ ID NO 61
<211> LENGTH: 28
<212> TYPE: DNA
<213> ORGANISM: Artificial
<220> FEATURE:
<223> OTHER INFORMATION: L858R FAM_R probe

<400> SEQUENCE: 61
cagcatgtca agatcacaga ttttgggc                                     28
```

DNA POLYMERASE WITH INCREASED GENE MUTATION SPECIFICITY

TECHNICAL FIELD

The present invention relates to a DNA polymerase with increased gene variation specificity and a PCR buffer composition for increasing the activity thereof, and more specifically, a DNA polymerase with increased gene variation specificity due to a mutation occurring at a specific amino acid position, a nucleic acid sequence encoding the polymerase, a vector including the nucleic acid sequence and a host cell transformed with the vector, a method of in vitro detecting one or more gene variations or SNPs in one or more templates using the DNA polymerase with increased gene variation specificity, a composition for detecting a gene variation or SNP, which includes the DNA polymerase, and a polymerase chain reaction (PCR) kit including the composition.

Moreover, the present invention provides a PCR buffer composition for increasing the activity of the DNA polymerase with increased gene variation specificity, a PCR kit for detecting a gene variation or SNP, which includes the PCR buffer composition and/or the DNA polymerase with increased gene variation specificity, and a method of in vitro detecting one or more gene variations or SNPs in one or more templates using the kit.

BACKGROUND ART

Since the first human genomic sequence has been defined, the inventors have focused on finding the genetic difference among individuals, such as single nucleotide polymorphisms (SNPs). SNPs in a genome are of interest because it is more and more clear that they are associated with different drug resistances or predisposing factors for various diseases. Due to the subsequent knowledge of medically-related nucleotide variation, a therapeutic method for the genetic supply of an individual may be applied, and a drug therapy which is ineffective or causes a side effect may be prevented. The development of technology that enables time- and cost-effective identification of nucleotide variation will bring further advances in pharmacogenetics.

SNPs account for the major genetic variations in a human genome and cause 90% or more of differences between individuals. To detect other nucleic acid variations such as the genetic variations and mutations, various methods may be used. For example, the identification of a variant of a target nucleic acid may be accomplished by hybridizing a nucleic acid sample to be analyzed with a hybridization primer specific for a sequence variant under suitable hybridization conditions.

However, it was found that such a hybridization method cannot satisfy clinical needs, particularly, in terms of sensitivity, which is required for an assay. Therefore, PCR has been extensively used in molecular biology and a diagnostic testing method for detecting mutations such as SNPs and other allelic sequence variants. Here, in consideration of the presence of a variant, a target nucleic acid to be tested was amplified by polymerase chain reaction (PCR) before hybridization. As a hybridization probe for the assay, generally, a single-stranded oligonucleotide is generally used. A modified embodiment of the assay includes a fluorescent hybridization probe. Generally, efforts have been made to automate methods of measuring SNPs and other sequence variations (Gut, Hum. Mutat. 17, 475-492 (2001)).

An alternative to sequence variation-specific hybridization known in the art is provided by so-called gene variation-specific amplification. In this detection method, during amplification, a variation-specific amplification primer is used, and generally has a so-called differential terminal nucleotide residue at the 3' end of the primer, where the residue is only complementary for one specific variation of a target nucleic acid to be detected. In this method, the nucleotide variant is measured by the presence or absence of a DNA product after PCR amplification. The principle of gene variation-specific amplification is based on the formation of a canonical or non-canonical primer-template complex at the end of a gene variation-specific amplification primer. Precisely, at the 3' end of the paired primer, amplification occurs by a DNA polymerase, but at the mismatched primer end, extension is suppressed.

For example, U.S. Pat. No. 5,595,890 discloses a method for gene variation-specific amplification and its application thereof, for example, the application to detect clinically associated point mutation in a k-ras tumor gene. In addition, U.S. Pat. No. 5,521,301 discloses an allele-specific amplification method for genotyping of an ABO blood group system. In contrast, U.S. Pat. No. 5,639,611 discloses the use of allele-specific amplification associated with the detection of a point mutation that causes sickle cell anemia. However, gene variation-specific amplification or allele-specific amplification is problematic in that it has low selectivity, and thus a more complicated and time- and cost-intensive optimizing step is needed.

Such a method for detecting sequence variations, polymorphisms and mainly point mutations requires allele-specific amplification (or gene variation-specific amplification) particularly when a sequence variation to be detected is deficient compared to dominant variations in the same nucleic acid fragment (or the same gene).

For example, this situation occurs when sporadic tumor cells are detected in the body fluid such as blood, serum or plasma by gene variation-specific amplification (U.S. Pat. No. 5,496,699). To this end, DNA is first isolated from the body fluid such as blood, serum or plasma, and DNA is derived from deficient, sporadic tumor cells and excessive non-proliferative cells. Thus, mutations that are significant to tumor DNA in the k-ras gene should be detected from several copies in the presence of an excessive amount of wild-type DNA.

All methods for gene variation-specific amplification disclosed in the prior art have the disadvantage that a 3'-terminal differential oligonucleotide residue should be used. In addition, despite the use of a 3'-differential nucleotide residue, these methods have the disadvantage that primer extension occurs at low levels in the presence of a suitable DNA polymerase even when a target nucleic acid is not exactly matched with a sequence variant to be detected. Particularly, when a specific sequence variant is detected by an excessive background nucleic acid including a different sequence variant, it leads to a false positive result. The main reason for the disadvantage of the PCR-based method is the incompatibility of a polymerase used in the method for sufficiently differentiating mismatched bases. Therefore, it is not yet possible to directly obtain clear data on the presence or absence of a mutation by PCR. To date, additional time- and cost-intensive purification and analysis methods have been required for the clear diagnosis of mutations. Therefore, a novel method for improving the selectivity of gene variation- or allele-specific PCR amplification will greatly affect the reliability and robustness of direct gene variation or SNP analysis by PCR.

Therefore, there are continuous demands for the development of a DNA polymerase with increased gene variation specificity and an optimal reaction buffer in which various materials are mixed to exhibit a proper function of the DNA polymerase.

The inventors had made efforts to develop a novel DNA polymerase that can improve the selectivity of gene variation-specific PCR amplification and a reaction buffer for increasing its activity, confirming that gene variation specificity significantly increased when a mutation occurs at an amino acid residue at a specific position of Taq polymerase, and the activity of the DNA polymerase with increased gene variation specificity increases when the concentration of KCl, $(NH_4)_2SO_4$ and/or tetra methyl ammonium chloride (TMAC) among the components of the PCR buffer composition is adjusted, and thus the present invention was completed.

DISCLOSURE

Technical Problem

The present invention is directed to providing a DNA polymerase for detecting one or more gene variations or SNPs in a target sequence having a gene variation or SNP.

The present invention is also directed to providing a nucleic acid sequence encoding the DNA polymerase according to the present invention, a vector including the nucleic acid sequence, and a host cell transformed with the vector.

The present invention is also directed to providing a method of preparing the DNA polymerase according to the present invention.

The present invention is also directed to providing a method of in vitro detecting one or more gene variations or SNPs in one or more templates using the DNA polymerase of the present invention.

The present invention is also directed to providing a composition for detecting a gene variation or SNP, which includes the DNA polymerase of the present invention.

The present invention is also directed to providing a kit for detecting the DNA polymerase of the present invention, which includes the composition for detecting a gene variation or SNP according to the present invention.

The present invention is also directed to providing a PCR buffer composition for increasing the activity of a DNA polymerase with increased gene variation specificity.

The present invention is also directed to providing a PCR kit for detecting a gene variation or SNP, which includes the PCR buffer composition and/or the DNA polymerase with increased gene variation specificity according to the present invention.

The present invention is also directed to providing a method of in vitro detecting one or more gene variations or SNPs in one or more templates using the PCR kit according to the present invention.

Technical Solution

One aspect of the present invention provides a DNA polymerase comprising a Taq polymerase amino acid sequence of SEQ ID NO: 1, the DNA polymerase including:
 (a) a substitution at amino acid residue 507 in the amino acid sequence of SEQ ID NO: 1; and
 (b) (i) a substitution at amino acid residue 536 in the amino acid sequence of SEQ ID NO: 1,
 (ii) a substitution at amino acid residue 660 in the amino acid sequence of SEQ ID NO: 1,
 (iii) substitutions at amino acid residues 536 and 660 in the amino acid sequence of SEQ ID NO: 1, or
 (iv) substitutions at amino acid residues 536, 587 and 660 in the amino acid sequence of SEQ ID NO: 1.

According to an exemplary embodiment of the present invention, the substitution at the amino acid residue 507 may be a substitution of glutamic acid (E) with lysine (K), the substitution at the amino acid residue 536 is a substitution of arginine (R) with lysine (K), the substitution at the amino acid residue 587 is a substitution of arginine (R) with isoleucine (I), and the substitution at the amino acid residue 660 is a substitution of arginine (R) with valine (V).

According to another exemplary embodiment of the present invention, the DNA polymerase may discriminate a matched primer from a mismatched primer, wherein the matched primer may be hybridized with the target sequence, and the mismatched primer may have a non-canonical nucleotide at the 3' end thereof with respect to the hybridized target sequence.

According to still another exemplary embodiment of the present invention, the DNA polymerase may exhibit a Ct value lower than the amplification of the target sequence comprising the mismatched primer.

Another aspect of the present invention provides a nucleic acid sequence encoding the DNA polymerase according to the present invention, a vector including the nucleic acid sequence, and a host cell transformed with the vector.

Still another aspect of the present invention provides a method of preparing a DNA polymerase, which includes: culturing the host cells; and isolating a DNA polymerase from the cell culture and a supernatant thereof.

Yet another aspect of the present invention provides a method of in vitro detecting one or more gene variations or SNPs in one or more templates, the method including:
 bringing the DNA polymerase according to the present invention into contact with a) one or more templates;
 b) one or more matched primers, one or more mismatched primers or both of one or more matched primers and one or more mismatched primers; and
 c) a nucleoside triphosphate,
 wherein the one or more matched primers and the one or more mismatched primers are hybridized with a target sequence, and the mismatched primer has a non-canonical nucleotide at base position 7 from the 3' end thereof with respect to the hybridized target sequence.

According to an exemplary embodiment of the present invention, the method may include a melting point analysis using a double strand-specific dye.

According to another exemplary embodiment of the present invention, the method may be accomplished by real-time PCR, the analysis on agarose gel after standard PCR, gene variation-specific amplification or allele-specific amplification through real-time PCR, tetra-primer amplification-refractory mutation system PCR or isothermal amplification.

Yet another aspect of the present invention provides a composition for detecting a gene variation or SNP, comprising the DNA polymerase according to the present invention.

Yet another aspect of the present invention provides a PCR kit including the composition for detecting a gene variation or SNP.

According to one exemplary embodiment of the present invention, the PCR kit may be used in competitive allele-specific TaqMan PCR (cast PCR), droplet digital PCR or MassARRAY.

According to another exemplary embodiment of the present invention, the PCR kit may further include one or more matched primers, one or more mismatched primers or both of one or more matched primers and one or more mismatched primers, where the one or more matched primers and the one or more mismatched primers may be hybridized with a target sequence, and the mismatched primer may have a non-canonical nucleotide at base position 7 from the 3' end thereof with respect to the hybridized target sequence.

According to still another exemplary embodiment of the present invention, the PCR kit may further include a nucleoside triphosphate.

According to yet another exemplary embodiment of the present invention, the PCR kit may further include
a) one or more buffers;
b) a quantification reagent binding to double-stranded DNA;
c) a polymerase blocking antibody;
d) one or more control values or control sequences; and
e) one or more templates.

Yet another aspect of the present invention provides a PCR buffer composition for increasing the activity of a DNA polymerase with increased gene variation specificity, which includes 25 to 100 mM KCl; and 1 to 15 mM $(NH_4)_2SO_4$, wherein the final pH is 8.0 to 9.0.

According to one exemplary embodiment of the present invention, the KCl concentration may be 60 to 90 mM.

According to another exemplary embodiment of the present invention, the $(NH_4)_2SO_4$ concentration may be 2 to 8 mM.

According to still another exemplary embodiment of the present invention, the KCl concentration may be 70 to 80 mM, and the $(NIH4)_2SO_4$ concentration may be 4 to 6 mM.

Yet another aspect of the present invention provides a PCR buffer composition for increasing the activity of a DNA polymerase with increased gene variation specificity, which includes 5 to 80 mM TMAC in the above-described PCR buffer composition.

According to one exemplary embodiment of the present invention, the KCl concentration may be 40 to 90 mM.

According to another exemplary embodiment of the present invention, the $(NH_4)_2SO_4$ concentration may be 1 to 7 mM.

According to still another exemplary embodiment of the present invention, the TMAC concentration may be 15 to 70 mM, the KCl concentration may be 50 to 80 mM, and the $(NH_4)_2SO_4$ concentration may be 1.5 to 6 mM.

According to yet another exemplary embodiment of the present invention, the PCR buffer composition may further include Tris·Cl and $MgCl_2$.

Yet another aspect of the present invention provides a PCR kit for detecting a gene variation or SNP, which includes the above-described PCR buffer composition.

According to one exemplary embodiment of the present invention, the PCR kit may include a DNA polymerase comprising a Taq polymerase amino acid sequence of SEQ ID NO: 1, where the DNA polymerase has the substitution(s) of the following amino acids:
(a) a substitution at amino acid residue 507 in the amino acid sequence of SEQ ID NO: 1; and
(b) (i) a substitution at amino acid residue 536 in the amino acid sequence of SEQ ID NO: 1,
(ii) a substitution at amino acid residue 660 in the amino acid sequence of SEQ ID NO: 1,
(iii) substitutions at amino acid residues 536 and 660 in the amino acid sequence of SEQ ID NO: 1, or
(iv) substitutions at amino acid residues 536, 587 and 660 in the amino acid sequence of SEQ ID NO: 1.

According to another exemplary embodiment of the present invention, the substitution at the amino acid residue 507 may be a substitution of glutamic acid (E) with lysine (K), the substitution at the amino acid residue 536 may be a substitution of arginine (R) with lysine (K), the substitution at the amino acid residue 587 may be a substitution of arginine (R) with isoleucine (I), and the substitution at the amino acid residue 660 may be a substitution of arginine (R) with valine (V).

According to still another exemplary embodiment of the present invention, the PCR kit may further include a) a nucleoside triphosphate; b) a quantification reagent binding to double-stranded DNA; c) a polymerase blocking antibody, d) one or more control values or control sequences; and e) one or more templates.

Yet another aspect of the present invention provides a method of in vitro detecting one or more gene variations or SNPs in one or more templates using the PCR kit of the present invention.

Advantageous Effects

Since the DNA polymerase with increased gene variation specificity according to the present invention has a higher mismatch-to-match extension selectivity than conventional Taq polymerase, reliable gene variation-specific amplification is possible without any substrate modification. The present invention also provides an optimal PCR buffer composition that allows the proper function of a DNA polymerase with increased gene variation specificity to be effectively exhibited, and reliable gene variation-specific amplification is possible by considerably increasing the activity of the DNA polymerase using the DNA polymerase with increased gene variation specificity. Moreover, a kit including a PCR buffer composition and/or the DNA polymerase with increased gene variation specificity according to the present invention can effectively detect a gene variation or SNP, and thus can be usefully applied to the medical diagnosis of a disease and recombinant DNA studies.

DESCRIPTION OF DRAWINGS

FIGS. 10a to 10d show the results of AS-qPCR for a template having an SNP of Q61H in a KRAS gene using a E507K/R536K/R587I/R660V polymerase, wherein FIGS. 10a and 10b show the results obtained using a 24-mer long primer, FIGS. 10c and 10d show the results obtained using a 18-mer long primer, and Taq polymerase having E507K/R536K/R660V variations is used as a control.

MODES OF THE INVENTION

Figure 1:
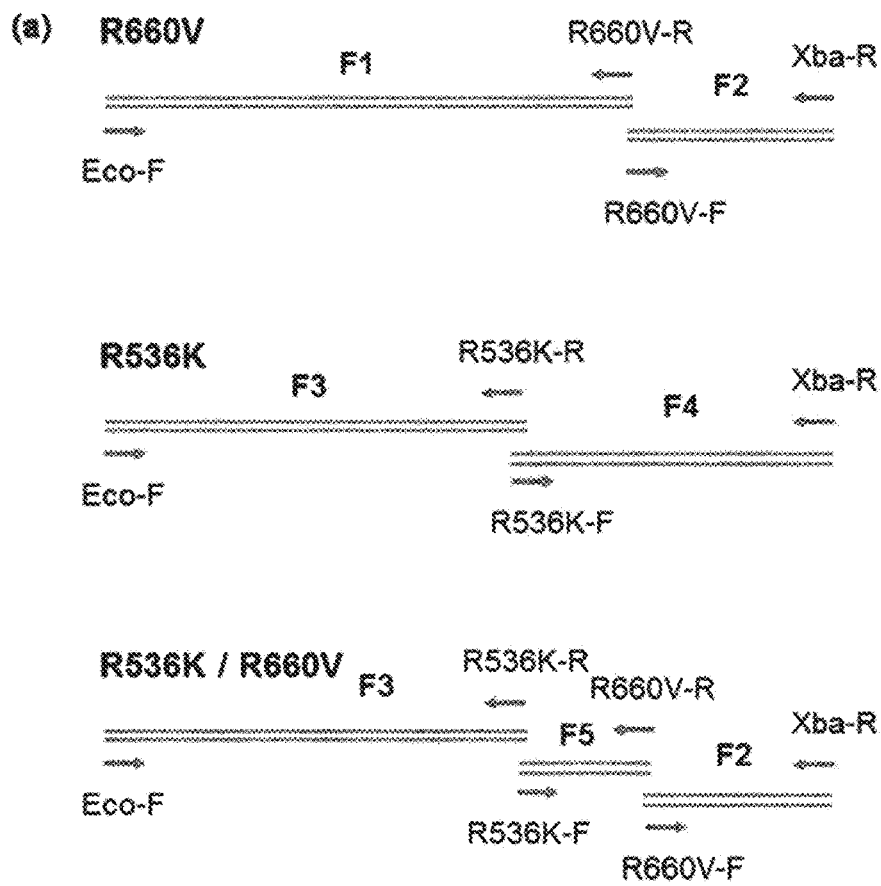
FIG. 1 shows a process of preparing Taq DNA polymerases having R536K, R660V and R536K/R660V variations: (a) the schematic representation of fragment PCR and overlap PCR; (b) the result of electrophoresis for amplified products obtained by the fragment PCR; and (c) the result of electrophoresis for amplified products obtained by full-length amplification through overlap PCR.
Figure 1:
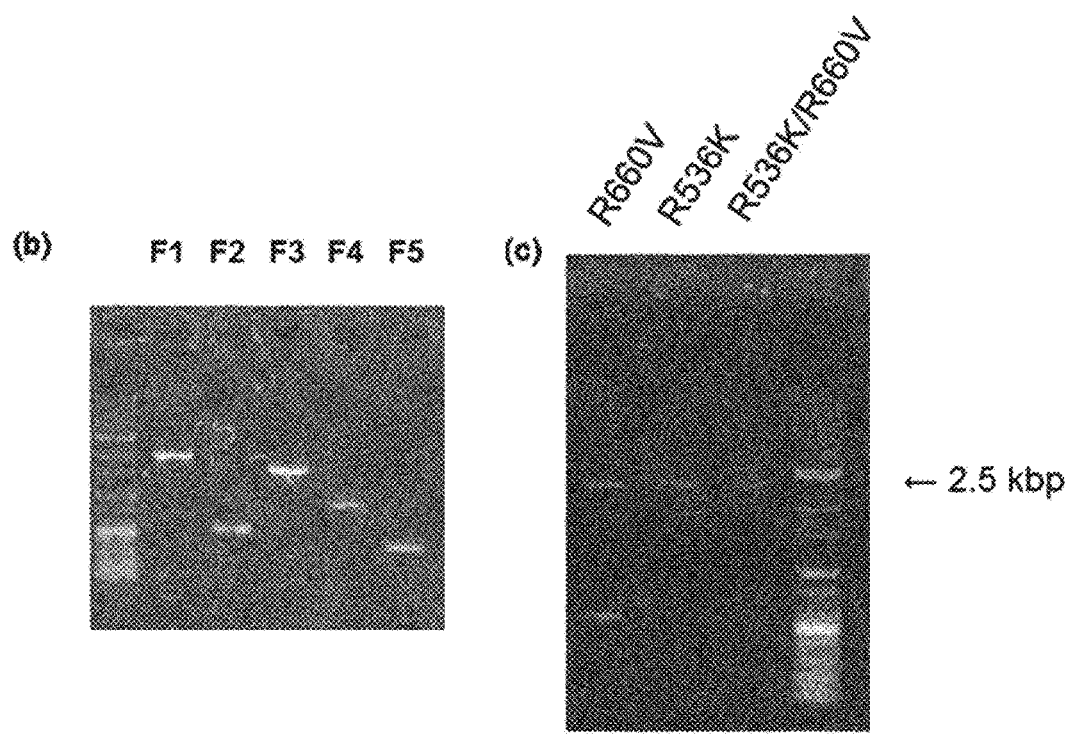

Hereinafter, the present invention will be described in further detail.

As described above, to improve the disadvantages of the gene variation-specific amplification method disclosed in the conventional art, there is a continuous demand for the development of a DNA polymerase with increased gene variation specificity and an optimal reaction buffer in which various materials are mixed such that the DNA polymerase can exhibit the proper function, and the development of such a method greatly affects the reliability and robustness of direct gene variation or SNP analysis by PCR. The inventors had made an effort to develop a novel DNA polymerase capable of improving the selectivity of gene variation-specific PCR amplification and a reaction buffer for increasing its activity, confirming that gene variation specificity significantly increased when a mutation occurs on an amino acid residue at a specific position of Taq polymerase, and the activity of the DNA polymerase with increased gene variation-specific amplification efficiency increases when the concentration of KCl, $(NH_4)_2SO_4$ and/or tetra methyl ammonium chloride (TMAC) among the components of the PCR buffer composition is adjusted, and thus the present invention was completed.

Since the DNA polymerase with increased gene variation specificity according to the present invention has a higher mismatch-to-match extension selectivity than conventional Taq polymerase, reliable gene variation-specific amplification is possible without any substrate modification. The present invention also provides an optimal PCR buffer composition that allows the proper function of a DNA polymerase with increased gene variation specificity to be effectively exhibited, and reliable gene variation-specific amplification is possible by considerably increasing the activity of the DNA polymerase using the DNA polymerase with increased gene variation specificity. Moreover, a kit including a PCR buffer composition and/or the DNA polymerase with increased gene variation specificity according to the present invention can effectively detect a gene variation or SNP, and thus can be usefully applied to the medical diagnosis of a disease and recombinant DNA studies.

Hereinafter, terms used herein will be defined.

The "amino acid" refers to any monomer unit that can be incorporated into a peptide, a polypeptide or a protein. The term "amino acid" used herein includes 20 natural or genetically encoded alpha-amino acids as follows: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or 1), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

Amino acids are typically organic acids, which substituted or unsubstituted amino groups, substituted or unsubstituted carboxyl groups, and one or more side chains or groups, or any analogs of these groups. Exemplary side chains include, for example, thiol, seleno, sulfonyl, alkyl, aryl, acyl, keto, azido, hydroxyl, hydrazine, cyano, halo, hydrazide, alkenyl, alkynyl, ether, borate, boronate, phospho, phosphono, phosphine, heterocyclic, enone, imine, aldehyde, ester, thioacid, hydroxylamine, or any combination thereof.

Other exemplary amino acids include the following amino acids, but the present invention is not limited thereto: an amino acid including a photoactivatable crosslinking agent, a metal-binding amino acid, a spin-labeled amino acid, a fluorescent amino acid, a metal-containing amino acid, a novel functional group-containing amino acid, an amino acid covalently or non-covalently interacting with another molecule, a photocaged and/or photoisomerizable amino acid, a radioactive amino acid, an amino acid including a biotin or biotin analog, a glycosylated amino acid, an amino acid modified with another carbohydrate, an amino acid including polyethylene glycol or polyether, a heavy atom-substituted amino acid, chemodegradable and/or photodegradable amino acid(s), a carbon-linked sugar-containing amino acid, a redox-active amino acid, an amino thioacid-containing amino acid, and an amino acid including one or more toxic parts.

Regarding the DNA polymerase of the present invention, the term "mutant" means a recombinant polypeptide including one or more amino acid substitutions, compared to a corresponding naturally-occurring or unmodified DNA polymerase.

The term "thermostable polymerase (referring to a thermostable enzyme)" has thermal resistance, has sufficient activity to achieve subsequent polynucleotide extension, and is not irreversibly denatured (inactivated) when treated at elevated temperatures for the time required to achieve the denaturation of a double-stranded nucleic acid. As used herein, it is suitable for a reaction such as PCR to be used at a cycling temperature. Herein, irreversible denaturation refers to the permanent and complete loss of enzyme activity. The enzyme activity of the thermostable polymerase refers to the catalysis of a nucleotide combination by a method suitable for the formation of a polynucleotide extension product which is complementary to a template nucleic acid strand. Thermophilic bacteria-derived thermostable DNA polymerases include, for example, DNA polymerases derived from *Hermotoga maritima, Thermus aquaticus, Thermus thermophilus, Thermus flabus, Thermodipyliporphis, Thermus* sp. Sps17, *Thermus* sp. Z05, *Thermus caldophilus, Bacillus caldotenax, Thermotoga neopolitanica* and *Thermosipo africanus*.

The term "thermoactive" refers to an enzyme maintaining a catalytic property at temperatures (i.e., 45 to 80° C.) conventionally used in reverse transcription or annealing/extension steps in RT-PCR and/or PCR reactions. The thermostable enzyme is not irreversibly inactivated or denatured when treated at elevated temperatures required for nucleic acid denaturation. The thermoactive enzyme may be thermostable or may not thermostable. The thermoactive DNA polymerase may include, but not limited to, DNA or RNA dependent on thermophilic or mesophilic species.

The term "host cell" includes single-cellular prokaryotic and eukaryotic organisms (e.g., bacteria, yeast, and actinomycetes) and single cells derived from higher plant, an animal, or both thereof.

The term "vector" refers to a DNA molecule which is replicable and able to deliver foreign DNA such as a gene to a recipient cell, for example, a plasmid, a phage, or an artificial chromosome. The "plasmid," "vector," or "plasmid vector" used herein may be used interchangeably.

The term "nucleotide" may be a deoxyribonucleic acid (DNA) or a ribonucleic acid (RNA), which is present in a single strand or double strand, and unless particularly described otherwise, an analog of a natural nucleotide may be included.

The term "nucleic acid" or "polynucleotide" refers to a DNA or RNA polymer, or a polymer that can correspond to an analog thereof. The nucleic acid may be, for example, a chromosome or chromosome fragment, a vector (e.g., an expression vector), an expression cassette, a naked DNA or RNA polymer, a product of a polymerase chain reaction (PCR), an oligonucleotide, a probe, or a primer, but the present invention is not limited thereto. The nucleic acid may be, for example, a single-stranded, double-stranded, or triple-stranded, but is not limited to any specific length. Unless particularly defined otherwise, a specific nucleic acid sequence includes a complementary sequence in addition to a random sequence noted herein, or encodes the same.

The "primer" refers to a polynucleotide that can serve as a starting point of nucleic acid synthesis in a template-direction under the conditions for the initiation of the extension of a polynucleotide. Primers may also be used in the process of synthesis mediated by various other oligonucleotides which are included as initiators of de novo RNA synthesis and an in vitro transcription-related process. Primers are typically single-stranded oligonucleotides (e.g., oligodeoxyribonucleotides). The suitable length of a primer varies typically in the range from 6 to 40 nucleotides, and more typically, 15 to 35 nucleotides, according to the intended use. A short primer molecule generally requires a lower temperature to form a sufficiently stable hybridization complex with a template. A primer is not required to correspond to the exact sequence of a template, but needs to be sufficiently complementary to be hybridized with the template subject to extension. In a specific exemplary embodiment, the term "primer pair" means a primer set comprising a 5'-sense primer which is complementarily hybridized to the 5' end of a nucleic acid sequence to be amplified, and a 3'-antisense primer which is hybridized to the 3' end of the sequence to be amplified. A primer may be labeled, if necessary, by being mixed with a marker to be detected by spectroscopic, photochemical, biochemical, immunochemical or chemical means. For example, a useful marker is as follows: 32P, a fluorescent dye, an electron-dense reagent, an enzyme (conventionally used in ELISA), biotin, or a protein that can be used with hapten and an anti-serum or monoclonal antibody.

The term "5'-nuclease probe" refers to an oligonucleotide having one or more luminescent markers which are used in a 5'-nuclease reaction for targeting nucleic acid detection. In some exemplary embodiments, for example, a 5'-nuclease probe only has a single luminescent part (e.g., a fluorescent dye or the like). In a specific exemplary embodiment, a 5-nuclease probe has a self-complementary region to form a hairpin structure under selective conditions. In some exemplary embodiments, a 5'-nuclease probe has two or more markers, and one of the two markers is separated or degraded from the oligonucleotide and then released with an increased radiation intensity. In a specific exemplary embodiment, a 5'-nuclease probe is labeled with two different fluorescent dyes, for example, a 5'-end reporter dye and a 3'-end quencher dye. In some exemplary embodiments, a 5'-nuclease probe is labeled at one or more positions in addition to or other than the ends. When the probe is intact, typically, energy transfer occurs between two fluorescent materials to partially or completely quench fluorescence emitted from a reporter dye. During extension in PCR, for example, a 5'-nuclease probe binding to a template nucleic acid is degraded by the activity of no longer quenching the fluorescence emission of a reporter dye, for example, the 5' or 3'-nuclease activity of Taq polymerase or a different polymerase. In some exemplary embodiments, a 5'-nuclease probe may be labeled with two or more different reporter dyes and a 3'-end quencher dye or a part thereof.

The term "FRET" or "fluorescence resonance energy transfer" or "Foerster Resonance Energy Transfer" refers to the transfer of energy between two or more chromophores, donor chromophores and recipient chromophores (referred to as quenchers). Typically, when a donor is excited by radiating light with an appropriate wavelength, energy is transferred to a recipient. The recipient typically re-radiates energy transferred in the form of light radiated with a different wavelength. When the recipient is a "dark" quencher, it disperses energy transferred in a form other than light. Whether a specific fluorescent material serves as a donor or recipient is dependent on the properties of other members of the FRET pair. Conventionally used donor-recipient pairs include a FAM-TAMRA pair. Conventionally used quenchers are DABCYL and TAMRA. Conventionally used dark quenchers are as follows: BlackHole Quenchers (BHQ), (Biosearch Technologies, Inc., Novato, Cal.), Iowa Black (Integrated DNA Tech., Inc., Coralville, Iowa), and BlackBerry Quencher 650 (BBQ-650) (Berry & Assoc., Dexter, Mich.).

The term "conventional" or "natural" used to describe a nucleic acid base, a nucleoside triphosphate or a nucleotide refers to those naturally occurring in the polynucleotides described herein (i.e., for DNA, dATP, dGTP, dCTP and dTTP). In addition, dTTP and 7-deaza-dGTP are frequently used instead of dGTP, and may be used instead of dATP in an in vitro DNA synthesis reaction such as sequencing.

The term "unconventional" or "modified" used to describe a nucleic acid base, a nucleoside triphosphate or a nucleotide refers to the modification, derivative or analog of a conventional base, nucleoside or nucleotide, which naturally occurs in a specific polynucleotide. A specific, unconventional nucleotide is modified at the 2' position of the ribose, compared with conventional dNTP. Therefore, although a nucleotide naturally occurring in RNA is a ribonucleotide (i.e., ATP, GTP, CTP, UTP, and collectively, rNTP), since the nucleotide has a hydroxyl group at the 2' position of the sugar, compared with dNTP having no hydroxyl group, as used herein, the ribonucleotide is a nucleotide which is not conventionally used as a substrate for a DNA polymerase. As used herein, an unconventional nucleotide includes a compound used as a terminator for nucleic acid sequencing, but the present invention is not limited thereto. An exemplary terminator compound includes a compound having a 2',3'-dideoxy structure, but the present invention is not limited thereto, and is referred to as a dideoxynucleoside triphosphate. Dideoxynucleoside triphosphates such as ddATP, ddTTP, ddCTP and ddGTP are collectively referred to as ddNTP. Additional examples of terminator compounds include 2'-PO4 analogs of a ribonucleotide. Other unconventional nucleotides include phosphorothioate dNTP ([[α]-S]dNTP), 5'-[α]-borano-dNTP, [α]-methyl-phosphonate dNTP, and ribonucleoside triphosphate (rNTP). An unconventional base may be labeled with a radioactive isotope, such as 32P, 33P, or 35S; a fluorescent marker, a chemoluminescent marker, a bioluminescent marker, a hapten marker such as biotin; or an enzyme marker such as streptavidin or avidin. A fluorescent marker may be a negatively-charged dye such as a fluorescein-family dye, or a neutrally-charged dye such as a rhodamine-family dye, or a positively-charged dye such as a cyanine-family dye. Fluorescein-family dyes include, for example, FAM, HEX, TET, JOE, NAN and ZOE. Rhodamine-family dyes include Texas Red, ROX, R110, R6G, and TAMRA. Various dyes or nucleotides labeled with FAM, HEX, TET, JOE, NAN, ZOE, ROX, R110. R6G, Texas Red and TAMRA are commercially available from Perkin-Elmer (Boston, MA), Applied Biosystems (Foster City, CA), or Invitrogen/Molecular Probes (Eugene, OR). Cyanine-family dyes include Cy2, Cy3, Cy5 and Cy7, and are commercially available from GE Healthcare UK Limited (Amersham Place, Little Chalfont, Buckinghamshire, England).

The term "mismatch discrimination" refers to the ability of a biocatalyst (e.g., an enzyme such as a polymerase, ligase, or the like) to discriminate a fully-complementary sequence from a mismatch-containing sequence when a nucleic acid (e.g., primer or a different oligonucleotide) is extended by attaching (for example, covalently) one or more nucleotides to the nucleic acid in a template-dependent manner. The term "mismatch discrimination" refers to the ability of a biocatalyst to discriminate a fully-complementary sequence from a mismatch-containing (approximately complementary) sequence, that is, an extended nucleic acid (e.g., a primer or different oligonucleotide) has a mismatch in the 3'-end nucleic acid, compared with a nucleic acid-hybridized template. In some exemplary embodiments, an extended nucleic acid includes a mismatch at the 3' end with respect to a fully-complementary sequence. In some exemplary embodiments, an extended nucleic acid includes a mismatch at the penultimate (N-1) 3' position and/or at the N-2 position relative to the fully complementary sequence.

Unless defined otherwise, all technical and scientific terms used herein have the same meanings as generally understood by those of ordinary skill in the art.

The present invention relates to a DNA polymerase comprising a Taq polymerase amino acid sequence of SEQ ID NO: 1, the DNA polymerase including
(a) a substitution at amino acid residue 507 in the amino acid sequence of SEQ ID NO: 1;
(b) (i) a substitution at amino acid residue 536 in the amino acid sequence of SEQ ID NO: 1,
(ii) a substitution at amino acid residue 660 in the amino acid sequence of SEQ ID NO: 1,
(iii) substitutions at amino acid residues 536 and 660 in the amino acid sequence of SEQ ID NO: 1, or
(iv) substitutions at amino acid residues 536, 587 and 660 in the amino acid sequence of SEQ ID NO: 1.

The "Taq polymerase" is a heat-resistant DNA polymerase named after thermophilic bacteria *Thermus aquaticus*, and was first isolated from the bacteria. *Thermus aquaticus* are bacteria living in hot springs and hydrothermal vents, and the Taq polymerase is an enzyme that can tolerate a protein-denaturing condition (high temperature) required during PCR. The Taq polymerase has an optimal activity temperature of 75 to 80° C., has a half-life of 2 hours or more at 92.5° C., 40 minutes at 95° C. and 9 minutes at 97.5° C., and can replicate 1000-bp DNA within 10 seconds at 72° C. It lacks 3'-5' exonuclease proofreading activity, resulting in an error rate of approximately 1 in 9,000 nucleotides. For example, when heat-resistant Taq is used, PCR may be performed at a high temperature (60° C. or more). The amino acid sequence set forth in SEQ ID NO: 1 is used as a reference sequence for the Taq polymerase.

According to an exemplary embodiment of the present invention, the substitution at amino acid residue 507 is a substitution of glutamic acid (E) with lysine (K), the substitution at amino acid residue 536 is a substitution of arginine (R) with lysine (K), the substitution at amino acid residue 587 is a substitution of arginine (R) with isoleucine (I), and the substitution at amino acid residue 660 may be a substitution of arginine (R) with valine (V).

In the present invention, the Taq polymerase in which glutamic acid (E) is substituted with lysine (K) at the amino acid residue 507 in the amino acid sequence of SEQ ID NO: 1 is named "E507K" (SEQ ID NO: 2); the Taq polymerase in which glutamic acid (E) is substituted with lysine (K) at the amino acid residue 507, and arginine (R) is substituted with lysine (K) at the amino acid residue 536 in the amino acid sequence of SEQ ID NO: 1 is named "E507K/R536K"

(SEQ ID NO: 6); the Taq polymerase in which glutamic acid (E) is substituted with lysine (K) at the amino acid residue 507, and arginine (R) is substituted with valine (V) at the amino acid residue 660 in the amino acid sequence of SEQ ID NO: 1 is named "E507K/R660V" (SEQ ID NO: 7); the Taq polymerase in which glutamic acid (E) is substituted with lysine (K) at the amino acid residue 507, arginine (R) is substituted with lysine (K) at the amino acid residue 536, and arginine (R) is substituted with valine (V) at the amino acid residue 660 in the amino acid sequence of SEQ ID NO: 1 is named "E507K/R536K/R660V" (SEQ ID NO: 8); and finally the Taq polymerase in which glutamic acid (E) is substituted with lysine (K) at the amino acid residue 507, arginine (R) is substituted with lysine (K) at the amino acid residue 536, arginine (R) is substituted with isoleucine (I) at the amino acid residue 587, and arginine (R) is substituted with valine (V) at the amino acid residue 660 in the amino acid sequence of SEQ ID NO: 1 is named "E507K/R536K/R587I/R660V" (SEQ ID NO: 37).

According to an exemplary embodiment of the present invention, the DNA polymerase discriminates a matched primer from a mismatched primer, the matched primer and the mismatched primer are hybridized with a target sequence, and the mismatched primer may include a non-canonical nucleotide at the 3' end with respect to a hybridized target sequence.

The mismatched primer is a hybrid oligonucleotide which should be sufficiently complementary to be hybridized with the target sequence, but does not correspond to the exact sequence of the target sequence.

The "canonical nucleotide" or "complementary nucleotide" means a standard Watson-Crick base pair, A-U, A-T or G-C.

The "non-canonical nucleotide" or "non-complementary nucleotide" means A-C, A-G, G-U, G-T, T-C, T-U, A-A, G-G, T-T, U-U, C-C, or C-U other than the Watson-Crick base pairs.

According to an exemplary embodiment of the present invention, with the DNA polymerase, the amplification of a target sequence including a matched primer may exhibit a lower Ct value than the amplification of a target sequence including a mismatched primer.

For example, the DNA polymerase may allow one or more nucleotides to covalently bind to a primer, thereby extending a matched primer with greater efficiency than a mismatched primer in a target sequence-dependent manner. Here, greater efficiency may be observed at a lower Ct value for a matched primer, compared with the mismatched primer, for example, in RT-PCR. The difference in Ct value between the matched primer and the mismatched primer may be 10 or more, and preferably, 10 to 20, or there may be no synthesis of an amplicon by a mismatched primer.

For example, such a difference means that a product formed by standard PCR using a forward primer and a reverse primer, which are matched in a first reaction, and a reverse primer matched with a mismatched forward primer in a second reaction with the same experiment settings is larger in the first reaction than in the second reaction.

A Ct (threshold crossing cycle) value represents a DNA quantification method by quantitative PCR, which depends on plotting the fluorescence representing the number of cycles on a log scale. The threshold for DNA-based fluorescence detection is set slightly higher than the minimum background. The number of cycles required for fluorescence to cross the threshold is called Ct or a quantification cycle (Cq) following the MIQE guidelines. The Ct value for the given reaction is defined as the number of cycles required for fluorescence emission to cross a fixed threshold. For example, SYBR Green I and a fluorescent probe may be used in real-time PCR for template DNA quantification. Fluorescence emitted from a sample is collected every cycle during PCR, and plotted against the number of cycles. A starting template concentration is inversely proportional to the time at which the fluorescent signal is first shown. The signal appears earlier as a template concentration is higher (shown at a low number of cycles).

The present invention also relates to a nucleic acid sequence encoding the above-described DNA polymerase, and a vector and a host cell, which include the nucleic acid sequence. Various vectors may be prepared using the nucleic acid encoding the DNA polymerase of the present invention. Any vector having a replicon and a control sequence, which are derived from a species compatible with a host cell, may be used. The vector of the present invention may be an expression vector, and has nucleic acid regions for regulating transcription and translation, which are operably linked to the nucleic acid sequence encoding the DNA polymerase of the present invention. The regulatory sequence refers to a DNA sequence required for the expression of a coding sequence operably linked to a specific host organism. For example, a control sequence suitable for a prokaryote includes a promoter, any operating sequence and a ribosome binding sequence. In addition, a vector may include a "positive retroregulatory element (PRE)" to increase the half-life of mRNA to be transcribed. Transcription and translation regulatory nucleic acid regions may be generally suitable for host cells used to express a polymerase. Various types of suitable expression vectors and regulatory sequences are known to be used for various host cells. Generally, transcription and translation regulatory sequences may include, for example, a promoter sequence, a ribosome binding site, transcription initiation and termination sequences, translation initiation and termination sequences, and an enhancer or activation sequence. In a typical, exemplary embodiment, regulatory sequences include a promoter and transcription initiation and termination sequences. Typically, a vector also includes a polylinker region containing several restriction sites for inserting foreign DNA. In a specific exemplary embodiment, the "fusion flag" is used to promote purification, and if necessary, a tag/flag is subsequently removed (e.g., "His-Tag"). However, when thermoactive and/or thermostable protein(s) is(are) purified from mesophilic hosts (e.g., E. coli) using a "heating step," the fusion flags are generally unnecessary. A suitable vector containing a DNA encoding replication sequence, a regulatory sequence and a phenotype selection gene is constructed, and a mutant polymerase of interest is prepared using a standard recombinant DNA technique. An isolated plasmid, a viral vector and a DNA fragment are digested and cleaved, and then ligated with each other in a specific order to form a desired vector as known in the art.

In an exemplary embodiment of the present invention, an expression vector contains a selectable marker gene to select a transformed host cell. Selection genes are known in the art, and may vary according to the host cells used herein. Suitable selection genes may include the gene coding for ampicillin and/or tetracycline resistance, and may allow cells in which these vectors are cultured in the presence of these antibiotics to be transformed.

In an exemplary embodiment of the present invention, a nucleic acid sequence encoding the DNA polymerase of the present invention may be introduced into cells alone or in combination with a vector. The introduction or equivalent expressions thereof refer to a nucleic acid entering cells in the method suitable for subsequent integration, amplification and/or expression. The introduction method includes, for example, CaPO$_4$ precipitation, liposome fusion, LIPOFEC-TIN®, electrophoresis, and viral infection.

Prokaryotes are used as host cells in an early cloning step of the present invention. They are particularly useful for rapidly preparing a great quantity of DNA, for preparing a single-stranded DNA template used in site-directed mutagenesis, for simultaneously screening many mutants, and for DNA sequencing of generated mutants. Suitable prokaryotic host cells include E. coli K12 strain 94 (ATCC No. 31,446), E. coli strain W3110 (ATCC No. 27,325), E. coli K12 strain DG116 (ATCC No. 53,606), E. coli X1776 (ATCC No. 31,537), and E. coli B; many other strains of E. coli, such as HB101, JM101, NM522, NM538 and NM539, and other species such as Bacilli, e.g., Bacillus subtilis, other Enterobacteriaceae, e.g., Salmonella typhimurium or Serratia marcescens, and prokaryotic genera including various Pseudomonas sp. may be used as hosts. Typically, plasmids used in the transformation of E. coli include pBR322, pUCI8, pUCI9, pUCI18, pUC119 and Bluescript M13. However, many other suitable vectors may also be used.

The present invention also provides a method of preparing a DNA polymerase, which includes: culturing the host cells; and isolating a DNA polymerase from a cell culture and a supernatant thereof.

The DNA polymerase of the present invention is prepared by culturing host cells transformed with an expression vector containing a nucleic acid sequence encoding the DNA polymerase under suitable conditions inducing or causing the expression of the DNA polymerase. A method of culturing the transformed host cells under conditions suitable for protein expression is known in the art. Host cells suitable for the preparation of a polymerase from a lambda (λ) µL promoter-containing plasmid vector include E. coli strain DG116 (ATCC No. 53606). When expressed, the polymerase may be collected and isolated.

After purification, mismatch discrimination of the DNA polymerase of the present invention may be assayed. For example, mismatch discrimination activity is measured by comparing the amplification of a target sequence perfectly matched with a primer with respect to the amplification of a target having a single base mismatch at the 3' end of a primer. The amplification may be detected in real time by using, for example, a TaqMan™ probe. The ability of a polymerase to distinguish between two target sequences may be assumed by comparing Cts in two reactions.

Therefore, the present invention provides a method of in vitro detecting one or more gene variations or SNPs in one or more templates, the method including:
  bringing the DNA polymerase according to the present invention into contact with a) one or more templates,
  b) a nucleoside triphosphate, and
  c) one or more matched primers, one or more mismatched primers or both of one or more matched primers and one or more mismatched primers, wherein the one or more matched primers and the one or more mismatched primers are hybridized with a target sequence, and the mismatched primer has a non-canonical nucleotide at base position 7 from the 3' end thereof with respect to the hybridized target sequence.

The "single-nucleotide polymorphism (SNP)" refers to a genetic change or variation showing the difference of a single base (A, T, G or C) in a DNA base sequence.

In the method of in vitro detecting a gene variation or SNP, a target sequence may be present in a test sample, including, for example, DNA, cDNA or RNA, and preferably, genomic DNA. The test sample may be a cell lysate prepared from bacteria, a bacterial culture, or a cell culture. In addition, the test sample may be one included in an animal, preferably, a vertebrate, and more preferably, a human subject. The target sequence may be genomic DNA, preferably, genomic DNA of an individual, more preferably, bacteria or a vertebrate, and most preferably, genomic DNA of a human subject.

The SNP detection method of the present invention may include analysis of a melting temperature using a double strand-specific dye such as SYBR Green I.

The analysis of a melting temperature curve may be performed in a real-time PCR instrument such as ABI 5700/7000 (96-well format) or ABI 7900 (384-well format) instrument with onboard software (SDS 2.1). Alternatively, the analysis of a melting temperature curve may be performed as end-point analysis.

The "dye binding to double-stranded DNA" or "double strand-specific dye" may be used when high fluorescence is emitted while binding to double-stranded DNA, rather than in an unbound state. Examples of these dyes are SOYTO-9, SOYTO-13, SOYTO-16, SOYTO-60, SOYTO-64, SOYTO-82, ethidium bromide (EtBr), SYTOX Orange, TO-PRO-1, SYBR Green I, TO-PRO-3 or EvaGreen. These dyes excluding EtBr and EvaGreen (Qiagen) have been tested in real-time applications.

The method of in vitro detecting a gene variation or SNP may be performed by real-time PCR, analysis on agarose gel after standard PCR, gene variation-specific amplification or allele-specific amplification through real-time PCR, tetra-primer amplification-refractory mutation system PCR or isothermal amplification, but the present invention is not limited thereto.

For example, the SNP detection method of the present invention may be performed using sequencing, mini-sequencing, allele-specific PCR, dynamic allele-specific hybridization (DASH), a PCR extension assay (e.g., single base extension; SBE), PCR-SSCP, a PCR-RFLP assay or TaqMan method, SNPlex platform (Applied Biosystems), mass spectrometry (e.g., MassARRAY system of Sequenom), or a Bio-Plex system (BioRad).

The "standard PCR" is a technique for amplifying single or several copies of DNA or cDNA known to a technician of ordinary skill in the art. Almost all PCR techniques use a thermostable DNA polymerase such as Taq polymerase or Klen Taq. A DNA polymerase uses single-stranded DNA as a template, and enzymatically assembles a new DNA strand from nucleotides using oligonucleotide primers. Amplicons generated by PCR may be analyzed on, for example, agarose gel.

The "real-time PCR" may monitor a PCR process in real time. Therefore, data is collected throughout the PCR process, not at the end of PCR. In the real-time PCR, the reaction is characterized by the point of time during a cycle when amplification is first detected, rather than the amount of a target accumulated after a fixed number of cycles. Usually, both of dye-based detection and probe-based detection are used to perform quantitative PCR.

The "allele-specific amplification (ASA)" is an amplification technique for designing PCR primers to discriminate templates with different single nucleotide residues.

The "allele-specific amplification or gene variation-specific amplification through real-time PCR" is a highly effective method for detecting a gene variation or SNP. Unlike most of other methods for detecting a gene variation or SNP, the pre-amplification of a target gene material is not needed. ASA combines amplification and detection in a single reaction based on the discrimination between matched and mismatched primer/target sequence complex. The increase in amplified DNA during the reaction may be monitored in real time with the increase in fluorescent signal caused by a dye such as SYBR Green I emitted upon binding to double-stranded DNA. The allele-specific amplification or gene variation-specific amplification through real-time PCR shows the delay or absence of a fluorescent signal when a primer is mismatched. In the gene variation or SNP detection, such amplification provides information on the presence or absence of a gene variation or SNP.

The "tetra-primer amplification-refractory mutation system PCR" is amplification of all of wild-type and mutant alleles with a control fragment in single tube PCR. A non-allele-specific control amplicon is amplified by two common (outside) primers flanking a mutation region. The two allele-specific (inside) primers are designed in an opposite direction to the common primers, both of wild-type and mutant amplicons may be simultaneously amplified with the common primers. As a result, two allele-specific amplicons may have different lengths since mutations are asymmetrically located based on the common (outside) primers, and easily separated by standard gel electrophoresis. The control amplicons provide an internal control for false negative results as well as amplification failure, and at least one of the two allele-specific amplicons is always present in the tetra-primer amplification-refractory mutation system PCR.

The "isothermal amplification" means that the amplification of a nucleic acid is not dependent on a thermocycler and is performed at a lower temperature without the need for temperature change during amplification. The temperature used in isothermal amplification may range from room temperature (22 to 24° C.) to approximately 65° C., or approximately 60 to 65° C., 45 to 50° C., 37 to 42° C. or room temperature (22 to 24° C.). A product obtained by the isothermal amplification may be detected by gel electrophoresis, ELISA, enzyme-linked oligosorbent assay (ELOSA), real-time PCR, enhanced chemiluminescence (ECL), a chip-based capillary electrophoresis device, such as a bioanalyzer, for analyzing RNA, DNA and protein or turbidity.

In an exemplary embodiment of the present invention, E507K/R536K, E507K/R660V, or E507K/R536K/R660V Taq polymerase was used to confirm whether an ability of extending a mismatched primer with respect to a template including a SNP (rs1408799, rs1015362 and/or rs4911414) was reduced.

As a result, as shown in FIGS. 6a-6d, 7 and 8, compared to E507K Taq polymerase, in the case of the E507K/R536K, E507K/R660V or E507K/R536K/R660V Taq polymerase, it can be confirmed that amplification with a mismatched primer is delayed, and such an effect was most clearly shown in the case of the E507K/R536K/R660V Taq polymerase.

To this end, it was confirmed that the three types of DNA polymerases have higher mismatch extension selectivity than the conventional Taq polymerase (E507K). Therefore, it is expected that the DNA polymerase of the present invention can be effectively used in medical diagnosis of a disease and recombinant DNA studies.

In another exemplary embodiment of the present invention, the E507K/R536K/R/R660V Taq polymerase was used to confirm whether an ability of extending mismatched primers with respect to a template with Q61H, G13D or G12S SNP at the KRAS gene, and a template with L858R SNP at the EGFR gene was reduced.

As a result, as shown in FIGS. 10a to 10d, 11, 12 and 13, it was confirmed that Taq DNA polymerase having E507K/R536K/R587I/R660V variations, compared with Taq polymerase having E507K/R536K/R660V variations, has superior mismatch extension selectivity. Therefore, it is expected that the Taq DNA polymerase having E507K/R536K/R587I/R660V variations according to the present invention can also be effectively used in medical diagnosis of a disease and recombinant DNA studies.

The present invention also relates to a composition for detecting a gene variation or SNP, which includes the DNA polymerase according to the present invention, and a PCR kit including the same.

According to an exemplary embodiment of the present invention, the PCR kit may be applied to general PCR (first generation PCR), real-time PCR (second generation PCR), digital PCR (third generation PCR) or MassARRAY.

In the PCR kit of the present invention, the digital PCR may be competitive allele-specific TaqMan PCR (CAST PCR) or droplet digital PCR (ddPCR), and more specifically, allele-specific cast PCR or allele-specific droplet digital PCR, but the present invention is not limited thereto.

The "CAST PCR" is a method of detecting and quantifying rare mutations from a large amount of sample containing normal wild-type gDNA, and to inhibit non-specific amplification from a wild-type allele, higher specificity may be generated by the combination of allele-specific TaqMan® qPCR with an allele-specific MGB inhibitor, compared to traditional allele-specific PCR.

The "droplet digital PCR" is a system for counting target DNA after a 20 µl PCR product is fractionated into 20,000 droplets and then amplified, and may be used to count positive droplets (1) and negative droplets (0) considered as digital signals according to the amplification of target DNA in droplets, calculate the number of copies of target DNA by the Poisson distribution, and finally determine result values with the number of copies per µl sample, and used to detect rare mutations, amplify a very small amount of gene and simultaneously confirm a mutation type.

The "MassARRAY" is a multiplexing analysis method that can be applied to various genome studies such as genotyping, using a MALDI-TOF mass spectrometer, and may be used to rapidly analyze various samples and targets at low cost or to perform customized analysis only for a specific target.

The PCR kit of the present invention may include any reagent or other elements, which are recognized for use in primer extension by technicians of ordinary skill in the art.

According to an exemplary embodiment of the present invention, the PCR kit may further include one or more matched primers, one or more mismatched primers or both of one or more matched primers and one or more mismatched primers, wherein the one or more matched primers and one or more mismatched primers are hybridized with a target sequence, and the mismatched primer may include a non-canonical nucleotide at a position of 7 bases from the 3' end of the primer with respect to the hybridized target sequence.

The PCR kit of the present invention may further include a nucleoside triphosphate.

The PCR kit of the present invention may further include a) one or more buffers; b) a quantification reagent binding to double-stranded DNA; c) a polymerase blocking antibody, d) one or more control values or control sequences; and e) one or more templates.

The present invention relates to a PCR buffer composition for increasing the activity of a DNA polymerase with increased gene variation specificity, which includes 25 to 100 mM KCl; and 1 to 15 mM $(NH_4)_2SO_4$, and has the final pH of 8.0 to 9.0.

Polymerases used in PCR should be optimal reaction buffers mixed with various materials to perform proper functions. The reaction buffers generally contain an element for pH stabilization, a metal ion as a cofactor, and a stabilization element for preventing the denaturation of a polymerase.

The KCl is an element required for enzyme stabilization, and helps pairing of a primer to target DNA. In the present invention, an optimal concentration was determined by adjusting a KCl concentration in the reaction buffer to confirm a cation concentration in a state in which the amplification by mismatching is delayed as much as possible, and the amplification efficiency by matching is not reduced.

As a result of confirming an amplification delay effect by mismatching according to the change in KCl concentration in the reaction buffer using each of E507K, E507K/R536K, E507K/R660V and E507K/R536K/R660V Taq polymerases, as shown in FIGS. 14a to 14d, the E507K/R536K/R660V Taq polymerase showed an excellent amplification delay effect caused by mismatching without KCl in the reaction buffer, the E507K/R536K and E507K/R660V Taq polymerases showed an excellent amplification delay effect caused by mismatching at 50 mM, and the control E507KTaq polymerase showed an excellent amplification delay effect caused by mismatching at 100 mM. Consequently, it was confirmed that the KCl concentration threshold is the lowest for the E507K/R536K/R660V Taq polymerase, and lower for the E507K/R536K and E507K/R660V Taq polymerases, compared to that of E507K Taq polymerase.

Figure 15:
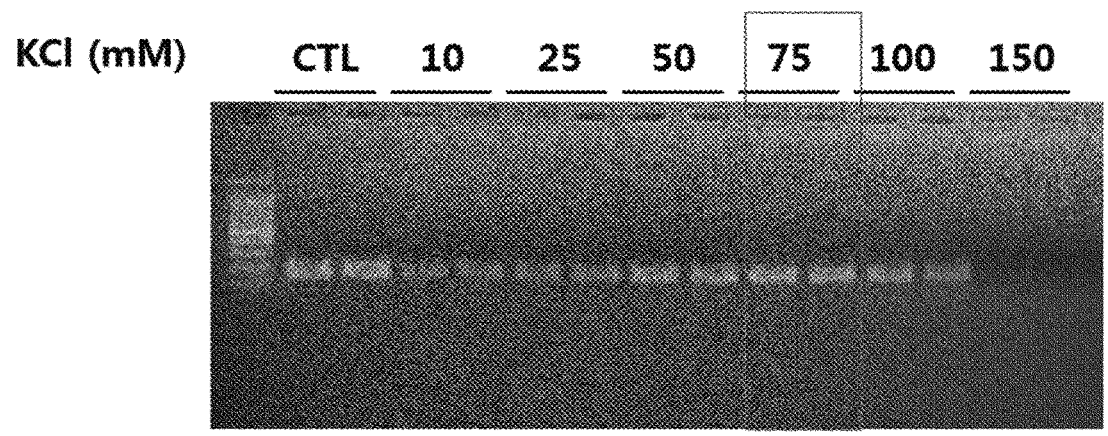
FIG. 15 shows the result of electrophoresis for a PCR product obtained by amplification with a constantly fixed $(NH_4)_2SO_4$ concentration and various KCl concentrations to confirm the optimal KCl concentration in a reaction buffer.

In addition, to determine the optimal KCl concentration, the E507K/R536K/R660V Taq polymerase was used, and amplification was performed by variously changing a KCl concentration while a $(NH_4)_2SO_4$ concentration was constantly fixed in the reaction buffer. As a result of electrophoresis performed on an amplicon, as shown in FIG. 15, the optimal KCl concentration was confirmed to be 75 mM.

Therefore, the KCl concentration of the PCR buffer composition of the present invention may be 25 to 100 mM, preferably, 60 to 90 mM, more preferably, 70 to 80 mM, and most preferably, 75 mM.

When the KCl concentration is less than 25 mM, it has no influence on general target amplification, but a difference between amplification by a matched primer and amplification by a mismatched primer may be reduced, and when the KCl concentration is more than 100 mM, the efficiency of general target amplification may be lowered.

In the PCR buffer composition, the $(NH_4)_2SO_4$ is a cofactor required for enzyme activity, and used to increase polymerase activity along with Tris. In an exemplary embodiment of the present invention, based on the determined results, the KCl concentration in the reaction buffer was constantly fixed at 75 mM, and the $(NH_4)_2SO_4$ concentration varied from 2.5 mM to 25 mM, so that the optimal $(NH_4)_2SO_4$ concentration was confirmed.

Figure 16:
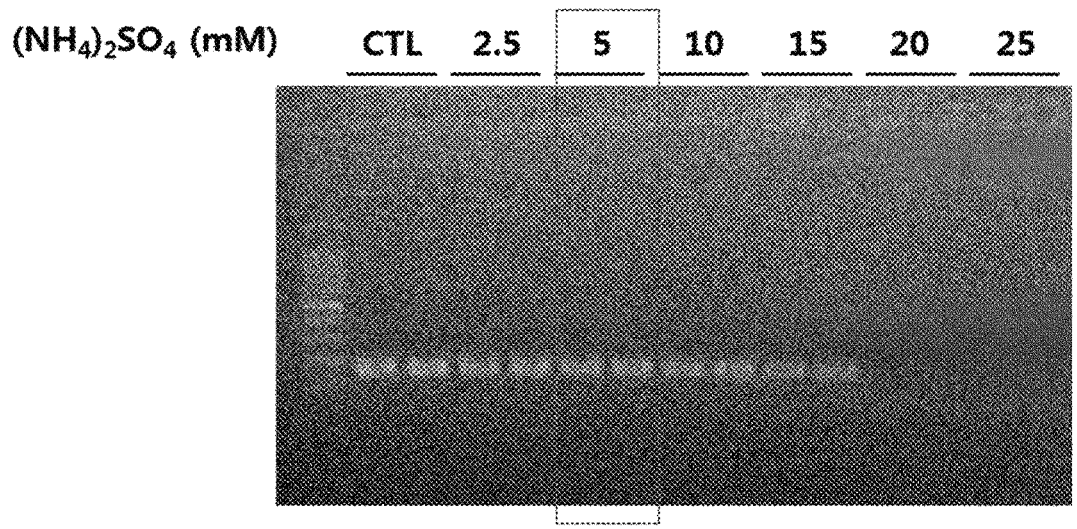
FIG. 16 shows the result of electrophoresis for a PCR product obtained by amplification with a constantly fixed KCl concentration and various $(NH_4)_2SO_4$ concentrations to confirm the optimal $(NH_4)_2SO_4$ concentration in a reaction buffer.

As a result, as shown in FIG. 16, at the $(NH_4)_2SO_4$ concentrations ranging from 2.5 to 15 mM, an amplicon was identified, confirming that the optimal $(NH_4)_2SO_4$ concentration was 5 mM.

Figure 17:
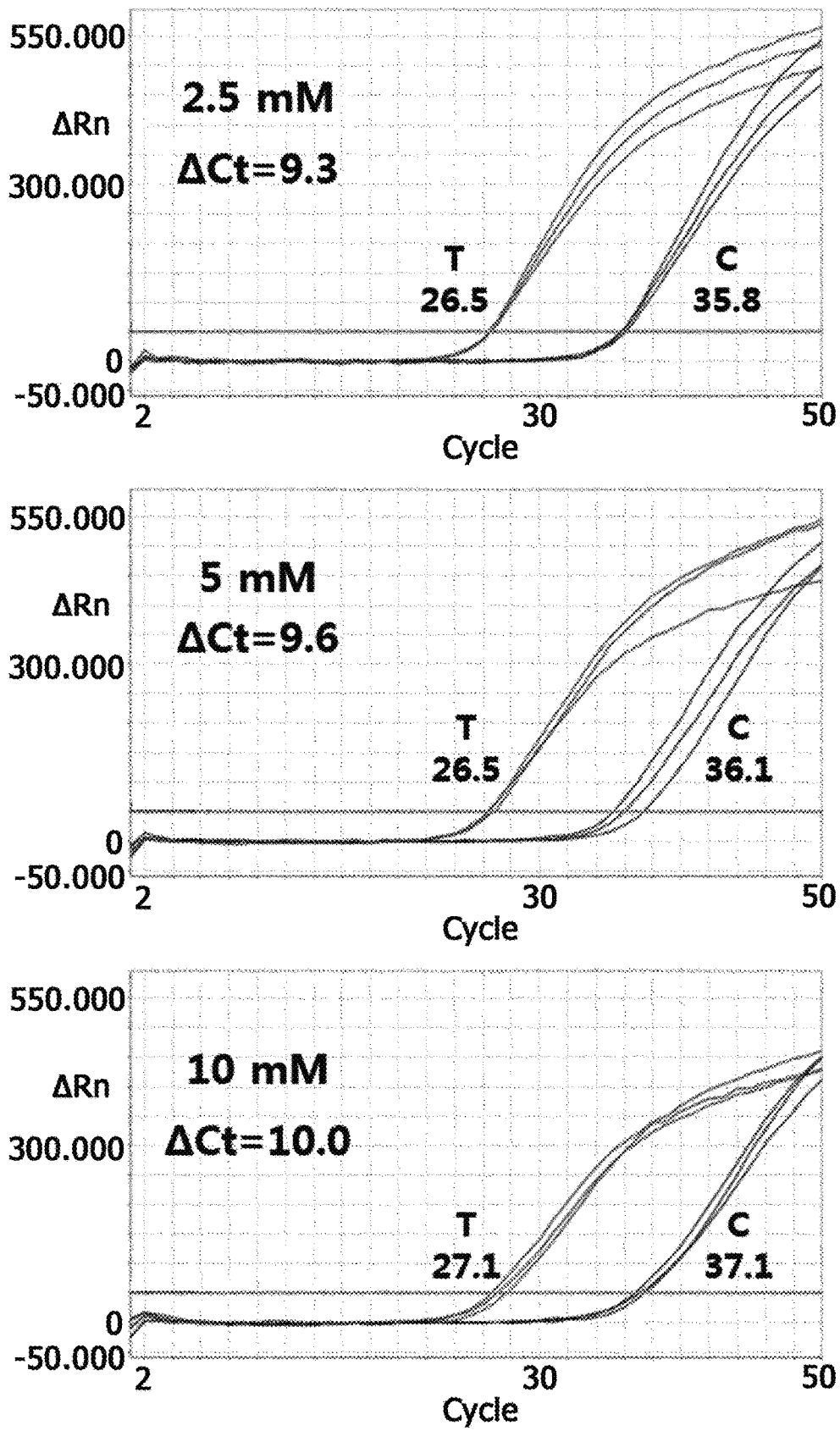
FIG. 17 is the graph showing the amplification delay effect by mismatch according to the change in $(NH_4)_2SO_4$ concentration in a reaction buffer.

In addition, by performing AS-qPCR at $(NH_4)_2SO_4$ concentrations of approximately 5 mM (2.5 mM, 5 mM and 10 mM), as shown in FIG. 17, it was confirmed that the Ct difference was the highest at 10 mM, but Ct was a little delayed and a peak was tilted in the amplification caused by matching, and the optimal $(NH_4)_2SO_4$ concentration was determined to be 5 mM.

Therefore, the $(NH_4)_2SO_4$ concentration in the PCR buffer composition may be 1 to 15 mM, preferably, 2.5 to 8 mM, more preferably, 4 to 6 mM, and most preferably, 5 mM.

When the $(NH_4)_2SO_4$ concentration is less than 1 mM, there was no influence on general target amplification, but the difference between the amplification by a matched primer and the amplification by a mismatched primer may be reduced, and when the $(NH_4)_2SO_4$ concentration is more than 15 mM, the general target amplification efficiency may be lowered.

Therefore, the optimized PCR buffer composition of the present invention may contain 70 to 80 mM KCl and 4 to 6 mM $(NH_4)_2SO_4$, and the final pH is 8.0 to 9.0.

The PCR buffer composition of the present invention may further include 5 to 80 mM tetra methyl ammonium chloride (TMAC).

TMAC is generally used to reduce amplification caused by mismatching or improve the stringency of a hybridization reaction. In an exemplary embodiment of the present invention, based on the obtained results, the optimal TMAC concentration was determined by fixing the KCl concentration at 75 mM, and the $(NH_4)_2SO_4$ concentration at 5 mM in the reaction buffer, and varying a TMAC concentration from 0 to 80 mM.

Figure 18A:
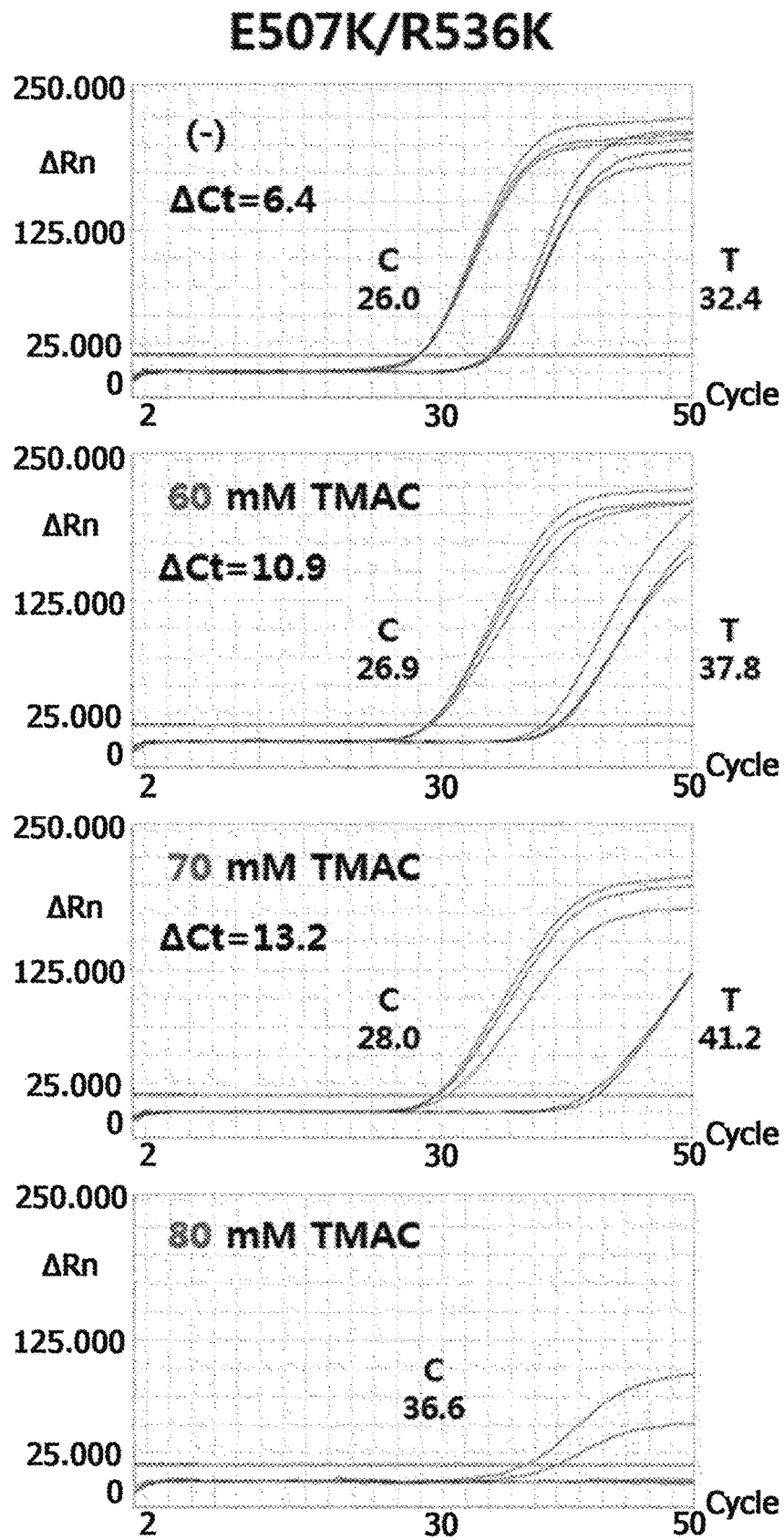
FIGS. 18a and 18b are graphs showing the amplification delay effect by mismatch according to the change in TMAC concentration after KCl and $(NH_4)_2SO_4$ concentrations are constantly fixed in a reaction buffer.
Figure 18B:
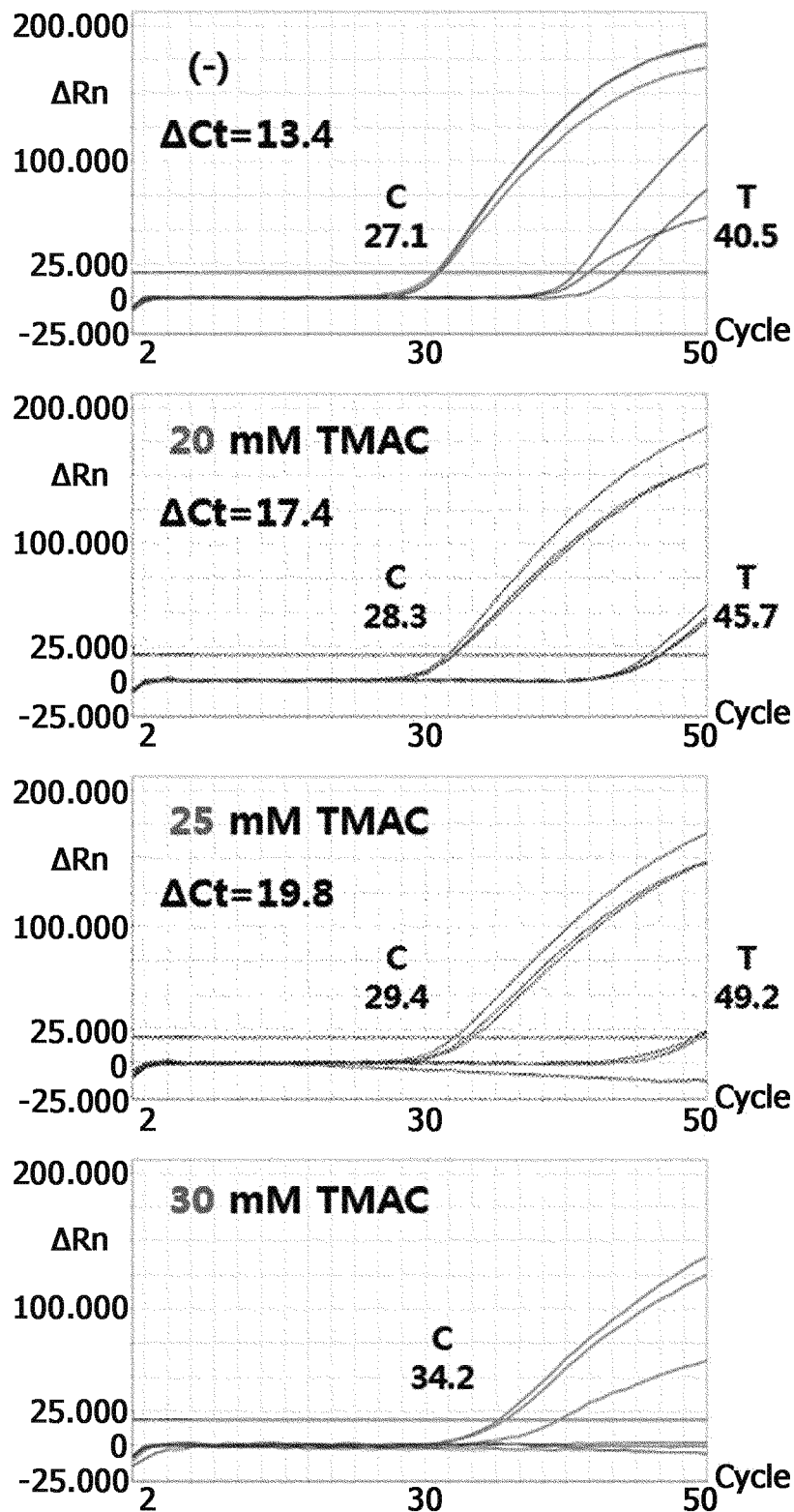
Figure 19A:
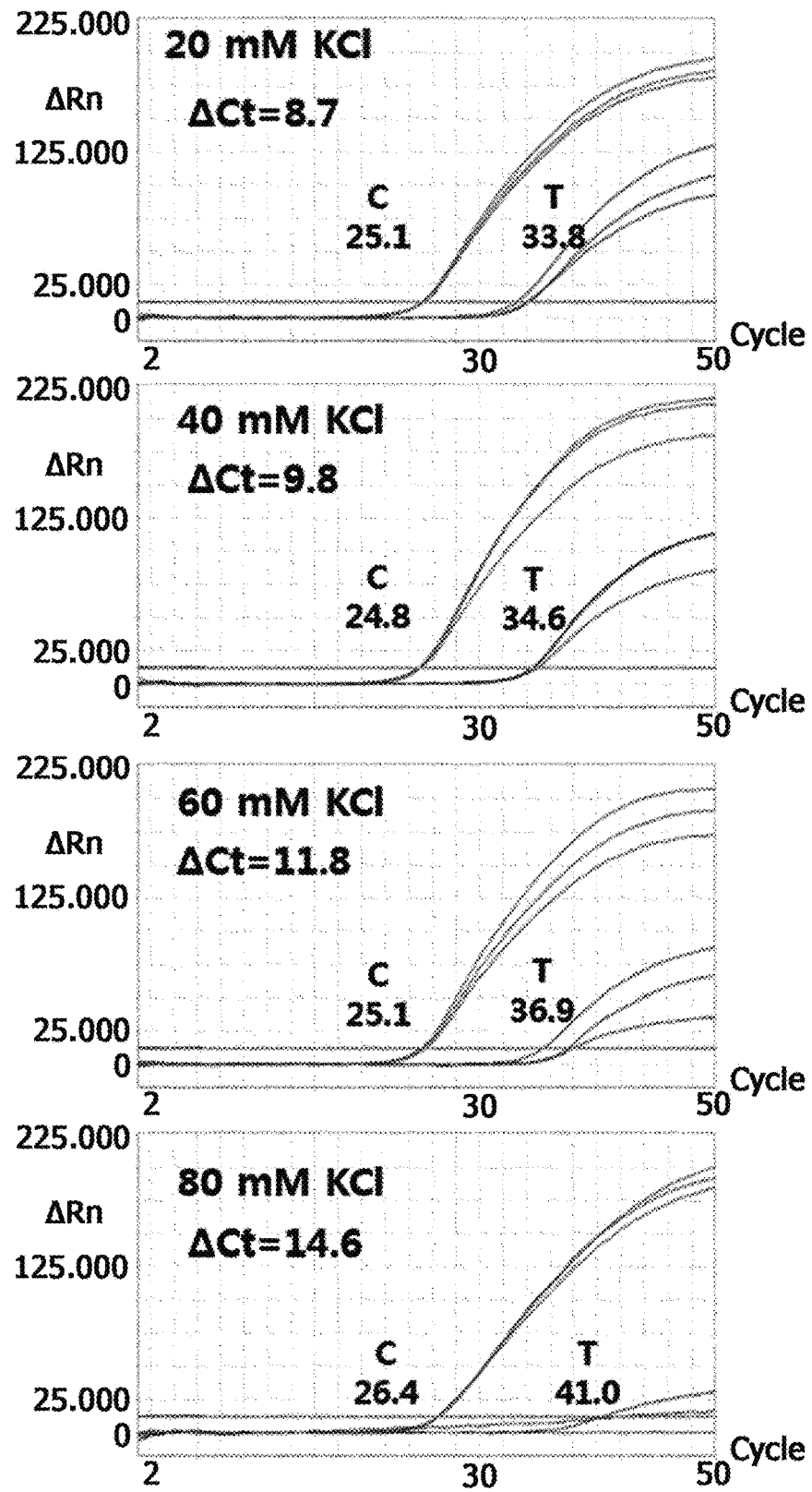
FIGS. 19a and 19b are graphs showing the amplification delay effect by mismatch according to the change in KCl concentration after TMAC and $(NH_4)_2SO_4$ concentrations are constantly fixed in a reaction buffer.
Figure 19B:
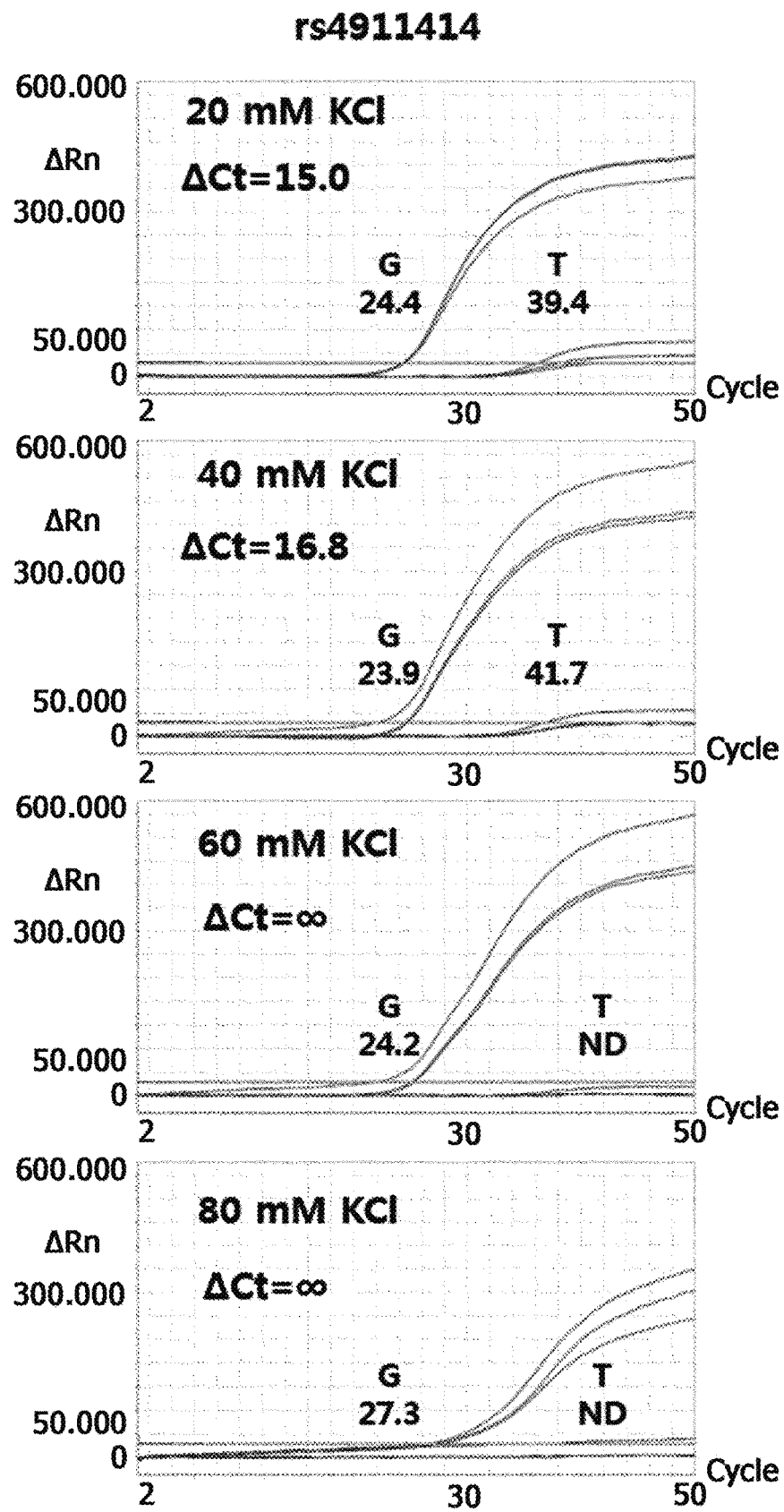

As a result, as shown in FIGS. 18a and 18b, it was confirmed that the optimal TAMC concentration was 70 mM for the E507K/R536K Taq polymerase, and 25 mM for the E507K/R536K/R660V Taq polymerase. In addition, as a result of amplification performed by constantly fixing a TMAC concentration at 25 mM and a $(NH_4)_2SO_4$ concentration at 2.5 mM, and varying a KCl concentration to 20, 40, 60 and 80 mM, as shown in FIGS. 19a and 19b, the optimal KCl concentration for SNP rs1015362 and rs4911414 was determined to be 60 mM.

When the TMAC concentration is more than 80 mM, amplification efficiency is reduced, and thus it is preferable that the TMAC concentration is in the above-mentioned range.

Therefore, when the PCR buffer composition of the present invention contains 5 to 80 mM TMAC, the KCl concentration may be 40 to 90 mM, and preferably, 50 to 80 mM, and the $(NH_4)_2SO_4$ concentration may be 1 to 7 mM, and preferably 1.5 to 6 mM.

When TMAC is contained, the optimized PCR buffer composition of the present invention may contain 15 to 70 mM TMAC, 50 to 80 mM KCl, and 1.5 to 6 mM $(NH_4)_2SO_4$, and the final pH may be 8.0 to 9.0.

The PCR buffer composition of the present invention may further contain Tris·Cl and $MgCl_2$, and additionally contain Tween 20 and bovine serum albumin (BSA).

The present invention also provides a PCR kit for detecting a gene variation or SNP, which includes the above-described PCR buffer composition.

The PCR kit of the present invention may further include a DNA polymerase comprising a Taq polymerase amino acid sequence of SEQ ID NO: 1, where the DNA polymerase has substitution(s) of the following amino acids:
   (a) a substitution at amino acid residue 507 in the amino acid sequence of SEQ ID NO: 1; and
   (b) (i) a substitution at amino acid residue 536 in the amino acid sequence of SEQ ID NO: 1,
     (ii) a substitution at amino acid residue 660 in the amino acid sequence of SEQ ID NO: 1,
     (iii) substitutions at amino acid residues 536 and 660 in the amino acid sequence of SEQ ID NO: 1, or (iv) substitutions at amino acid residues 536, 587 and 660 in the amino acid sequence of SEQ ID NO: 1.

According to an exemplary embodiment of the present invention, the substitution at the amino acid residue 507 may be a substitution of glutamic acid (E) with lysine (K), the substitution at the amino acid residue 536 may be a substitution of arginine (R) with lysine (K), the substitution at the amino acid residue 587 may be a substitution of arginine (R) with isoleucine (I), and the substitution at the amino acid residue 660 may be a substitution of arginine (R) with valine (V).

An additional description of the DNA polymerase included in the PCR kit of the present invention is the same as described above, and therefore, the overlapping description will be omitted.

Other components of the PCR kit for detecting a gene variation or SNP, which includes the PCR buffer composition of the present invention are the same as described above, and the overlapping description will be omitted.

The present invention also relates to a method of in vitro detecting one or more gene variations or SNPs using the kit for detecting a gene variation or SNP, which includes the PCR buffer composition for increasing activity of the DNA polymerase with increased gene variation specificity.

The method is the same as the method of in vitro detecting one or more gene variations or SNPs in one or more templates using the DNA polymerase with increased gene variation specificity of the present invention, except the components of the PCR buffer composition, and therefore, the overlapping description will be omitted.

Hereinafter, the present invention will be described in further detail with reference to examples. The examples are merely provided to more fully describe the present invention, and it will be obvious to those of ordinary skill in the art that the scope of the present invention is not limited to the following examples.

EXAMPLES

Example 11

Mutagenesis of Taq Polymerase
1-1. Fragment PCR

In this example, Taq DNA polymerase in which arginine was substituted with lysine at amino acid residue 536 in the amino acid sequence of SEQ ID NO: 1 (hereinafter, referred to as "R536K"), Taq DNA polymerase in which arginine was substituted with valine at amino acid residue 660 in the amino acid sequence of SEQ ID NO: 1 (hereinafter, referred to as "R660V") and Taq DNA polymerase in which arginine was substituted with lysine at amino acid residue 536 and arginine was substituted with valine at amino acid residue 660 in the amino acid sequence of SEQ ID NO: 1 (hereinafter, referred to as "R536K/R660V") were prepared as follows.

First, using mutation-specific primers described in Table 1, as shown in (a) in FIG. 1, Taq DNA polymerase fragments (F1 to F5) were amplified by PCR. Reaction conditions are as in Table 2.

TABLE 1

| Primer | Sequence (5'→3') |
|---|---|
| Eco-F | GG GGTACC TCA TCA CCC CGG (SEQ ID NO: 17) |
| R536K-R | CTT GGT GAG CTC CTT GTA CTG CAG GAT (SEQ ID NO: 18) |

TABLE 1 -continued

| Primer | Sequence (5'→3') |
|---|---|
| R536K-F | ATC CTG CAG TAC AAG GAG CTC ACC AAG (SEQ ID NO: 19) |
| R660V-R | GAT GGT CTT GGC CGC CAC GCG CAT CAG GGG (SEQ ID NO: 20) |
| R660V-F | CCC CTG ATG CGC GTG GCG GCC AAG ACC ATC (SEQ ID NO: 21) |
| Xba-R | GC TCTAGA CTA TCA CTC CTT GGC GGA GAG CCA (SEQ ID NO: 22) |

TABLE 2

| | |
|---|---|
| 10 × pfu buffer (SolGent) | 2.5 μl |
| dNTP (10 mM each) | 1 μl |
| F primer (10 pmol/μl) | 1 μl |
| R primer (10 pmol/μl) | 1 μl |
| Distilled water | 18 μl |
| pUC19-Taq (10 ng/μl) | 1 μl |
| Pfu polymerase | 0.5 μl |
| 30 cycles (Ta = 60° C.) | 25 μl |

PCR products were subjected to electrophoresis, thereby detecting a band for each fragment as shown in (b) in FIG. 1, indicating that a desired fragment was amplified.

1-2. Overlap PCR

Each amplified fragment obtained in 1-1 was used as a template, and full-length amplification thereof was performed using primers at both ends (Eco-F and Xba-R primers). Reaction conditions are as in Tables 3 and 4.

TABLE 3

| R660V or R536K | |
|---|---|
| 10 × pfu buffer (SolGent) | 5 μl |
| 5 × enhancer (SolGent) | 10 μl |
| dNTP (10 mM each) | 1 μl |
| Eco-F primer (10 pmol/μl) | 2 μl |
| Xba-R primer (10 pmol/μl) | 2 μl |
| Distilled water | 27 μl |
| Fragment 1 (or fragment 3) | 1 μl |
| Fragment 2 (or fragment 4) | 1 μl |
| Pfu polymerase | 1 μl |
| 40 cycles (Ta = 62° C.) | 50 μl |

TABLE 4

| R536K/R660V | |
|---|---|
| 10 × pfu buffer (SolGent) | 5 μl |
| 5 × enhancer (SolGent) | 10 μl |
| dNTP (10 mM each) | 1 μl |
| Eco-F primer (10 pmol/μl) | 2 μl |
| Xba-R primer (10 pmol/μl) | 2 μl |
| Distilled water | 26 μl |
| Fragment 2 | 1 μl |
| Fragment 3 | 1 μl |
| Fragment 5 | 1 μl |
| Pfu polymerase | 1 μl |
| 40 cycles (Ta = 62° C.) | 50 μl |

Consequently, as shown in (c) in FIG. 1, it was confirmed that the Taq polymerases of "R536K," "R660V" and "R536K/R660V" were amplified.

1-3. Ligation pUC19 was digested with restriction enzymes EcoRI/XbaI at 37° C. for 4 hours under conditions shown in Table 5 below, DNA was purified, and the purified DNA was treated with SAP at 37° C. for 1 hour under conditions shown in Table 6, thereby preparing a vector.

TABLE 5

| | |
|---|---|
| 10 × CutSmart buffer (NEB) | 2.5 µl |
| pUC19 (500 ng/µl) | 21.5 µl |
| EcoRI-HF (NEB) | 0.5 µl |
| Xba I (NEB) | 0.5 µl |
| | 25 µl |

TABLE 6

| | |
|---|---|
| 10 × SAP buffer (Roche) | 2 µl |
| Purified DNA | 17 µl |
| SAP (Roche) | 1 µl |
| | 20 µl |

Figure 2:
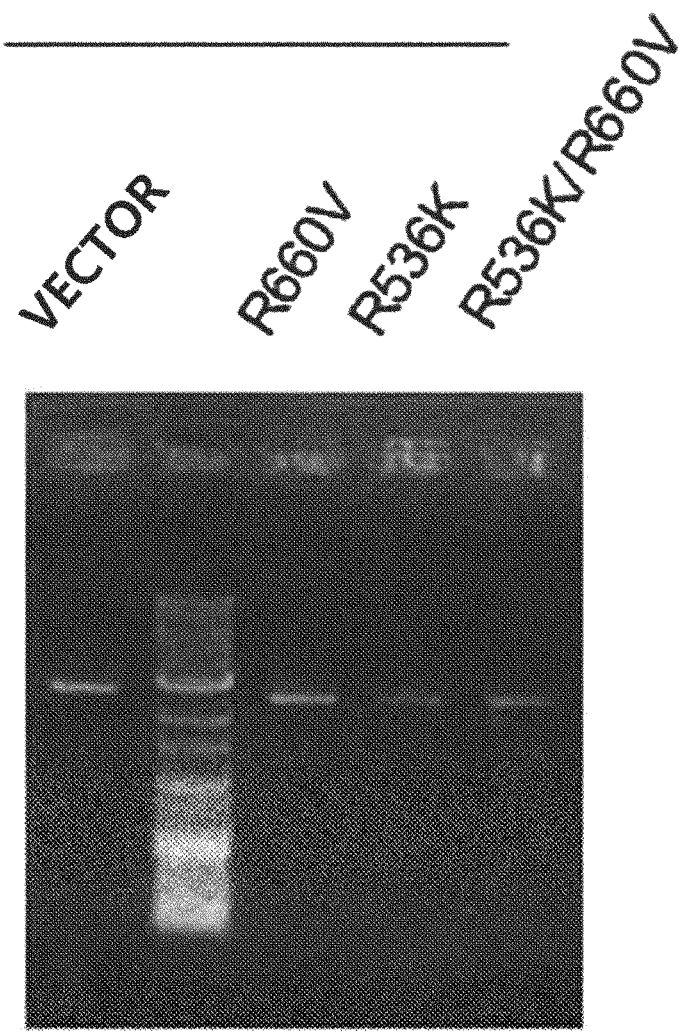
FIG. 2 shows the result of electrophoresis for a pUC19 vector which is digested with restriction enzymes EcoRI/XbaI and treated with SAP and the purified overlap PCR products of (c) in FIG. 1.
Figure 3:
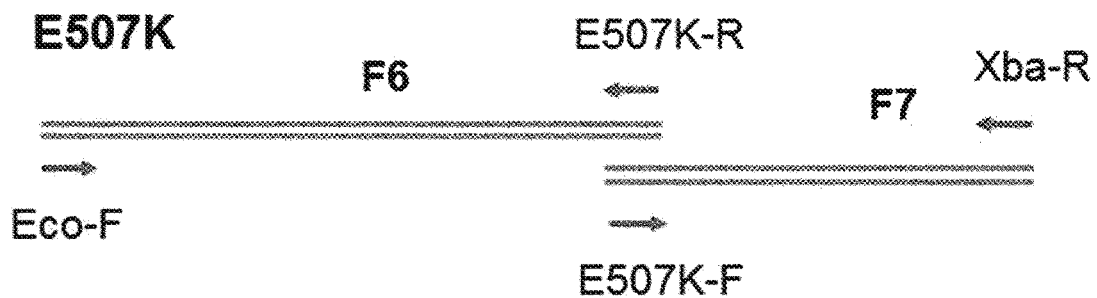
FIG. 3 is the schematic representation of fragment PCR and overlap PCR during the preparation of Taq DNA polymerases having E507K, E507K/R536K, E507K/R660V and E507K/R536K/R660V variations, respectively.

After the overlap PCR product was obtained in Example 1-2 and digested with restriction enzymes EcoRI/XbaI at 37° C. for 3 hours under conditions shown in Table 7, an insert was gel-extracted with the prepared vector (FIG. 2).

TABLE 7

| | |
|---|---|
| 10 × CutSmart buffer (NEB) | 2 µl |
| Purified PCR product | 17 µl |
| EcoRI-HF (NEB) | 0.5 µl |
| XbaI (NEB) | 0.5 µl |
| | 20 µl |

After ligation was performed at room temperature for 2 hours under conditions shown in Table 8, *E. coli* DH5α was transformed with the resulting vectors and then screened in a medium containing ampicillin. Plasmids prepared from the collected colonies were sequenced, thereby obtaining Taq DNA polymerase mutants ("R536K," "R660V" and "R536K/R660V") into which desired variation(s) is/are introduced.

TABLE 8

| | Vector only | Vector + Insert |
|---|---|---|
| 10 × ligase buffer (SolGent) | 1 µl | 1 µl |
| Vector | 1 µl | 1 µl |
| Insert | — | 3 µl |
| Distilled water | 7 µl | 4 µl |
| T4 DNA ligase (SolGent) | 1 µl | 1 µl |
| | 10 µl | 10 µl |

Example 21

Introduction of E507K Variation 2-1. Fragment PCR

The Taq polymerase activity of the "R536K," "R660V" and "R536K/R660V" prepared in Example 1 was tested, thereby confirming that the activity was decreased (data not shown), the E507K variation (substitution of glutamic acid with lysine at amino acid residue 507 in the amino acid sequence of SEQ ID NO: 1) was additionally introduced into each of R536K, R660V and R536K/R660V, and the E507K variation was introduced into wild-type Taq DNA polymerase (WT) as a control. A method of preparing the E507K variation-introduced Taq DNA polymerase is the same as described in Example 1.

Taq DNA polymerase fragments (F6 to F7) shown in Table 3 were amplified by PCR using mutation-specific primers shown in Table 9. Reaction conditions are shown in Table 10.

TABLE 9

| Primer | Sequence (5'→3') |
|---|---|
| Eco-F | GG GGTACC TCA TCA CCC CGG (SEQ ID NO: 17) |
| E507K-R | CTT GCC GGT CTT TTT CGT CTT GCC GAT (SEQ ID NO: 23) |
| E507K-F | ATC GGC AAG ACG AAA AAG ACC GGC AAG (SEQ ID NO: 24) |
| Xba-R | GC TCTAGA CTA TCA CTC CTT GGC GGA GAG CCA (SEQ ID NO: 22) |

TABLE 10

| | |
|---|---|
| 10 × pfu buffer (SolGent) | 2.5 µl |
| dNTP (10 mM each) | 1 µl |
| F primer (10 pmol/µl) | 1 µl |
| R primer (10 pmol/µl) | 1 µl |
| Distilled water | 18 µl |
| Template plasmid (10 ng/µl) | 1 µl |
| Pfu polymerase | 0.5 µl |
| 30 cycles (Ta = 60° C.) | 25 µl |

*Template plasmids: pUC19-Taq (WT), pUC19-Taq (R536K), pUC19-Taq (R660V), and pUC19-Taq (R536K/R660V)

2-2. Overlap PCR

Full-length amplification was performed on each of the amplified fragments obtained in 2-1 as a template using primers (Eco-F and Xba-R primers) at both ends. Reaction conditions are shown in Table 11.

TABLE 11

| | |
|---|---|
| 10X pfu buffer (SolGent) | 5 µl |
| 5X enhancer (SolGent) | 10 µl |
| dNTP (10 mM each) | 1 µl |
| Eco-F primer (10 pmol/µl) | 2 µl |
| Xba-R primer (10 pmol/µl) | 2 µl |
| Distilled water | 27 µl |
| Fragment 6 | 1 µl |
| Fragment 7 | 1 µl |
| Pfu polymerase | 1 µl |
| 40 cycles (Ta = 62° C.) | 50 µl |

2-3. Ligation pUC19 was digested with restriction enzymes EcoRI/XbaI at 37° C. for 4 hours under conditions shown in Table 5 above, DNA was purified, the purified DNA was treated with SAP at 37° C. for 1 hour under conditions shown in Table 6, thereby preparing a vector.

Figure 4:
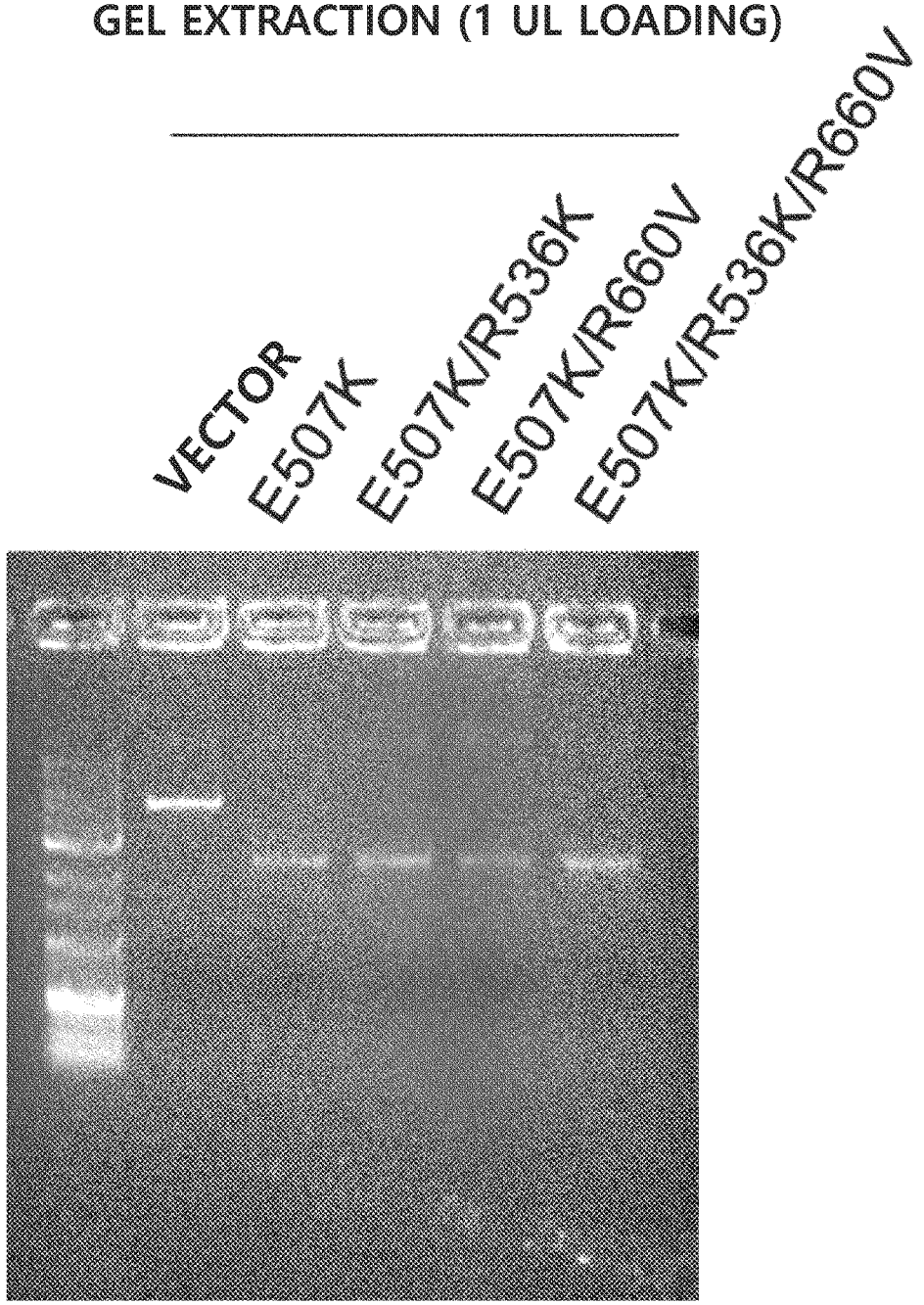
FIG. 4 shows the result of electrophoresis for a pUC19 vector digested with EcoRI/XbaI and then treated with SAP and the purified overlap PCR product of FIG. 3 for gel extraction.

After the overlap PCR product was obtained in Example 2-2 and digested with restriction enzymes EcoRI/XbaI at 37° C. for 3 hours under conditions shown in Table 7, an insert was gel-extracted with the prepared vector (FIG. 4).

After ligation was performed at room temperature for 2 hours under conditions shown in Table 8, *E. coli* DH5α or DH10β was transformed with the resulting vectors and then screened in a medium containing ampicillin. Plasmids prepared from the collected colonies were sequenced, thereby obtaining E507K variation-introduced Taq DNA polymerase mutants ("E507K/R536K," "E507K/R660V" and "E507K/R536K/R660V").

Example 3

Performance of qPCR Using DNA Polymerase of the Present Invention

The Taq polymerase having each of the "E507K/R536K," "E507K/R660V" and "E507K/R536K/R660V" variations obtained in Example 2 was used to confirm whether an ability of extending a mismatched primer with respect to a template including a SNP was reduced. As a control, the "E507K" Taq polymerase having the E507K variation was used.

The templates including SNPs used herein are rs1408799, rs1015362 and rs4911414, and genotypes of the templates and sequence data of specific primers (IDT, USA) thereof are shown in Tables 12 and 13 below.

TABLE 12

Genotype of template

| rs1408799 | TT |
| rs1015362 | CC |
| rs4911414 | GG |

TABLE 13

| Primer Name | | Sequence (5'→3') |
|---|---|---|
| rs1408799 | Forward | CCAGTGTTAGGTTATTTCTAACTTG (SEQ ID NO: 25) |
| | Reverse_T | GCTCGGAGCACATGGTCAA (SEQ ID NO: 26) |
| | Reverse_C | GCTCGGAGCACATGGTCAG (SEQ ID NO: 27) |
| rs1015362 | Forward | TGAAGAGCAGGAAAGTTCTTCA (SEQ ID NO: 28) |
| | Reverse_C | ACTGTGTGTCTGAAACAGTG (SEQ ID NO: 29) |
| | Reverse_T | ACTGTGTGTCTGAAACAGTA (SEQ ID NO: 30) |
| rs4911414 | Forward_G | GTAAGTCTTTGCTGAGAAATTCATTG (SEQ ID NO: 31) |
| | Forward_T | GTAAGTCTTTGCTGAGAAATTCATTT (SEQ ID NO: 32) |
| | Reverse | AGTATCCAGGGTTAATGTGAAAG (SEQ ID NO: 33) |

Conditions for qPCR (Applied Biosystems 7500 Fast) are as shown in Table 14 below.

TABLE 14

95° C. 5 min
95° C. 20 sec    50 cycles
60° C. 30 sec

TABLE 14-continued

72° C. 30 sec
72° C. 3 min

Probes were dual-labeled as shown in Table 15 below.

TABLE 15

| Probe Name | Sequence (5'→3') | 5' fluorophore | 3' quencher |
|---|---|---|---|
| 1408799-FAM | AGATATTTGTAAGGTATTCTG GCCT (SEQ ID NO: 34) | FAM | Black Hole Quencher 1 |
| 1015362-HEX | TGCTGAACAAATAGTCCCGAC CAG (SEQ ID NO: 35) | HEX | Black Hole Quencher 1 |
| 4911141-Texas Red | TTTCTCTAGTTGCCTTTAAGA TTT (SEQ ID NO: 36) | Texas Red | Black Hole Quencher 2 |

Figure 5:
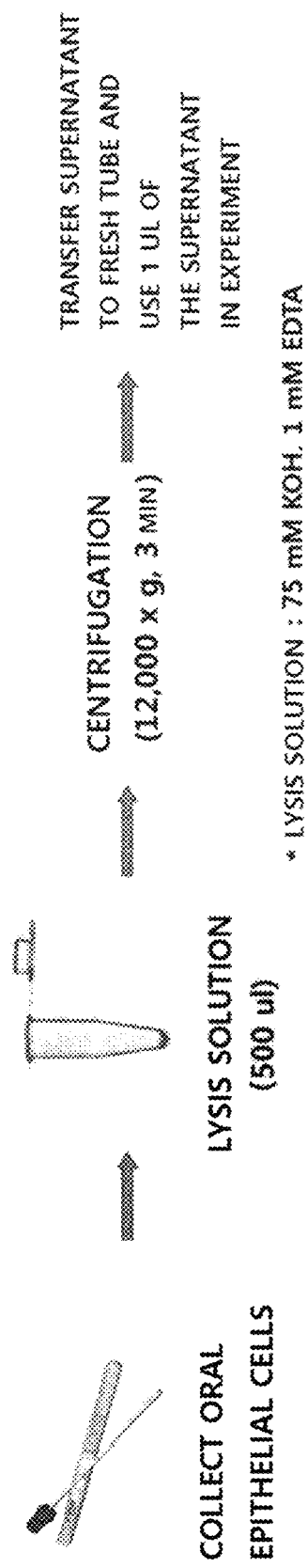
FIG. 5 is the schematic representation of the process of preparing a PCR template by collecting oral epithelial cells.
Figure 6A:
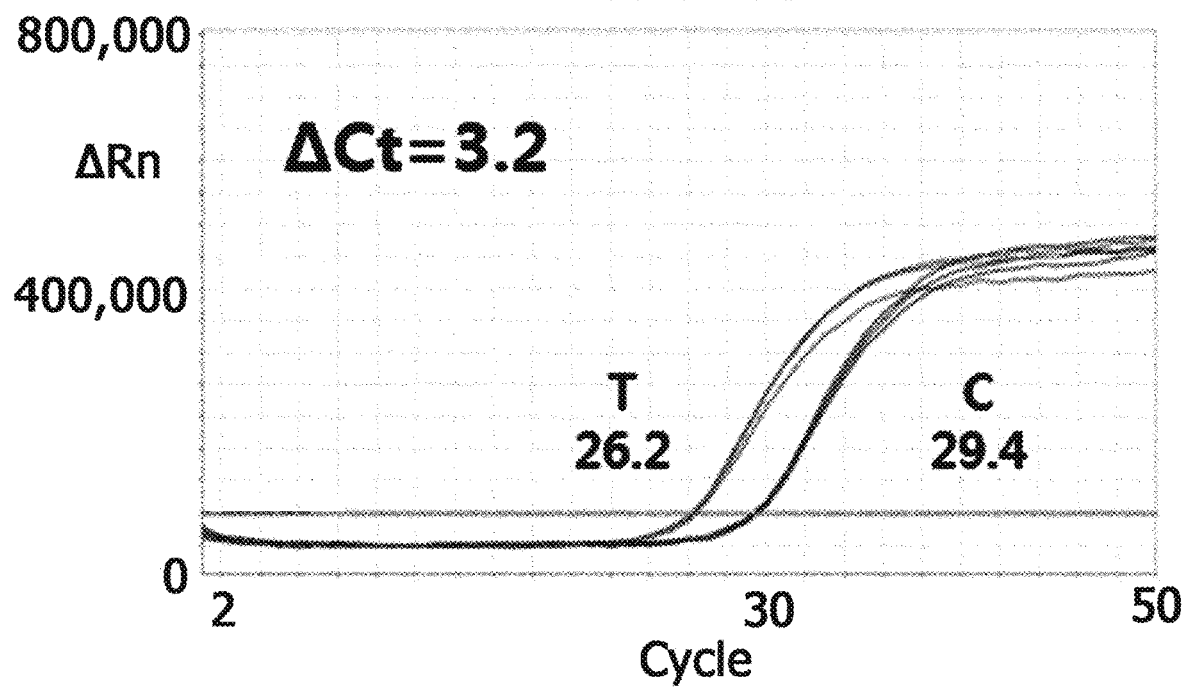
FIGS. 6a to 6d show the results of AS-qPCR for rs1408799 using Taq polymerases having E507K/R536K, E507K/R660V and E507K/R536K/R660V variations according to the present invention, and Taq polymerase having an E507K variation is used as a control.
Figure 6B:
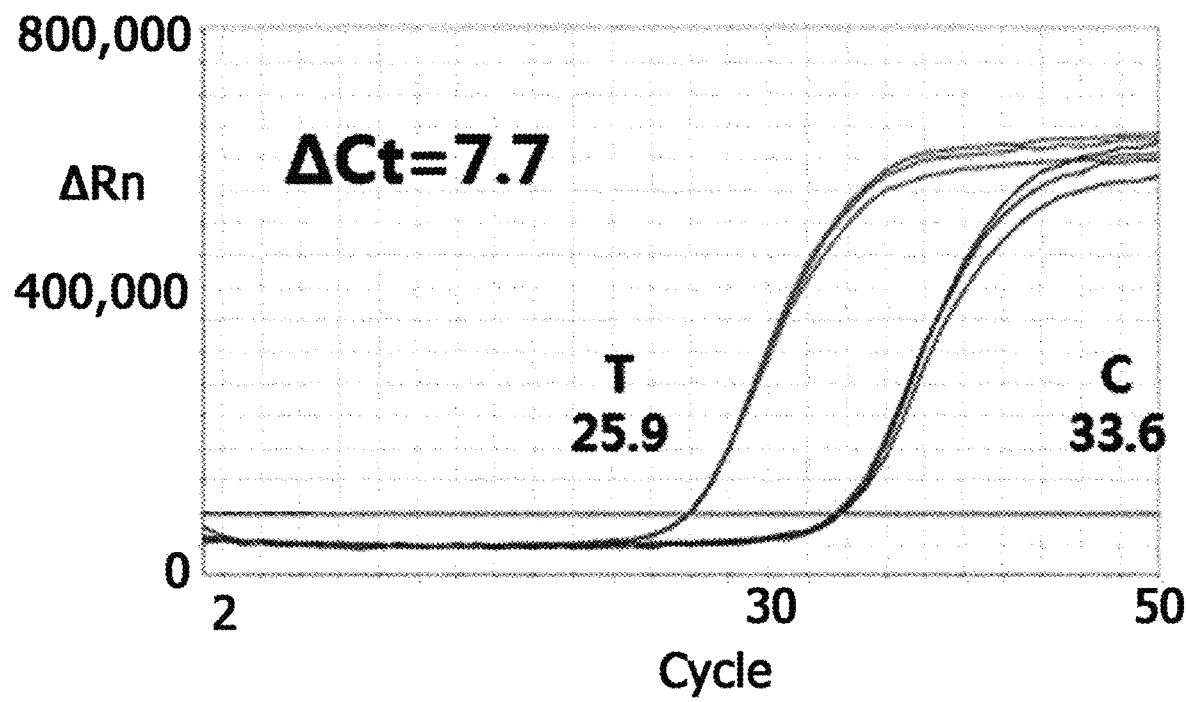
Figure 6C:
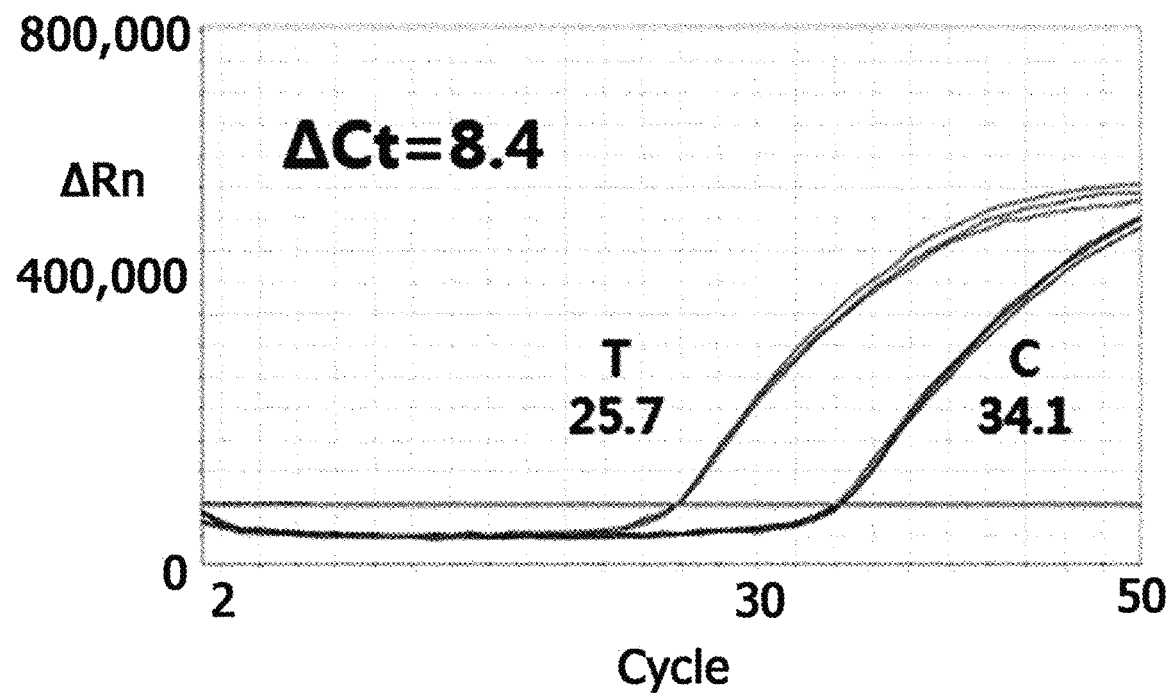
Figure 6D:
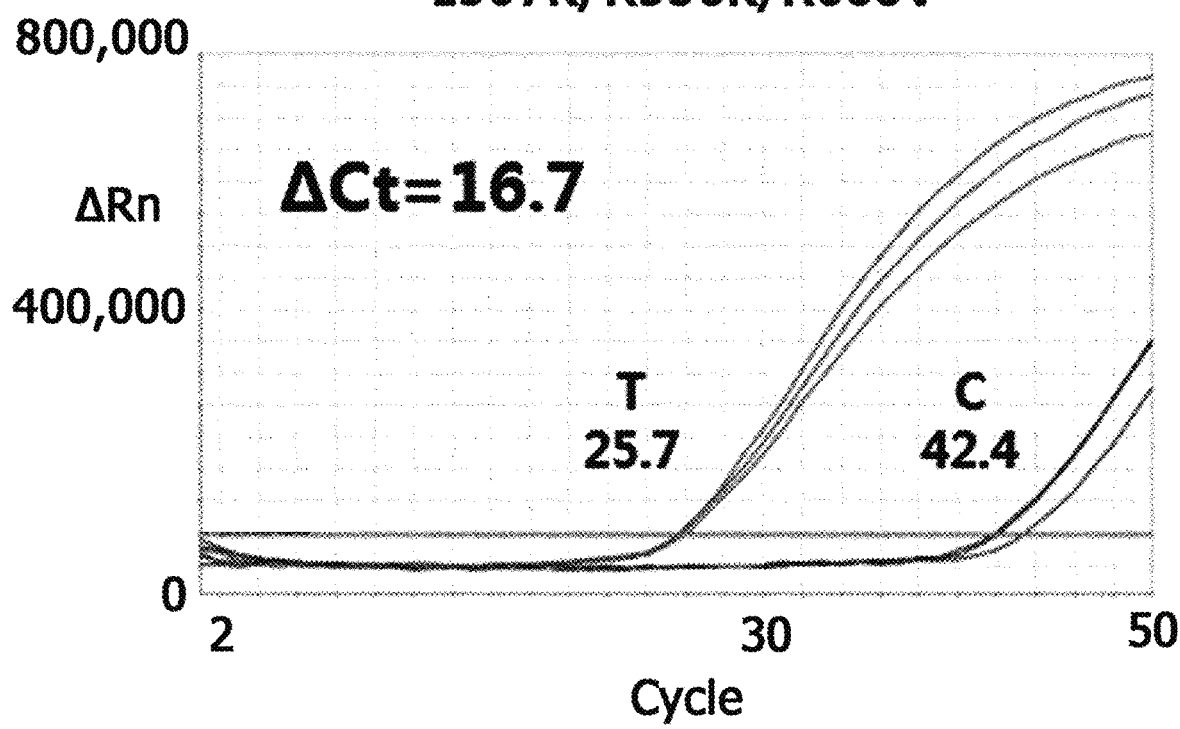
Figure 7A:
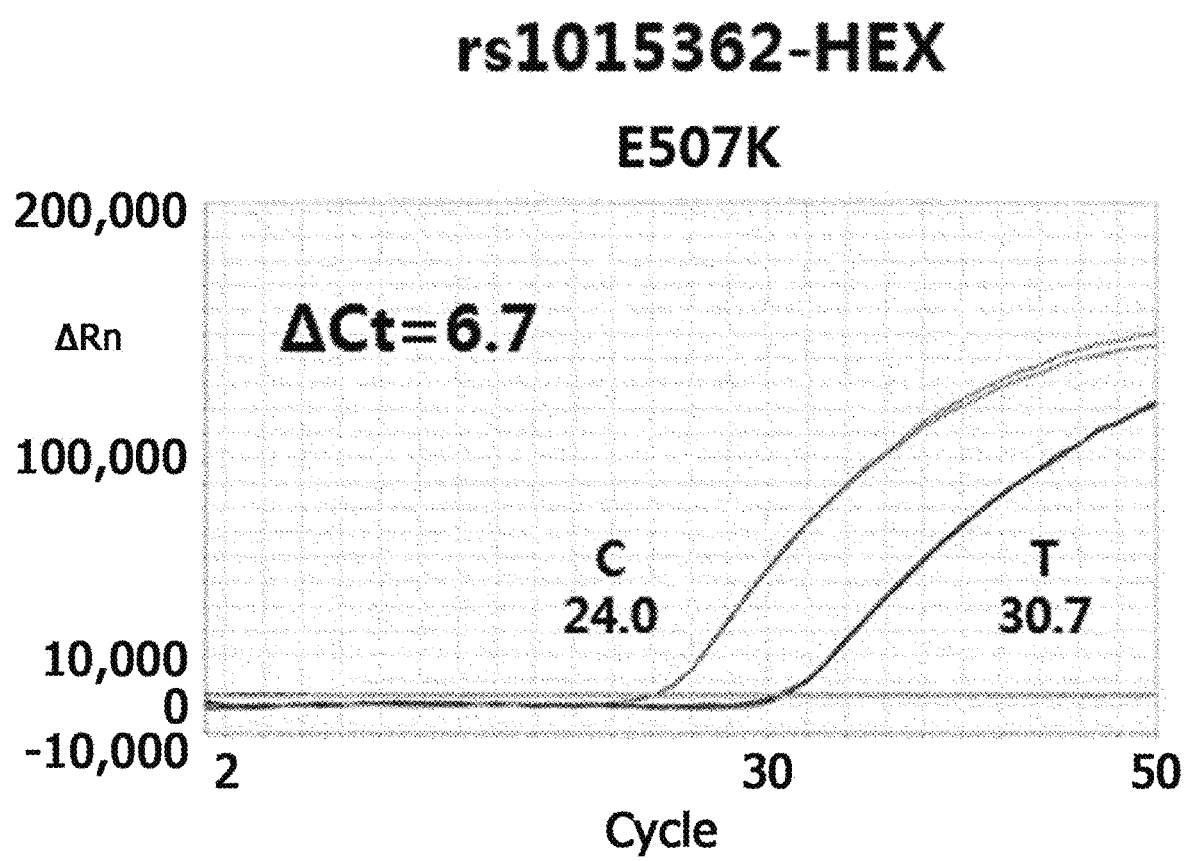
FIGS. 7a to 7d show the results of AS-qPCR for rs1015362 using Taq polymerases having E507K/R536K, E507K/R660V and E507K/R536K/R660V variations according to the present invention, and Taq polymerase having an E507K variation is used as a control.
Figure 7B:
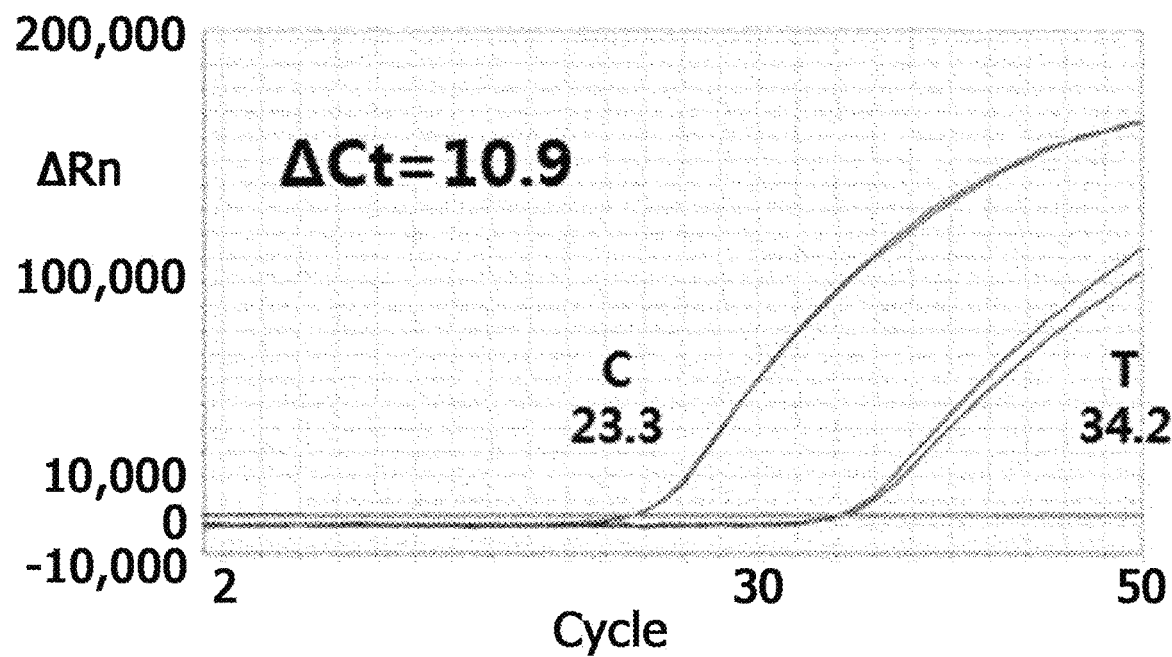
Figure 7C:
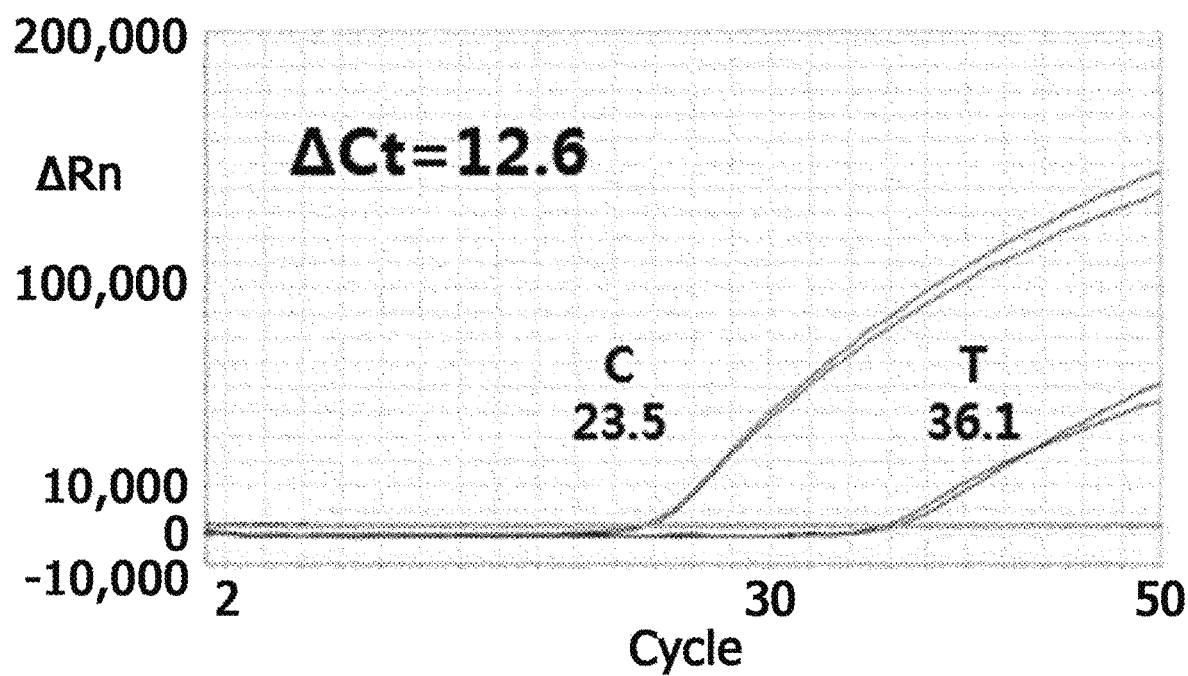
Figure 7D:
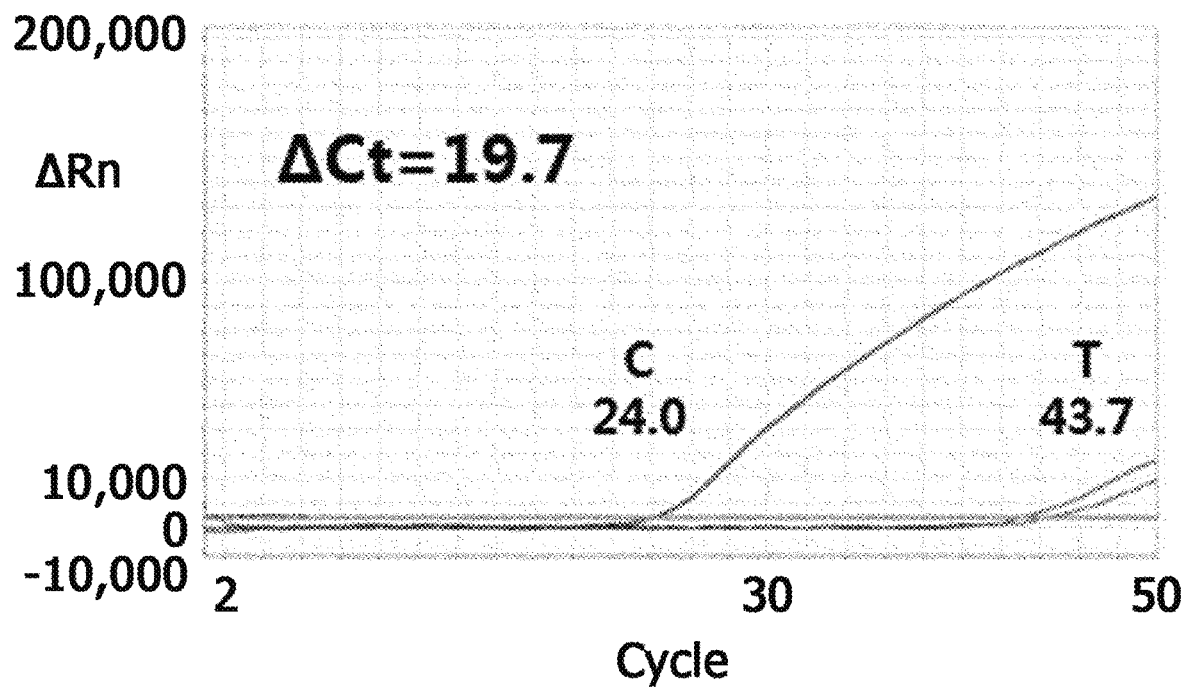
Figure 8A:
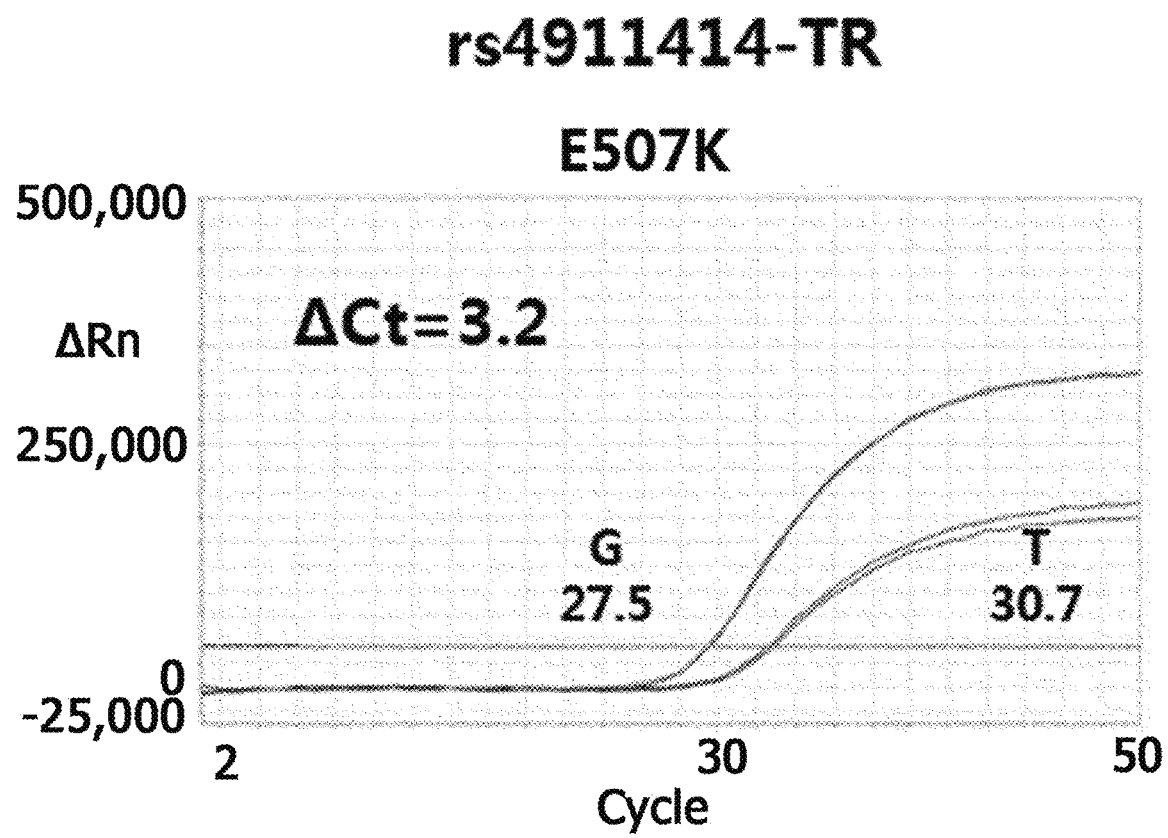
FIGS. 8a to 8d shows the results of AS-qPCR for rs4911414 using Taq polymerases having E507K/R536K, E507K/R660V and E507K/R536K/R660V variations according to the present invention, and Taq polymerase having an E507K variation is used as a control.
Figure 8B:
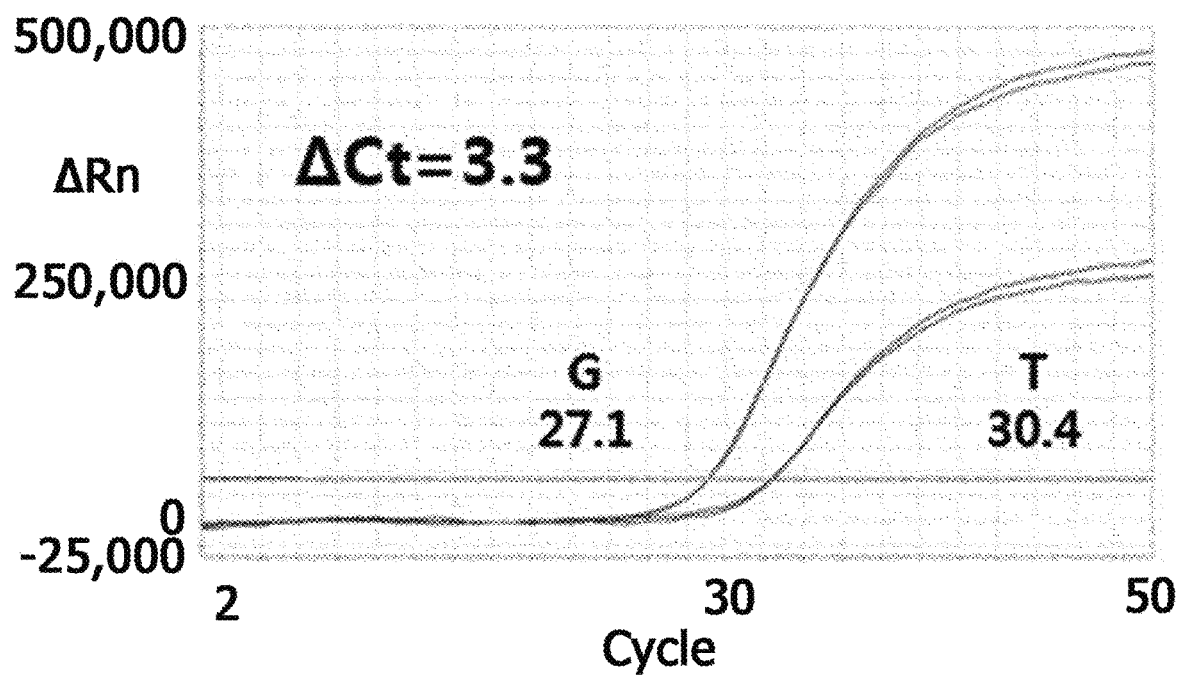
Figure 8C:
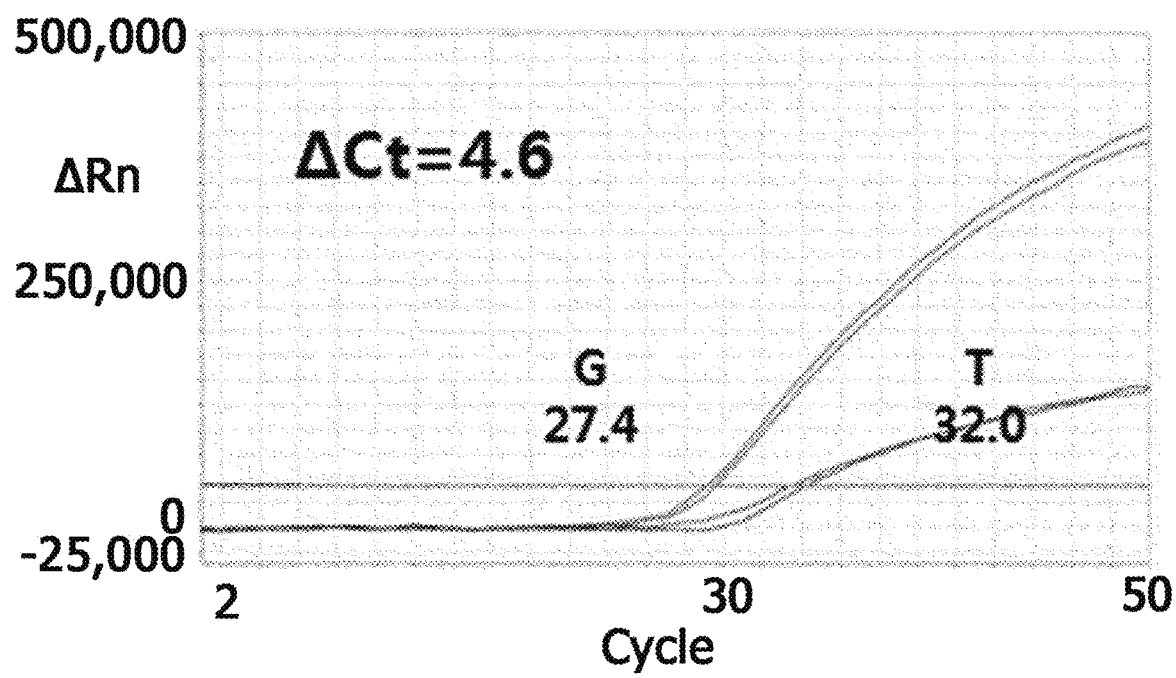
Figure 8D:
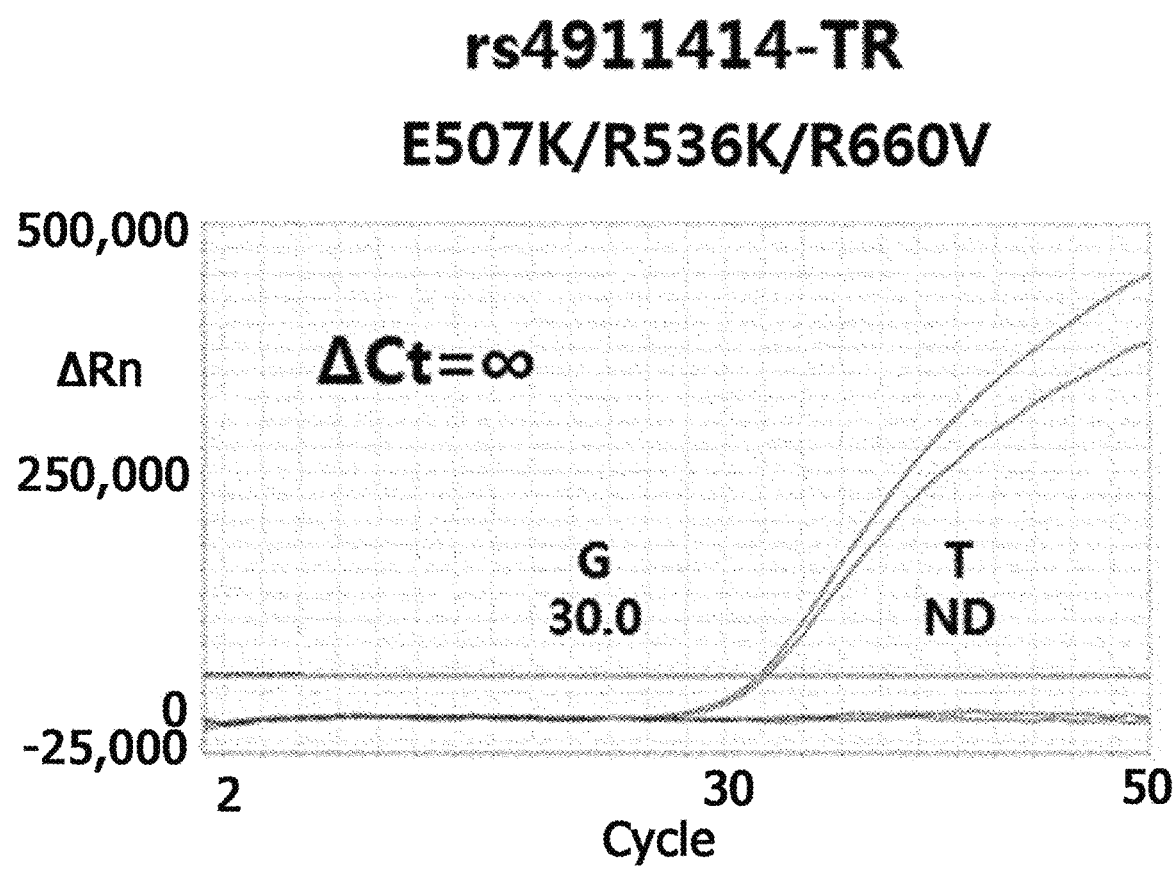

Oral epithelial cells were collected using a kit for collecting oral epithelial cells purchased from Noble Bio, lysed in 500 μl of a lysis solution, and then centrifuged at 12,000×g for 3 minutes. The supernatant was transferred to a fresh tube, and 1 μl per experiment was used (FIG. 5). Reaction conditions are shown in Table 16, and the composition of the reaction buffer is shown in Table 17.

TABLE 16

| 5X reaction buffer | 4 μl |
| 5M betaine | 2 μl |
| dNTP (10 mM each) | 0.5 μl |
| Forward primer (2 μM) | 1 μl |
| Reverse primer (2 μM) | 1 μl |
| Nuclease-free distilled water | 8 μl |
| Acquired template | 1 μl |
| Taq polymerase (2 U/μl) | 0.5 μl |
| Dual-labeled probe (4 μM) | 2 μl |
| 20 μl | |

TABLE 17

Reaction buffer (1X)
50 mM Tris-Cl (pH 8.8)
2.5 mM MgCl$_2$
50 mM KCl
5 mM (NH$_4$)$_2$SO$_4$
0.1% Tween 20
0.01% BSA The other components of the reaction solution except a specific primer were prepared as shown in Table 13 in two tubes, and each allele-specific primer was added thereto, thereby performing qPCR. Here, a difference in cycle (Ct) value at which combined fluorescent signals detected from the tubes reach the threshold fluorescence value calculated with AB 7500 software (v2.0.6) was analyzed. It is considered that, as the Ct value in the amplification by a mismatched primer is delayed, high gene variation specificity or allele specificity is exhibited. As a result of AS-qPCR for rs1408799, rs1015362 and rs4911414, as shown in FIGS. 6a-6d, 7 and 8, compared to the control E507K, when the Tap polymerase having E507K/R536K, E507K/R660V or E507K/R536K/R660V variations was used, it was confirmed that the amplification by a mismatched primer was delayed, and such an effect was most significantly exhibited in the E507K/R536K/R660V mutant.

It was confirmed that the Tap DNA polymerase having the E507K/R536K, E507K/R660V or E507K/R536K/R660V variations according to the present invention, compared to that with E507K variation, has excellent mismatch extension selectivity. Therefore, it is expected that the three types of Taq DNA polymerases can be useful for medical diagnosis of a disease and recombinant DNA studies.

Example 4

Introduction of R587I Variation 4-1. Fragment PCR

To additionally introduce a R587I variation (substitution of arginine with isoleucine at amino acid residue 587 in the amino acid sequence of SEQ ID NO: 1) into the "E507K/R536K/R660V" variation-introduced Taq clone prepared in Example 2, as shown in (a) in FIG. 9, two fragments were amplified by PCR using primers shown in Table 18 below. Reaction conditions are shown in Table 19.

TABLE 18

| Primer | Sequence (5'-3') |
|---|---|
| Kpn-F | TCC ACC CCG AGG GGT ACC TCA TCA CCC CGG CCT GGC (SEQ ID NO: 39) |
| R587I-R | CCC AAG CGG GGT GAT GAC GGG GAT GTT (SEQ ID NO: 40) |
| R587I-F | AAC ATC CCC GTC ATC ACC CGC TTG GGG (SEQ ID NO: 41) |
| Xba-R | CTG CAG GTC GAC TCT AGA CTA TCA CTC CTT GGC GGA G (SEQ ID NO: 42) |

TABLE 19

| | |
|---|---|
| 10X pfu buffer (SolGent) | 5 μl |
| dNTP (10 mM each) | 2 μl |
| F primer (10 pmol/μl) | 2 μl |
| R primer (10 pmol/μl) | 2 μl |
| Distilled water | 36 μl |
| Taq plasmid (E507K, R536K, R660V) (10 ng/μl) | 2 μl |
| Pfu polymerase | 1 μl |
| 35 cycles (Ta = 60° C.) | 50 μl |

Figure 9:
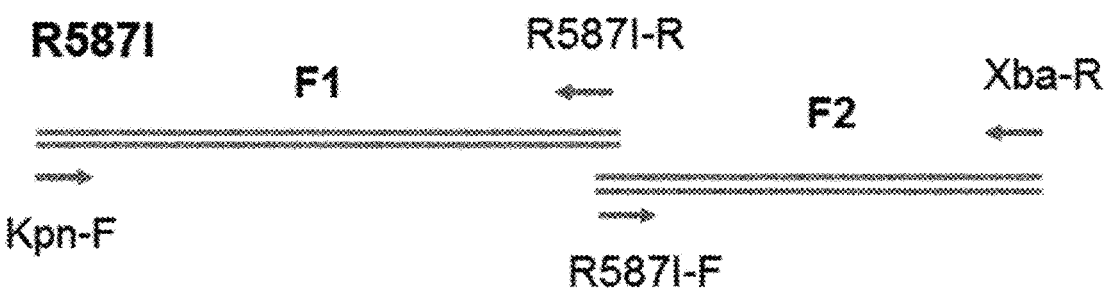
FIG. 9 shows the process of preparing Taq DNA polymerase having E507K/R536K/R587I/R660V variations: (a) the schematic representation of fragment PCR and overlap PCR; and (b) the result of electrophoresis for the amplified product obtained by the fragment PCR.
Figure 9:
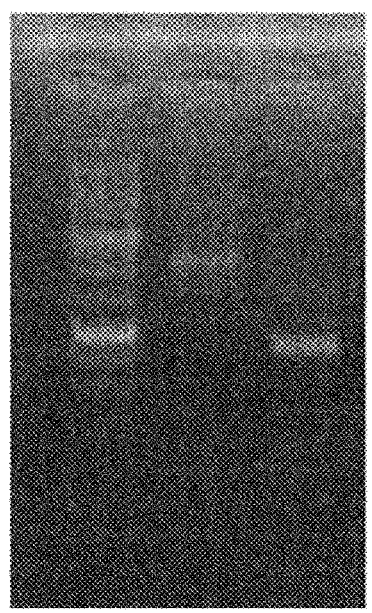

The PCR product was confirmed by electrophoresis, and thus, as shown in (b) FIG. 9, a band for each fragment was confirmed, indicating that a desired fragment was amplified.

4-2. In-Fusion Cloning

A Taq plasmid vector (E507K/R536K/R660V) was digested with restriction enzymes KpnI/XbaI at 37° C. for 4 hours under conditions shown in Table 20 and then purified (elution: 25 μl), thereby preparing an open linear vector. Afterward, an in-fusion cloning reaction was performed under conditions shown in Table 21 at 37° C. for 15 minutes to transform E. coli DH5α or DH10β, and then the transformed cell was screened in an ampicillin-containing medium. Plasmids prepared from the collected colonies were sequenced, thereby obtaining a R587I variation-introduced Taq DNA polymerase mutant ("E507K/R536K/R587I/R660V").

TABLE 20

| | |
|---|---|
| 10X CutSmart Vector (NEB) | 2.5 μl |
| Taq plasmid (E507K/R536K/R660V) (200 ng/μl) | 21.5 μl |

TABLE 20-continued

| | |
|---|---|
| Kpn I-HF (NEB) | 0.5 μl |
| Xba I (NEB) | 0.5 μl |
| | 25 μl |

TABLE 21

| | |
|---|---|
| 5X EZ-fusio mix (Enzynomics) | 2 μl |
| Vector cleaved with Kpn I, Xba I (50 ng/μl) | 1 μl |
| F1 fragment (83 ng/μl) | 1 μl |
| F2 fragment (50 ng/μl) | 1 μl |
| Distilled water | 5 μl |
| | 10 μl |

[Example 5] Performance of qPCR Using "E507K/R536K/R587I/R660V" Taq Polymerase 5-1. Discrimination of Q61H Variations in KRAS Gene The Taq polymerase having the "E507K/R536K/R587I/R660V" variations obtained in Example 4 was used to confirm whether an ability of extending mismatched primers with respect to templates with Q61H SNPs in the KRAS gene was reduced. As a control, the Taq polymerase having "E507K/R536K/R660V" variations was used.

The template including a SNP was gDNA (104 copies, 33 ng/rxn) obtained from a HepG2 liver cancer cell line, and obtained by a typical DNA extraction method. It was confirmed that an entire detected target site corresponds to the NCBI reference sequence (NG_007524.1), and used as a wild-type (WT).

The sequence data of specific primers for the template is shown in Table 22 below.

TABLE 22

| Primer Name | | Sequence (5'-3') | Tm (° C.) |
|---|---|---|---|
| KRAS Q61H | Forward_Q (24 mer) | GAT ATT CTC GAC ACA GCA GGT CAA (SEQ ID NO: 43) | 64.2 |
| | Forward_H (24 mer) | GAT ATT CTC GAC ACA GCA GGT CAC (SEQ ID NO: 44) | 64.4 |
| | Reverse | ACA AAG AAA GCC CTC CCC AG (SEQ ID NO: 45) | 64.2 |

Conditions for qPCR (Applied Biosystems 7500 Fast) are the same as shown in Table 14 in Example 3. Probes are labeled as shown in Table 23 below.

TABLE 23

| Probe Name | Sequence (5'-3') | Tm (° C.) |
|---|---|---|
| Q61H FAM | TGC AAT GAG GGA CCA GTA CAT GAG G (SEQ ID NO: 46) | 67.6 |

Reaction conditions are the same as shown in Table 16 in Example 3, and the composition of the reaction buffer is the same as in Table 24 below.

TABLE 24

| |
|---|
| Reaction buffer (1X) |
| 50 mM Tris-Cl (pH 8.8) |
| 2.5 mM MgCl$_2$ |
| 60 mM KCl |

TABLE 24-continued 2.5 mM (NH$_4$)$_2$SO$_4$
25 mM TMAC
0.1% Tween 20
0.01% BSA

Figure 10A:
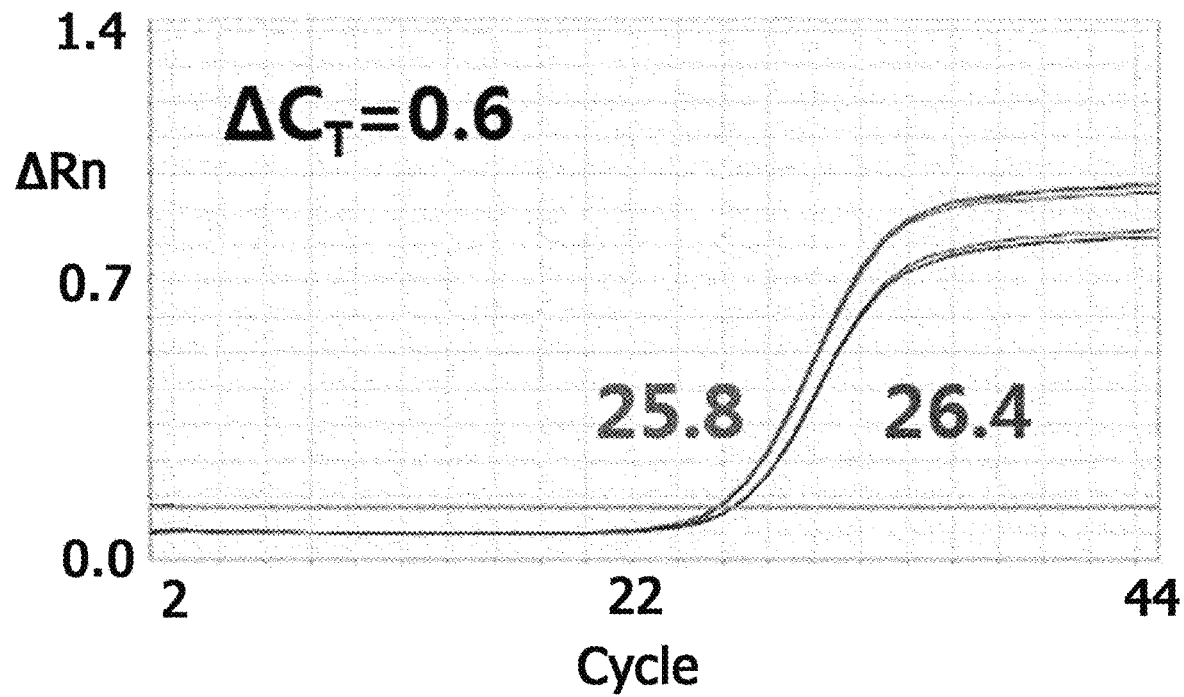
Figure 10B:
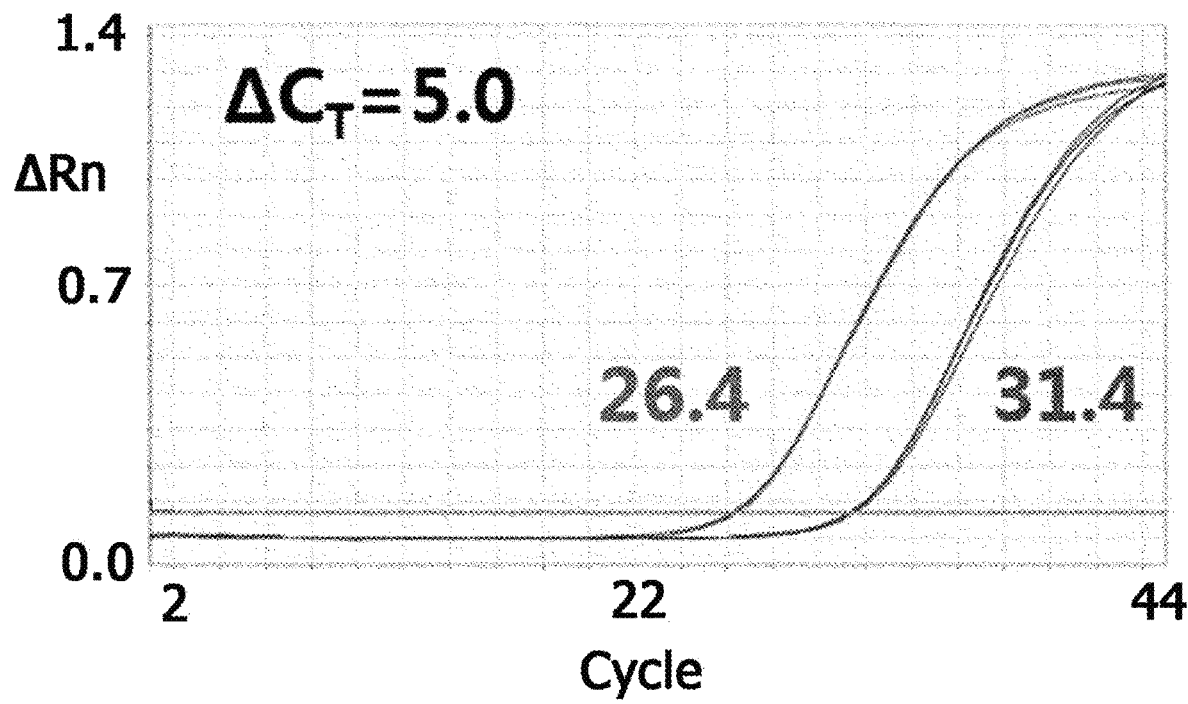

The other components of the reaction solution except a specific primer were prepared as shown in Table 22 in two tubes, and each allele-specific primer was added thereto, thereby performing qPCR. Here, a difference in cycle (Ct) value at which combined fluorescent signals detected from the tubes reach the threshold fluorescence value calculated with AB 7500 software (v2.0.6) was analyzed. It is considered that, as the Ct value in the amplification by a mismatched primer is delayed, high gene variation specificity or allele specificity is exhibited. As a result of AS-qPCR, as shown in FIGS. 10a and 10b, compared to the control E507K/R536K/R660V, the Taq polymerase having E507K/R536K/R587I/R660V variations was increased in ΔCt up to 5, indicating that the amplification by a mismatched primer was delayed.

The inventors further performed the above-described experiment once again using a primer shown in Table 25, which was manufactured by shortening the 24-mer primer of Table 22 to 18 mer. Except for using the composition of the reaction buffer in Table 26 below, all conditions are the same as those in the experiment using the 24-mer primer.

TABLE 25

| Primer Name | | Sequence (5'-3') | Tm (° C.) |
|---|---|---|---|
| KRAS Q61H | Forward_Q (18 mer) | CTC GAC ACA GCA GGT CAA (SEQ ID NO: 47) | 61.4 |
| | Forward_H (18 mer) | CTC GAC ACA GCA GGT CAC (SEQ ID NO: 48) | 61.8 |
| | Reverse | ACA AAG AAA GCC CTC CCC AG (SEQ ID NO: 49) | 64.2 |

TABLE 26

Figure 10C:
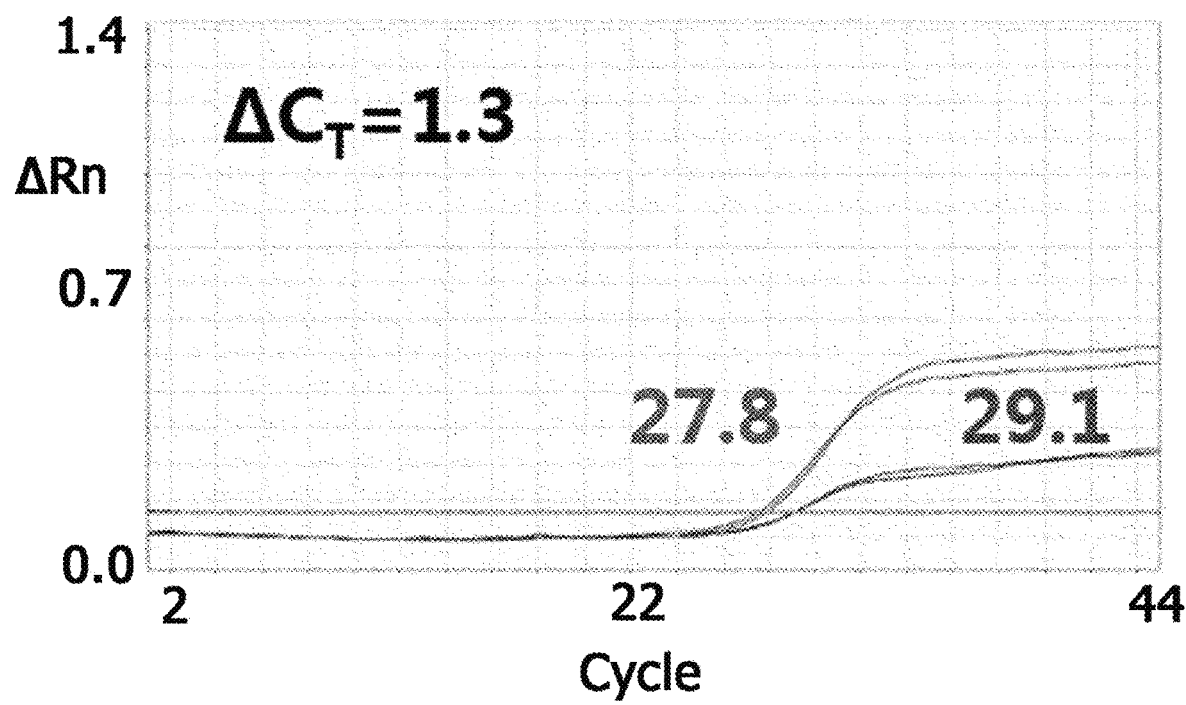
Figure 10D:
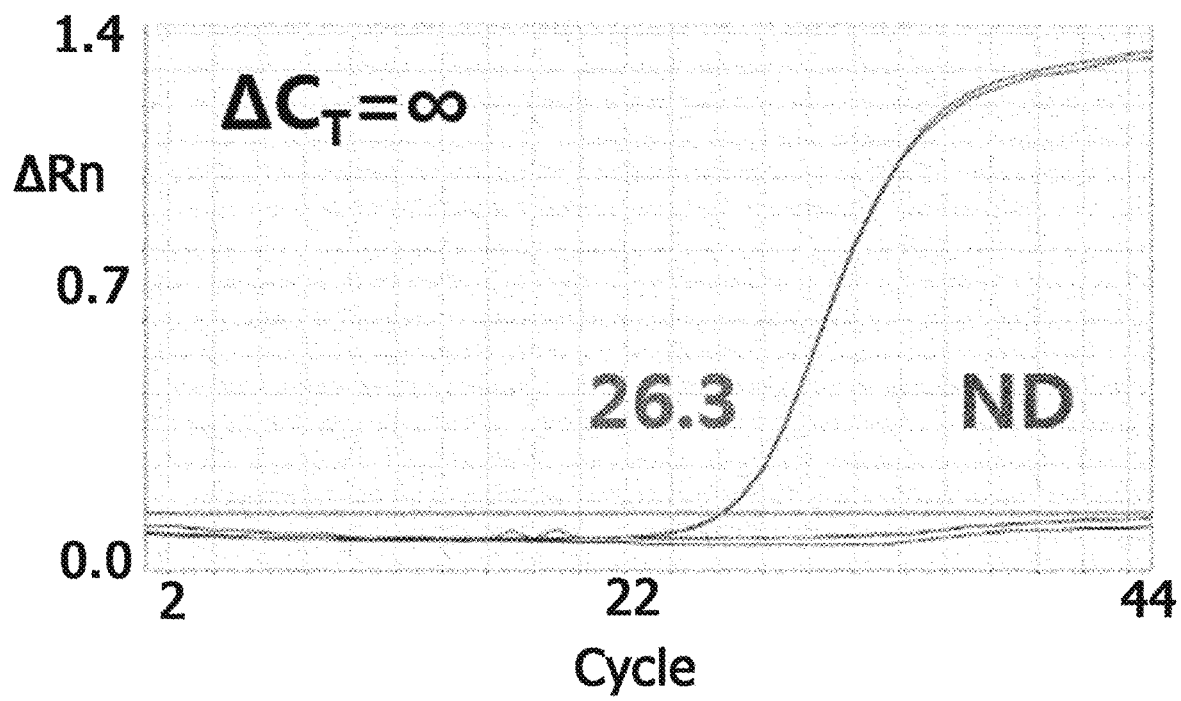

Reaction buffer (1X)
50 mM Tri-Cl (pH 8.8)
2.5 mM MgCl$_2$
15 mM (NH$_4$)$_2$SO$_4$
0.1% Tween 20
0.01% BSA Consequently, as shown in FIGS. 10c and 10d, compared to the control E507K/R536K/R660V, the Taq polymerase having E507K/R536K/R587I/R660V variations can confirm that the amplification by a mismatched primer is delayed. Particularly, the ΔCt of the R587I-introduced polymerase was more remarkably increased.

5-2. Discrimination of G13D Variations in KRAS Gene

The Taq polymerase having the "E507K/R536K/R587I/R660V" variations obtained in Example 4 was used to confirm whether an ability of extending mismatched primers with respect to templates with G13D SNPs in the KRAS gene was reduced. As a control, Taq polymerase having "E507K/R536K/R660V" variations was used.

The template including an SNP was gDNA (104 copies, 33 ng/rxn) obtained from a HepG2 liver cancer cell line, and obtained by a typical DNA extraction method. It was confirmed that an entire detected target site corresponds to the NCBI reference sequence (NG_007524.1), and used as a wild-type (WT).

The sequence data of specific primers for the template is shown in Table 27 below.

TABLE 27

| Primer Name | | Sequence (5'-3') | Tm (° C.) |
|---|---|---|---|
| KRAS G13D | Forward | ATA GGG CCT GCT GAA AAT GAC (SEQ ID NO: 50) | 61 |
| | Reverse_G (17mer) | GGC ACT CTT GCC TAC GC (SEQ ID NO: 51) | 62.4 |
| | Reverse_DGGC (17 mer) | ACT CTT GCC TAC GT (SEQ ID NO: 52) | 61.2 |

Conditions for qPCR (Applied Biosystems 7500 Fast) are the same as shown in Table 14 in Example 3. Probes are labeled as shown in Table 28 below.

TABLE 28

| Probe Name | Sequence (5'-3') | Tm (° C.) |
|---|---|---|
| G1213_R FAM | AGC TCC AAC TAC CAC AAG TTT ATA TTC AGT (SEQ ID NO: 53) | 66.2 |

Reaction conditions are the same as shown in Table 16 in Example 3, and the composition of the reaction buffer is the same as in Table 24 in Example 5-1. The other components of the reaction solution except a specific primer were prepared as shown in Table 27 in two tubes, and each allele-specific primer was added thereto, thereby performing qPCR. Here, a difference in cycle (Ct) value at which combined fluorescent signals detected from the tubes reach the threshold fluorescence value calculated with AB 7500 software (v2.0.6) was analyzed. It is considered that, as the Ct value in the amplification by a mismatched primer is delayed, high gene variation specificity or allele specificity is exhibited.

Figure 11:
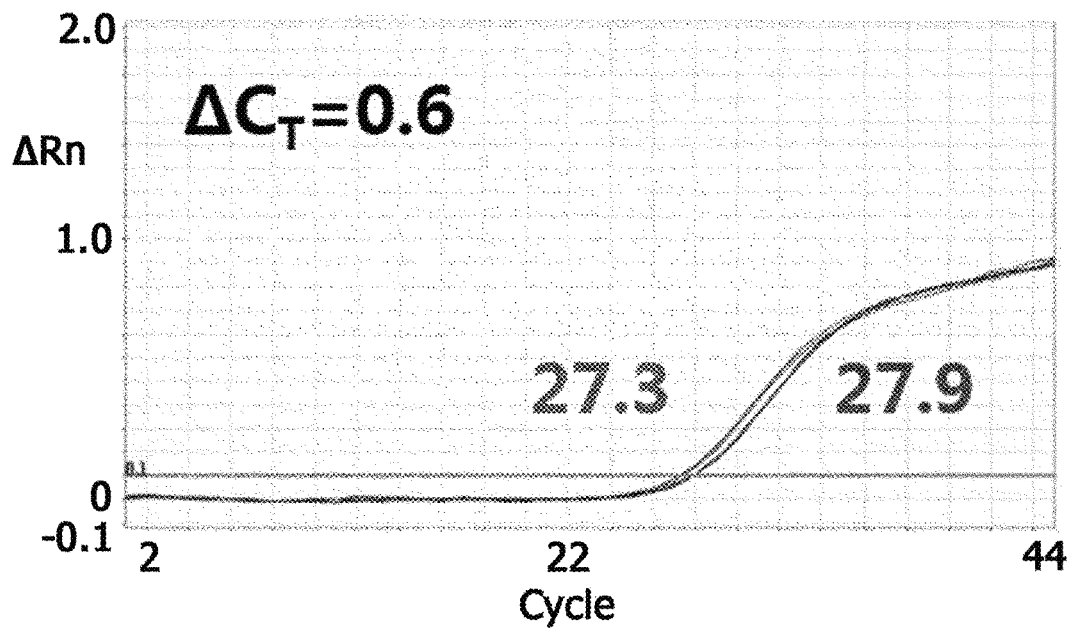
FIG. 11 shows the result obtained by AS-qPCR for a template having an SNP of G13D in a KRAS gene using a E507K/R536K/R587I/R660V polymerase, and Taq polymerase having E507K/R536K/R660V variations is used as a control.
Figure 11:
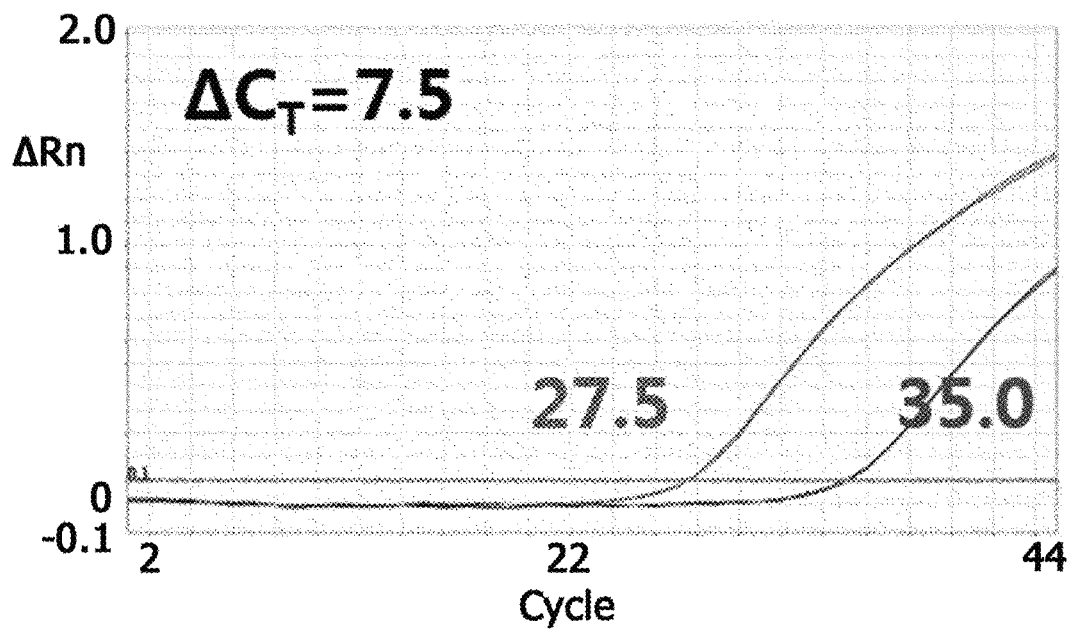

As a result of AS-qPCR, as shown in FIG. 11, compared to the control E507K/R536K/R660V, the Taq polymerase having E507K/R536K/R587I/R660V variations confirmed that the amplification by a mismatched primer was delayed.

5-3. Discrimination of G12S Variations in KRAS Gene

The Taq polymerase having the "E507K/R536K/R587I/R660V" variations obtained in Example 4 was used to confirm whether an ability of extending mismatched primers with respect to templates having G13S SNPs in the KRAS gene was reduced. As a control, the Taq polymerase having "E507K/R536K/R660V" variations was used.

The template having an SNP was gDNA (104 copies, 33 ng/rxn) obtained from a HepG2 liver cancer cell line, and obtained by a typical DNA extraction method. It was confirmed that an entire detected target site corresponds to the NCBI reference sequence (NG_007524.1), and used as a wild-type (WT).

The sequence data of specific primers for the template is shown in Table 29 below.

TABLE 29

| Primer Name | | Sequence (5'-3') | Tm (° C.) |
|---|---|---|---|
| KRAS G12S | Forward_G (23 mer) | TAA ACT TGT GGT AGT TGG AGC TG (SEQ ID NO: 54) | 62.6 |
| | Forward_S (23 mer) | TAA ACT TGT GGT AGT TGG AGC TA (SEQ ID NO: 55) | 61.6 |

TABLE 29 -continued

| Primer Name | | Sequence (5'-3') | Tm (° C.) |
|---|---|---|---|
| | Reverse | CAT ATT CGT CCA CAA AAT GAT TCT GAA T (SEQ ID NO: 56) | 63 |

Conditions for qPCR (Applied Biosystems 7500 Fast) are the same as shown in Table 14 in Example 3. Probes are labeled as shown in Table 30 below.

TABLE 30

| Probe Name | Sequence (5'-3') | Tm (° C.) |
|---|---|---|
| G1213_F FAM | AGC TGT ATC GTC AAG GCA CTC TTG C (SEQ ID NO: 57) | 68.2 |

Reaction conditions are the same as shown in Table 16 in Example 3, and the composition of the reaction buffer is the same as in Table 24 in Example 5-1. The other components of the reaction solution except a specific primer were prepared as shown in Table 29 in two tubes, and each allele-specific primer was added thereto, thereby performing qPCR. Here, a difference in cycle (Ct) value at which combined fluorescent signals detected from the tubes reach the threshold fluorescence value calculated with AB 7500 software (v2.0.6) was analyzed. It is considered that, as the Ct value in the amplification by a mismatched primer is delayed, high gene variation specificity or allele specificity is exhibited.

Figure 12:
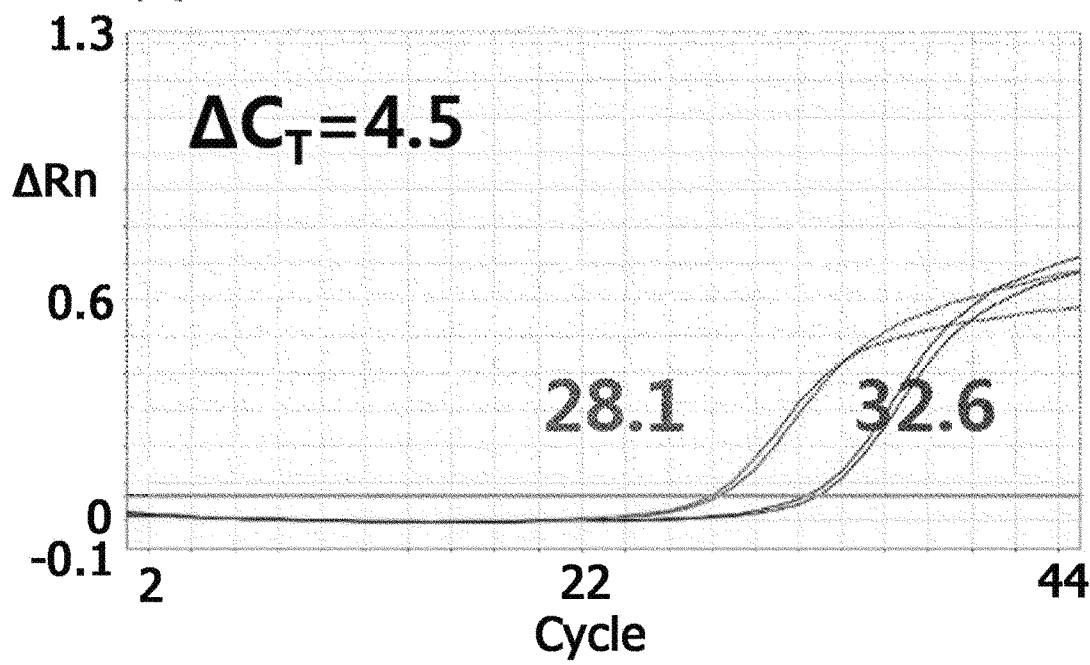
FIG. 12 shows the result obtained by AS-qPCR for a template having an SNP of G12S in a KRAS gene using a E507K/R536K/R587I/R660V polymerase, and Taq polymerase having E507K/R536K/R660V variations is used as a control.
Figure 12:
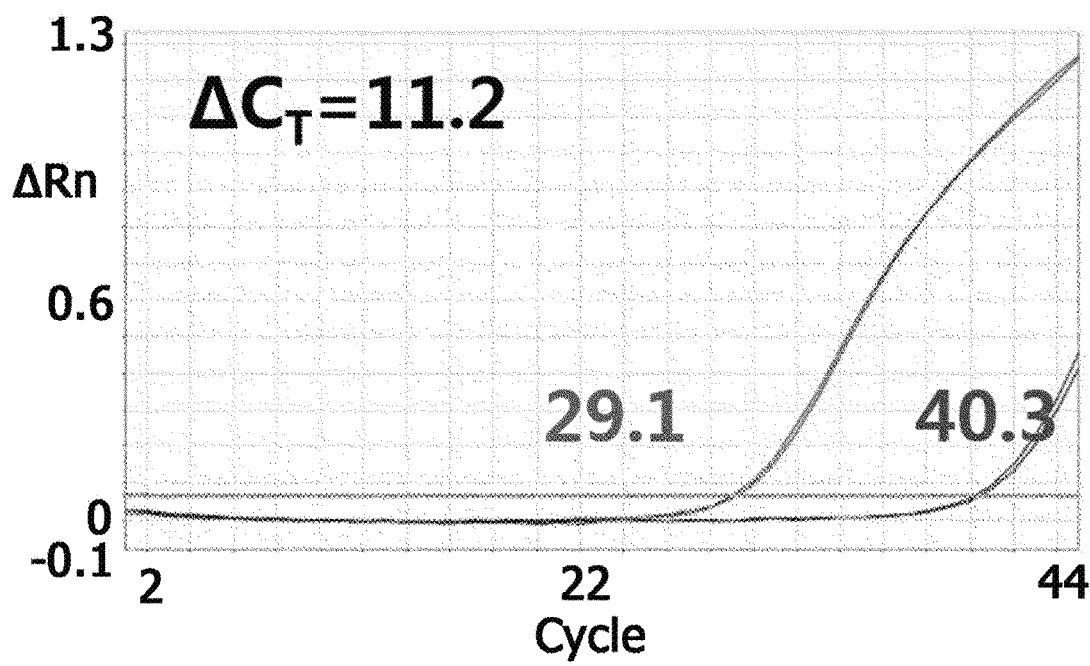

As a result of AS-qPCR, as shown in FIG. 12, compared to the control E507K/R536K/R660V, the Taq polymerase having E507K/R536K/R587I/R660V variations confirmed that the amplification by a mismatched primer was delayed.

5-4. Discrimination of L858R Variations in EGFR Gene

The Taq polymerase having the "E507K/R536K/R587I/R660V" variations obtained in Example 4 was used to confirm whether an ability of extending mismatched primers with respect to templates with L858R SNPs in EGFR gene was reduced. As a control, Taq polymerase having "E507K/R536K/R660V" variations was used.

The template including a SNP was gDNA (104 copies, 33 ng/rxn) obtained from a HepG2 liver cancer cell line, and obtained by a typical DNA extraction method. It was confirmed that an entire detected target site corresponds to the NCBI reference sequence (NG_007726.3), and used as a wild-type (WT).

The sequence data of specific primers for the template is shown in Table 31 below.

TABLE 31

| Primer Name | | Sequence (5'-3') | Tm (° C.) |
|---|---|---|---|
| EGFR L858R | Forward | ACC TGG CAG CCA GGA ACG TA (SEQ ID NO: 58) | 67.8 |
| | Reverse_L | GCA CCC AGC AGT TTG GCC A (SEQ ID NO: 59) | 68.2 |
| | Reverse_R | GCA CCC AGC AGT TTG GCC C (SEQ ID NO: 60) | 67.7 |

Conditions for qPCR (Applied Biosystems 7500 Fast) are the same as shown in Table 14 in Example 3. Probes are labeled as shown in Table 32 below.

TABLE 32

| Probe Name | Sequence (5'-3') | Tm (° C.) |
|---|---|---|
| L858R FAM_R | CAG CAT GTC AAG ATC ACA GAT TTT GGG C (SEQ ID NO: 61) | 67.8 |

Reaction conditions are the same as shown in Table 16 in Example 3, and the composition of the reaction buffer is the same as in Table 24 in Example 5-1. The other components of the reaction solution except a specific primer were prepared as shown in Table 31 in two tubes, and each allele-specific primer was added thereto, thereby performing qPCR. Here, a difference in cycle (Ct) value at which combined fluorescent signals detected from the tubes reach the threshold fluorescence value calculated with AB 7500 software (v2.0.6) was analyzed. It is considered that, as the Ct value in the amplification by a mismatched primer is delayed, high gene variation specificity or allele specificity is exhibited.

Figure 13:
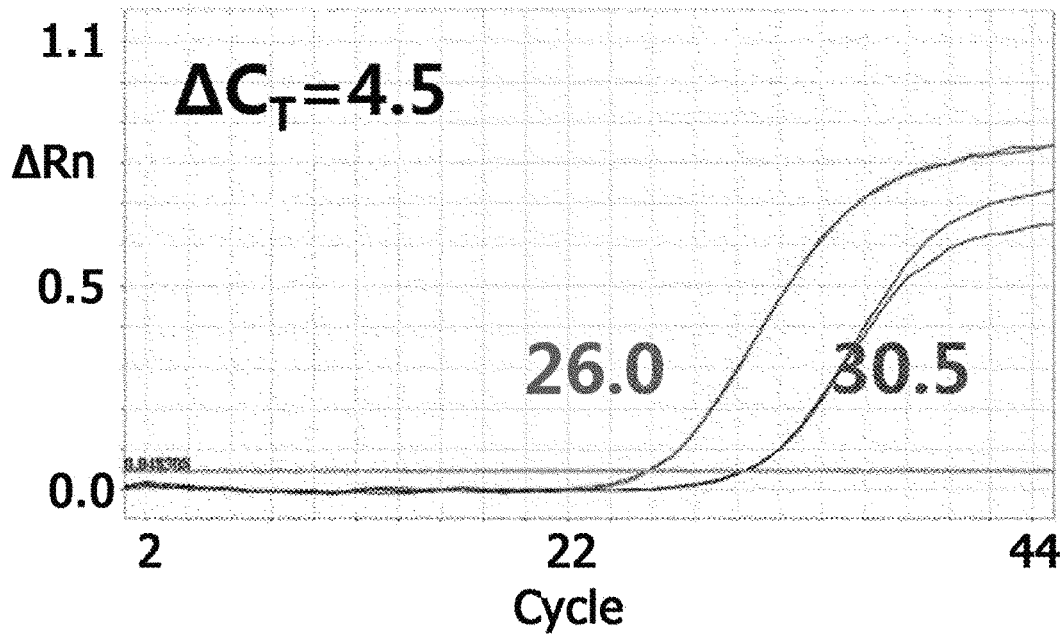
FIG. 13 shows the result obtained by AS-qPCR for a template having an SNP of L585R in an EGFR gene using a E507K/R536K/R587I/R660V polymerase, and Taq polymerase having E507K/R536K/R660V variations is used as a control.
Figure 13:
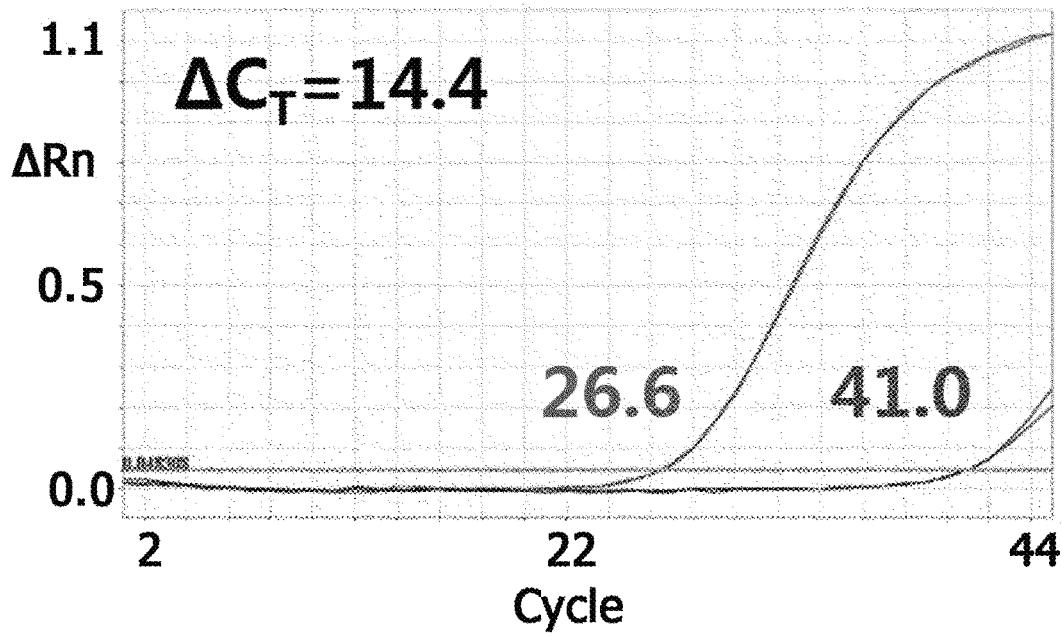
Figure 14A:
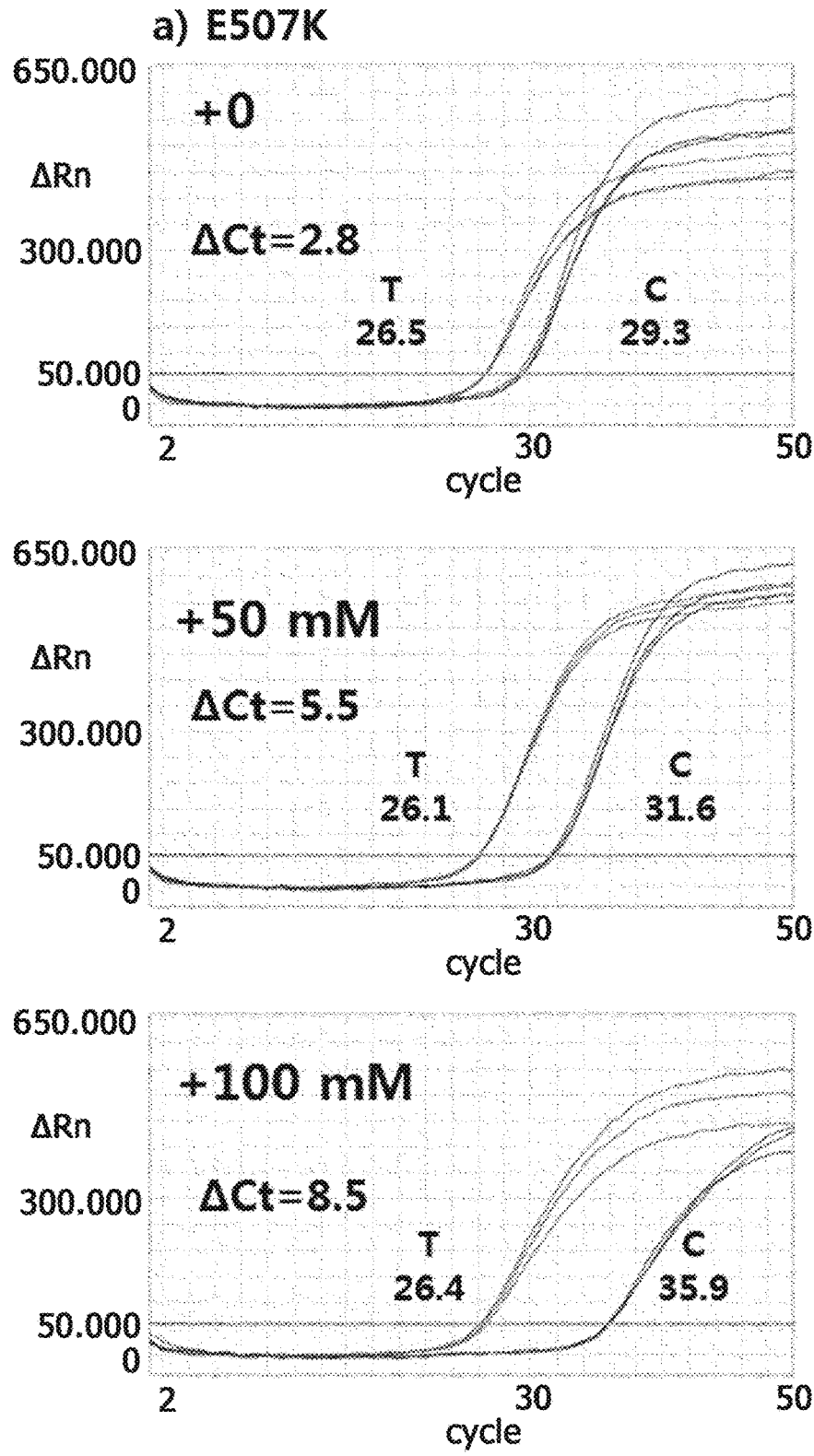
FIGS. 14a to 14d are graphs showing the amplification delay effect by mismatch according to the change in KCl concentration of a reaction buffer using E507K, E507K/R536K, E507K/R660V and E507K/R536K/R660V Taq polymerases of the present invention.
Figure 14B:
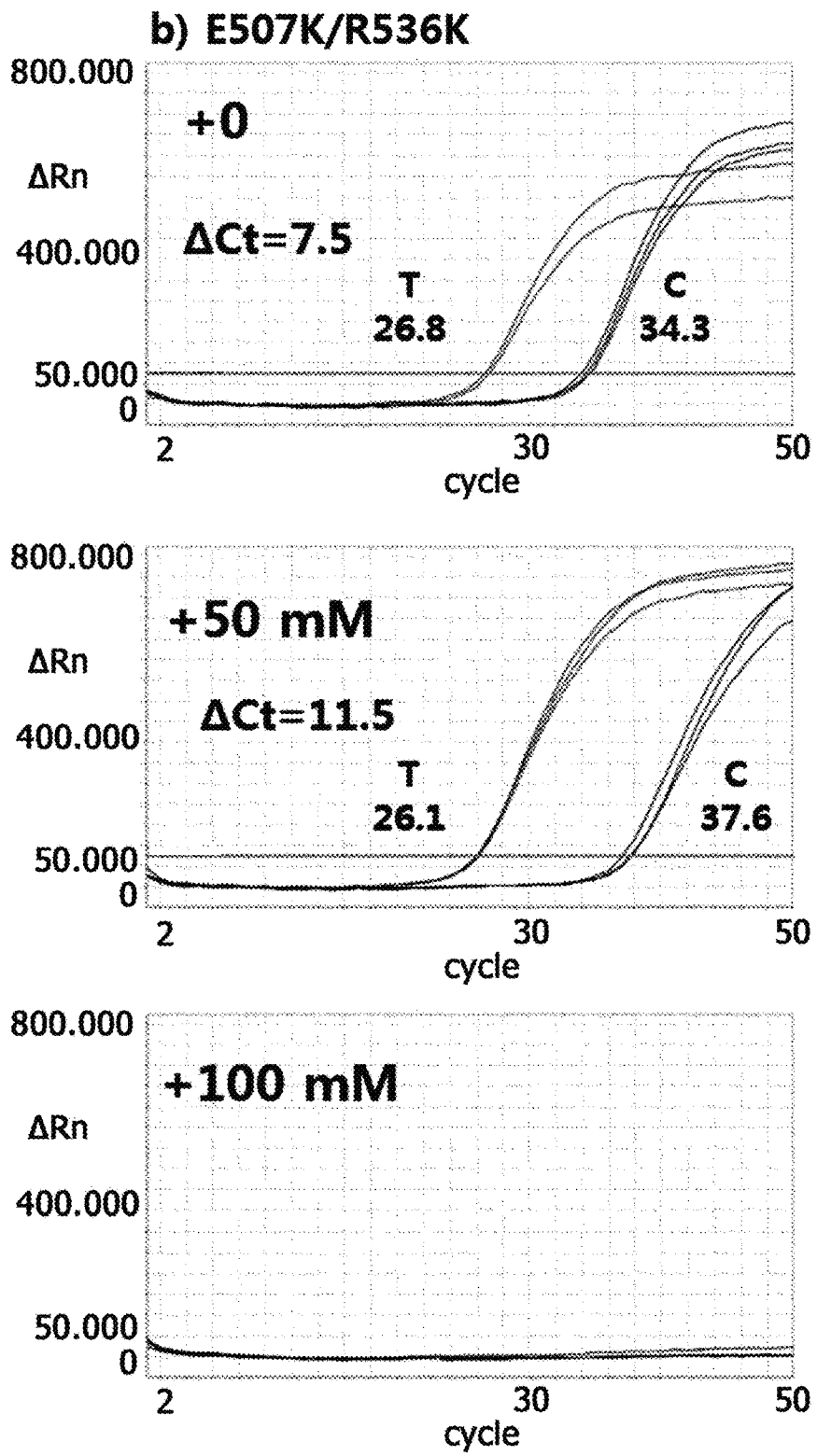
Figure 14C:
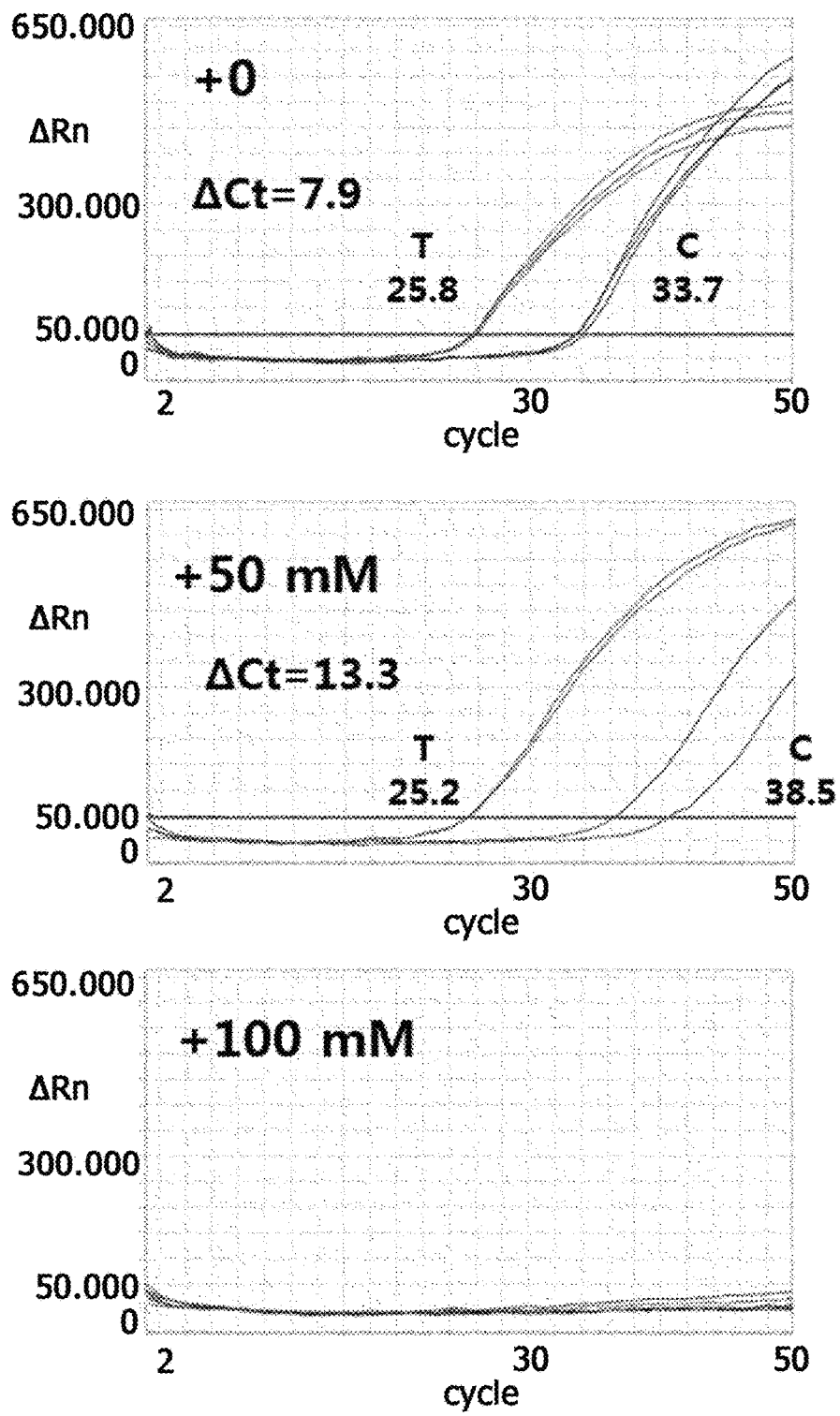
Figure 14D:
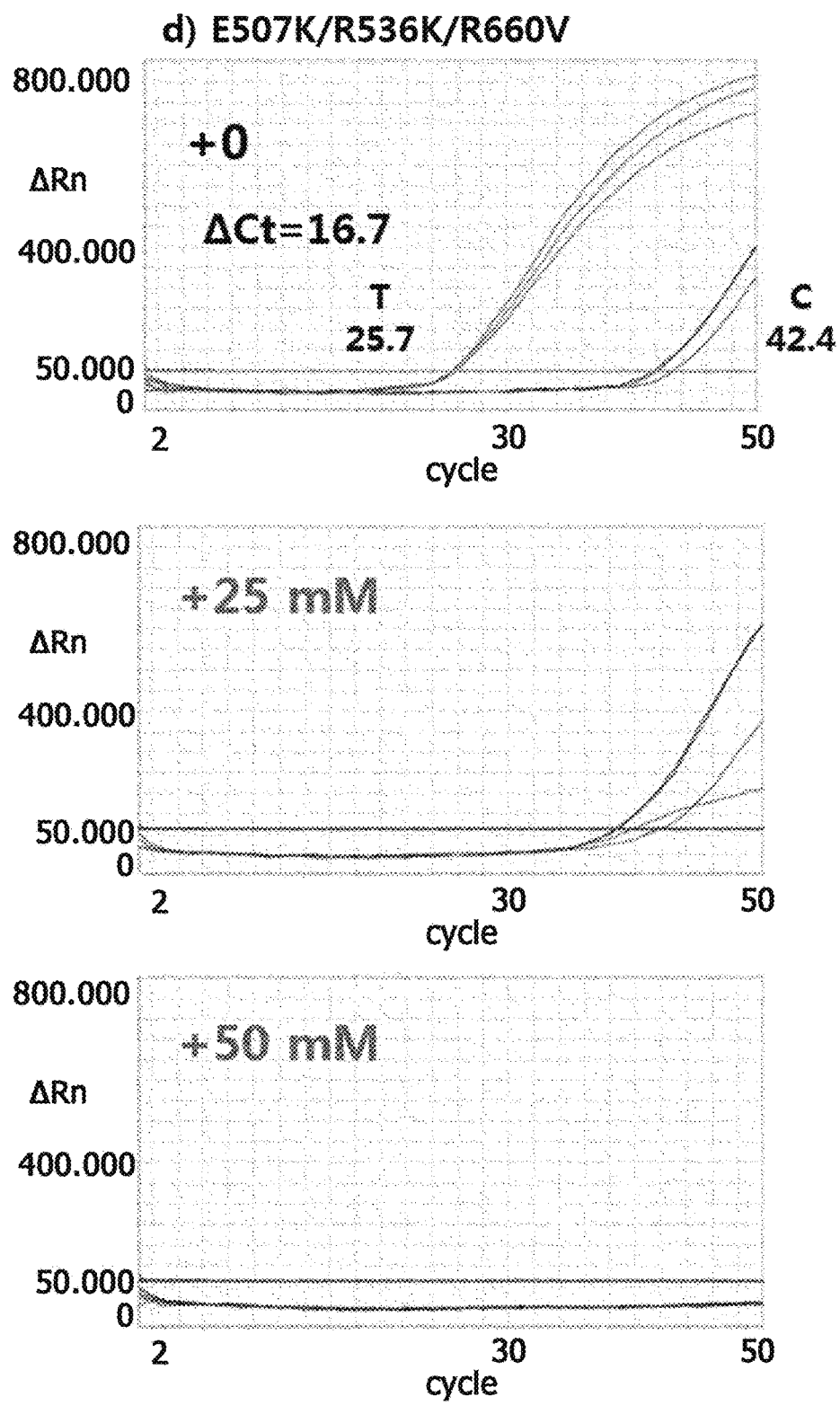

As a result of AS-qPCR, as shown in FIG. 13, compared to the control E507K/R536K/R660V, the Taq polymerase having E507K/R536K/R587I/R660V variations confirmed that the amplification by a mismatched primer was delayed.

As described above, it was confirmed that some of the Taq DNA polymerases having E507K/R536K/R587I/R660V variations according to the present invention, compared to the Taq polymerase having E507K/R536K/R660V variations, have excellent mismatch extension selectivity. Therefore, the Taq DNA polymerases having E507K/R536K/R587I/R660V variations according to the present invention are also expected to be usefully applied to the medical diagnosis of a disease and recombinant DNA studies.

Example 61

Optimization of KCl Concentration in Reaction Buffer

In this example, to find a high cation concentration in a state in which the amplification by mismatching is delayed as much as possible, and the amplification efficiency by matching is not reduced, an optimal KCl concentration was confirmed by adjusting a KCl concentration in a PCR buffer.

The Taq polymerases having "E507K/R536K," "E507K/R660V" and "E507K/R536K/R660V" variations, respectively, obtained in Example 2 were used to compare a KCl concentration threshold with the Taq polymerase having the E507K variation.

As a template having an SNP, rs1408799 was used, the genotype of the template was TT, and as a primer, an rs1408799 primer shown in Table 2 was used. qPCR (Applied Biosystems 7500 Fast) was performed under the conditions shown in Table 14, a dual-labeled probe is 1408799-FAM shown in Table 15, the reaction conditions are shown in Table 33, and the composition of the reaction buffer is shown in Table 34.

TABLE 33

| 5X Reaction buffer | 4 µl |
|---|---|
| dNTP (10 mM each) | 0.5 µl |
| Forward primer (2 µM) | 1 µl |
| Reverse primer (2 µM) | 1 µl |
| Nuclease-free distilled water | 10 µl |
| Acquired template (TT) | 1 µl |
| Taq polymerase (2 U/µl) | 0.5 µl |
| Dual-labeled probe (4 µM) | 2 µl |
| 20 µl | |

TABLE 34

| Reaction buffer (1X) | |
|---|---|
| 50 mM Tris-Cl (pH 8.8) | |
| 2.5 mM MgCl$_2$ | |
| x mM KCl | |
| 2.5 mM (NH$_4$)$_2$SO$_4$ | |
| 0.1% Tween 20 | |
| 0.01% BSA | |

Consequently, as shown in FIGS. 14a to 14d, it was confirmed that the E507K/R536K/R660V Taq polymerase has the lowest KCl concentration threshold, and the E507K/R536K and E507K/R660V have lower KCl concentration thresholds than E507K. Based on the result, to determine the optimal KCl concentration, an additional experiment was performed using the E507K/R536K/R660V Taq polymerase. A primer was the rs1408799-T-specific primer shown in Table 13, qPCR (Applied Biosystems 7500 Fast) was performed for 35 cycles under the conditions shown in Table 14, and reaction conditions are shown in Table 35.

TABLE 35

| 5X Reaction buffer | 4 µl |
|---|---|
| dNTP (10 mM each) | 0.5 µl |
| Forward primer (2 µM) | 1 µl |
| Reverse primer (2 µM) | 1 µl |
| Nuclease-free distilled water | 12 µl |
| Acquired template (TT) | 1 µl |
| E507K/R536K/R660V (2 U/µl) | 0.5 µl |
| 20 µl | |

The composition of a reaction buffer for the control is shown in Table 36, and the composition of a reaction buffer for the experimental group is shown in Table 34. The (NH$_4$)$_2$SO$_4$ concentration was constantly fixed at 2.5 mM, and the KCl concentration varied.

TABLE 36

| Control buffer (1X) | |
|---|---|
| 50 mM Tris-Cl (pH 8.8) | |
| 1M betaine | |
| 2.5 mM MgCl$_2$ | |
| 50 mM KCl | |
| 2.5 mM (NH$_4$)$_2$SO$_4$ | |
| 0.1% Tween 20 | |
| 0.01% BSA | |

Amplification was performed under the above-mentioned conditions, and the PCR product was identified by electrophoresis, thereby confirming that, as shown in FIG. 15, an optimal KCl concentration in a state in which the amplification by mismatching is delayed as much as possible, and the amplification efficiency by matching is not reduced is 75 mM.

Example 7

Optimization of (NH$_4$)$_2$SO$_4$ Concentration in Reaction Buffer

In this example, based on the result of Example 4, the optimal (NH$_4$)$_2$SO$_4$ concentration was confirmed by constantly fixing a KCl concentration in a reaction buffer at 75 mM and variously changing a (NH$_4$)$_2$SO$_4$ concentration. As a primer, the rs1408799-T-specific primer shown in Table 13 was used. qPCR (Applied Biosystems 7500 Fast) was performed for 35 cycles under the conditions shown in Table 14, reaction conditions are shown in Table 35, and the composition of a reaction buffer for the control is shown in Table 36.

Consequently, as shown in FIG. 16, it was confirmed that an optimal (NH$_4$)$_2$SO$_4$ concentration is 5 mM.

Based on the result, an amplification delay effect caused by mismatching was further confirmed by constantly fixing the KCl concentration in the reaction buffer at 75 mM, and setting the (NH$_4$)$_2$SO$_4$ concentration to approximately 5 mM (each of 2.5 mM, 5 mM and 10 mM).

As a primer, the rs1408799 primer shown in Table 13 was used, a dual-labeled probe is 1408799-FAM shown in Table 15, and reaction conditions are shown in Table 37 below.

TABLE 37

| 5X Reaction buffer | 4 µl |
|---|---|
| dNTP (10 mM each) | 0.5 µl |
| Forward primer (2 µM) | 1 µl |
| Reverse primer (2 µM) | 1 µl |
| Nuclease-free distilled water | 10 µl |
| Acquired template (TT) | 1 µl |
| E507K/R536K/R660V (2 U/µl) | 0.5 µl |
| Dual-labeled probe (4 µM) | 2 µl |
| 20 µl | |

Consequently, as shown in FIG. 17, when the (NH$_4$)$_2$SO$_4$ concentration was 10 mM, the Ct value difference was the largest, but Ct was a little delayed and a peak was tilted in the amplification caused by matching, and the optimal (NH$_4$)$_2$SO$_4$ concentration was determined to be 5 mM. By combining the results of Examples 6 and 7, it was confirmed that the optimal composition of a reaction buffer contains 50 mM Tris-Cl, 2.5 mM MgCl$_2$, 75 mM KCl, 5 mM (NH$_4$)$_2$SO$_4$, 0.1% Tween 20 and 0.01% BSA.

Example 81

Addition of TMAC to Reaction Buffer and Optimization of TMAC Concentration

In this example, the optimal concentration was confirmed by adding TMAC to a reaction buffer. Based on the results of Examples 6 and 7, the optimal TMAC concentration was determined by constantly fixing a KCl concentration at 75 mM and a (NH$_4$)$_2$SO$_4$ concentration at 5 mM, and variously changing a TMAC concentration.

A E507K/R536K or E507K/R536K/R660V Taq polymerase was used, and as a template having an SNP, rs1408799 was used. The genotype of the template was TT, and as a primer, the rs1408799 primer shown in Table 13 was used. qPCR (Applied Biosystems 7500 Fast) was performed under the conditions shown in Table 14, a dual-labeled probe is 1408799-FAM shown in Table 15, and reaction conditions are shown in Table 37.

Consequently, as shown in FIGS. 18a and 18b, it was confirmed that, for the E507K/R536K Taq polymerase, the optimal TMAC concentration is 60 mM, and for the E507K/R536K/R660V Taq polymerase, the optimal TMAC concentration is 25 mM. When the TMAC concentration is very high, amplification efficiency was reduced.

Example 91

Optimization of KCl, (NH$_4$)$_2$SO$_4$ and TMAC Concentrations in Reaction Buffer In this Example, based on the result shown in Example 8, the optimal KCl, (NH$_4$)$_2$SO$_4$ and TMAC concentrations in a reaction buffer were confirmed using the E507K/R536K/R660V Taq polymerase.

Specifically, the TMAC concentration was constantly fixed at 25 mM, the (NH$_4$)$_2$SO$_4$ concentration was constantly fixed at 2.5 mM, and then the KCl concentration was changed to 20, 40, 60 or 80 mM. An experiment was performed on two SNPs of rs1015362 and rs4911414, and the genotype of the template is shown in Table 12, primers were the rs1015362 and rs4911414 primers shown in Table 13, qPCR (Applied Biosystems 7500 Fast) was performed under the conditions shown in Table 14, a dual-labeled probe is 1408799-FAM shown in Table 15, and reaction conditions are shown in Table 37.

Consequently, as shown in FIGS. 19a and 19b the optimal KCl concentration for two SNPs was 60 mM, and it can be observed that when the KCl concentration was 80 mM, amplification efficiency was reduced.

From the above-described results, it was confirmed that the optimal KCl concentration in the reaction buffer was 60 mM, the optimal $(NH_4)_2SO_4$ concentration was 2.5 mM, and the optimal TMAC concentration was 25 mM, and in further detail, for the E507K/R536K polymerase, 75 mM KCl, 5 mM $(NH_4)_2SO_4$ and 60 mM TMAC were most effectively used, and for the E507K/R536K/R660V polymerase, 60 mM KCl, 2.5 mM $(NH_4)_2SO_4$ and 25 mM TMAC were most effectively used.

INDUSTRIAL APPLICABILITY

Since the DNA polymerase with increased gene variation specificity according to the present invention has a higher mismatch-to-match extension selectivity than conventional Taq polymerase, reliable gene variation-specific amplification is possible without any substrate modification. The present invention provides an optimal PCR buffer composition that allows the proper function of a DNA polymerase with increased gene variation specificity to be effectively exhibited, and reliable gene variation-specific amplification is possible by considerably increasing the activity of the DNA polymerase using the DNA polymerase with increased gene variation specificity. Moreover, a kit including a PCR buffer composition and/or the DNA polymerase with increased gene variation specificity according to the present invention can effectively detect a gene variation or SNP, and thus can be usefully applied to the medical diagnosis of a disease and recombinant DNA studies.

The invention claimed is:

1. A Taq polymerase mutant wherein the Taq polymerase mutant consists of the amino acid sequence of SEQ ID NO: 8 that has 3 amino acid substitutions in SEQ ID NO: 1, wherein glutamic acid (E) at position 507 of SEQ ID NO:1 is substituted with lysine (K) arginine (R) at position 536 of SEQ ID NO:1 is substituted with lysine (K), and arginine (R) at position 660 of SEQ ID NO:1 is substituted with valine (V), and wherein the mutant has Taq polymerase activity.

2. The Taq polymerase mutant of claim 1, wherein the Taq polymerase mutant is used for discriminating a matched primer from a mismatched primer by comparing a Ct value of a quantitative polymerase chain reaction (qPCR) in the presence of a nucleic acid template and the matched primer with a Ct value of a qPCR in the presence of the nucleic acid template and the mismatched primer, wherein both the matched primer and the mismatched primer are capable of hybridizing with a target sequence of the nucleic acid template, and the mismatched primer has a non-complementary nucleotide at its 3' end after it hybridizes to the target sequence of the nucleic acid template;

wherein the matched primer consisting of a nucleotide sequence of SEQ ID NO: 26, the mismatched primer consisting of a nucleotide sequence of SEQ ID NO: 27, and the nucleic acid template is a nucleic acid comprising a single nucleotide polymorphisms (SNP) rs1408799; or wherein the matched primer consisting of a nucleotide sequence of SEQ ID NO: 29, the mismatched primer comprises a nucleotide sequence of SEQ ID NO: 30, and the nucleic acid template is a nucleotide acid comprising a SNP rs1015362; or wherein the matched primer consisting of a nucleotide sequence of SEQ ID NO: 31, the mismatched primer consisting of a nucleotide sequence of SEQ ID NO: 32, and the nucleic acid template is a nucleotide acid comprising a SNP rs4911414.

3. A method of in vitro detecting a single nucleotide polymorphisms (SNP) in a nucleic acid template, the method comprising:

conducting a qPCR in the presence of the Taq polymerase mutant DNA polymerase of claim 1 and the nucleic acid template.

4. A PCR kit comprising the Taq polymerase mutant of claim 1, a matched primer and a mismatched primer, wherein the matched primer and the mismatched primer are hybridized with a target sequence.

5. A PCR kit comprising the Taq polymerase mutant of claim 1 and a nucleoside triphosphate.

6. A PCR kit comprising:
(a) the Taq polymerase mutant DNA polymerase of claim 1;
(b) one or more buffers;
(c) a quantification reagent binding to a double-stranded DNA;
(d) a polymerase blocking antibody;
(e) one or more control values or control sequences; and
(f) one or more nucleic acid templates.

7. A Taq polymerase mutant, wherein the Taq polymerase mutant consists of the amino acid sequence of SEQ ID NO: 37 that has 4 amino acid substitutions in SEQ ID NO: 1, wherein glutamic acid (E) at position 507 of SEQ ID NO: 1 is substituted with lysine (K), arginine (R) at position 536 of SEQ ID NO: 1 is substituted with lysine (K), arginine (R) at position 587 is substituted with isoleucine (I), and arginine (R) at position 660 of SEQ ID NO: 1 is substituted with valine (V), and wherein the mutant has Taq polymerase activity.

8. The Taq polymerase mutant of claim 7, wherein the Taq polymerase mutant is used for discriminating a matched primer from a mismatched primer by comparing a Ct value of a quantitative polymerase chain reaction (qPCR) in the presence of a nucleic acid template and the matched primer with a Ct value of a qPCR in the presence of the nucleic acid template and the mismatched primer, wherein both the matched primer and the mismatched primer are capable of hybridizing with a target sequence of the nucleic acid template, and the mismatched primer has a non-complementary nucleotide at its 3' end after it hybridizes to the target sequence of the nucleic acid template;

wherein the matched primer consists of a nucleotide sequence of SEQ ID NO: 43 and the mismatched primer consists of a nucleotide sequence of SEQ ID NO: 44 when the nucleic acid template is a KRAS gene comprising Q61H variation, or the matched primer consists of a nucleotide sequence of SEQ ID NO: 47 and the mismatched primer consists of a nucleotide sequence of SEQ ID NO: 48 when the nucleic acid template is a KRAS gene comprising Q61H variation; or wherein the matched primer consists of a nucleotide sequence of SEQ ID NO: 51 and the mismatched primer consists of a nucleotide sequence of SEQ ID NO: 52 when the nucleic acid template is a KRAS gene comprising G13D variation; or wherein the matched primer consists of a nucleotide sequence of SEQ ID NO: 54 and the mismatched primer consists of comprises a nucleotide sequence of SEQ ID NO: 55 when the nucleic acid template is a KRAS gene comprising G12S variation; or wherein the matched primer consists of a nucleotide sequence of SEQ ID NO: 59 and the mismatched primer consists of a nucleotide sequence of SEQ ID NO: 60 when the nucleic acid template is a EGFR gene comprising L585R variation.

9. A method of in vitro detecting an SNP in a template, the method comprising:
conducting a qPCR in the presence of the Taq polymerase mutant DNA polymerase of claim 2 and the nucleic acid template.

10. A PCR kit comprising the Taq polymerase mutant of claim 7, a matched primer and a mismatched primer, wherein the matched primer and the mismatched primer are hybridized with a target sequence.

11. A PCR kit comprising the Taq polymerase mutant of claim 7 and a nucleoside triphosphate.

12. A PCR kit comprising:
(a) the Taq polymerase mutant DNA polymerase of claim 7;
(b) a nucleoside triphosphate;
(c) one or more buffers;
(d) a quantification reagent binding to a double-stranded DNA;
(e) a polymerase blocking antibody;
(f) one or more control values or control sequences; and
(g) one or more nucleic acid templates.

13. A method of performing a competitive allele-specific TaqMan (CAST) PCR, a droplet digital PCR or a mass spectrometry using the PCR kit of claim 4, wherein the mismatched primer in the PCR kit is a mutant allele-specific primer, and wherein the PCR kit further comprises a wild type allele-specific blocker.

14. A method of performing a CAST PCR, a droplet digital PCR or a mass spectrometry using the PCR kit of claim 10, wherein the mismatched primer in the PCR kit is a mutant allele-specific primer, and wherein the PCR kit further comprises a wild type allele-specific blocker.

* * * * *